United States Patent [19]
Beach

[11] Patent Number: 5,998,582
[45] Date of Patent: Dec. 7, 1999

[54] D-TYPE CYCLINS AND USES RELATED THERETO

[75] Inventor: David H. Beach, Huntington Bay, N.Y.

[73] Assignee: Cold Spring Harbor Laboratory, Cold Spring Harbor, N.Y.

[21] Appl. No.: 08/246,361

[22] Filed: May 19, 1994

Related U.S. Application Data

[60] Division of application No. 07/963,308, Oct. 16, 1992, which is a continuation-in-part of application No. 07/888,178, May 26, 1992, abandoned, and a continuation-in-part of application No. 07/701,514, May 16, 1991.

[51] Int. Cl.$^6$ .......................... C07K 14/47; C12P 21/02; C12N 9/12
[52] U.S. Cl. ...................... 530/350; 435/69.1; 435/69.7; 435/194
[58] Field of Search .................................. 435/194, 69.1, 435/69.7; 530/350; 536/23.5

[56] References Cited

PUBLICATIONS

Motokura, T. et al. (1991) "A novel cyclin encoded by a bcl1–linked candidate gene" Nature 350:512–515, Apr. 1991.

*Primary Examiner*—Kawai Lau
*Attorney, Agent, or Firm*—Anita Varma; Foley, Hoag & Eliot LLP

[57] ABSTRACT

A novel class of cyclins, referred to as D-type cyclins, of mammalian origin, particularly human origin, DNA and RNA encoding the novel cyclins, and a method of identifying other D-type and non-D type cyclins. Also disclosed are a method of detecting an increased level of a D-type cyclin and a method of inhibiting cell division by interfering with formation of the protein kinase-D type cyclin complex essential for cell cycle start.

36 Claims, 29 Drawing Sheets

```
GCAGTAGCACCGAGCAGCAGAGTCCGCACGCTCCGGCGAGGGCCAGAAGAGCCCGAGGGA    60
GCGCGGGGGCAGCAGAAGCUGAGCGCAGCGCGGAGACCCAGAGACCCACAGCCCTCCCC   120

AGCTGCCCAGAAGAGCCCAGCCATGGAACACCAGCTCCTGTGCTGCGAAGTGGAAACC   180
                    M  E  H  Q  L  L  C  C  E  V  E  T       12
ATCCGCGCGCGCTACCCCGATGCCAACCTCCTCAACGACCGGGTGCTGCGGGCCATGCTG   240
 I  R  R  A  Y  P  D  A  N  L  L  N  D  R  V  L  R  A  M  L    32

AAGGCCGGAGGAGACCTGCGCGCCCCTCGGTGTCCTACTTCAAATGTGTGCAGAACGACGTC   300
 K  A  E  E  T  C  A  P  S  V  S  Y  F  K  C  V  Q  K  E  V    52
CTGCCGTCCATGCGGAAGATCGTCGCCACCTGGATGCTGGAGGTCTGCGAGGAACAGAAG   360
 L  P  S  M  R  K  I  V  A  T  W  M  L  E  V  C  E  E  Q  K    72

TGCGAGGAGGAGTCTTCCCGCTGGCCATGAACTACCTGGACCGCTTCCTGTCGCTGGAG   420
 C  E  E  V  F  F  P  L  A  M  N  Y  L  D  R  F  L  S  L  E    92
CCCGTGAAAAAGAGCCGCCTGCAGCTGCATGTTCGTGGCCTCTAAG   480
 P  V  K  K  S  R  L  Q  L  G  A  T  C  M  F  V  A  S  K     112

ATGAAGGAGACCATCCCCCTGACGGCCGAGAAGCTGTGCATCTACACGACGCCTCCATC   540
 M  K  E  T  I  P  L  T  A  E  K  L  C  I  Y  T  D  G  S  I   132
CGGCCCGAGGAGCTGCTGCAAATGGAGCTGCTCCTGGTGAACAAGCTCAAGTGGAACCTG   600
 R  P  E  E  L  L  Q  M  E  L  L  L  V  N  K  L  K  W  N  L   152

GCCGCAATGACCCCGCACGATTTCATTGAACACTTCCTCTCCAAAATGCCAGAGGCGGAG   660
 A  A  M  T  P  H  D  F  I  E  H  F  L  S  K  M  P  E  A  E   172
GAGAACAAACAGATCATCCGCAAACACGCCAGACCTTGTTGCCTCTTGTGCCACAGAT   720
 E  N  K  Q  I  I  R  K  H  A  Q  T  F  V  A  L  C  A  T  D   192
```

FIG. 2A

```
GTGAAGTTCATTTCCAATCCGCCCTCCATGGTGGCAGCGGGGGACCGTGTGGCCGCAGTG    780
 V  K  F  I  S  N  P  P  S  M  V  A  A  G  S  V  V  A  A  V     212
CAAGGCCTGAACCTGAGGAGCCCCAACAACTTCCTGTCCTACTACCGCCTCACACGCTTC    840
 Q  G  L  N  L  R  S  P  N  N  F  L  S  Y  Y  R  L  T  R  F     232

CTCTCCAGAGTGATCAAGTGTGACCCAGACTGCCTCCGGGCCTGCCAGGAGCAGATCGAA    900
 L  S  R  V  I  K  C  D  P  D  C  L  R  A  C  Q  E  Q  I  E     252
GCCCTGCTGGAGTCAAGCCTGCGCCAGGCCCAGCAGAACATGGACCCCAAGGCCGCCGAG    960
 A  L  L  E  S  S  L  R  Q  A  Q  Q  N  M  D  P  K  A  A  E     272

GAGGAGGAAGAGGAGGAGGAGGTGGACCTGGCTTGCACACCGACTGACGTGCCGGAC    1020
 E  E  E  E  E  E  E  V  D  L  A  C  T  P  T  D  V  R  D        292
GTGGACATCTGAGGGCCCAGGCGCCCACCCGCAGCGCCGAGGGCGGAGC              1080
 V  D  I  *  (SEQ ID NO. 2)

CGGCCCCCAGTTGCTCCACATGACAGTCCCTCCTCCTCCGGAGCATTTGATACCAGAAGGG    1140
AAACCTTCATTCTTGTTGTTGGTTGTTCTTTTTCCTTTGCTCTTTCCCCTTCCATCTC    1200

TGACTTAAGCAAAAGAAAAAGATTACCCAAAAACTGTCTTAAAGAGAGAGAGAAAA        1260
AAAAAAAAAAAAAAAAAAAAAAAAAAAAAAAAAAAAAAAAAAAAAAAAAAAAAAAAAAAA    1320

AAAAA 1325 (SEQ ID NO. 1)
```

FIG. 2B

```
GAATTCCCGCCGGGCTTGCCATGAGCTGTCTGCCACGAGTGGACCCGTCCGCAGG              60
                 M  E  L  C  H  E  V  D  P  V  R  R
GCCGTGCGGGACCGCCAACTGCTCCGAGACGACCGCCGTCCTGCAGAACCTGCTCACCATC       120
 A  V  R  D  R  N  L  L  R  D  D  R  V  L  Q  N  L  L  T  I          33

GAGGAGCGCTACCTTCCGCAGTGCTCCTACTTCAAGTGCGTGCAGAAGGACATCCAACCC        180
 E  E  R  Y  L  P  Q  C  S  Y  F  K  C  V  Q  K  D  I  Q  P          53
TACATGCGCAGAATGGTGGCCACCTGGATGCTGGAGGTCTGTCAGGAACAGAAGTGCGAA        240
 Y  M  R  R  M  V  A  T  W  M  L  E  V  C  Q  E  Q  K  C  E          73

GAAGAGGTCTTCCCCTGGCCATGAATTACCTGGACCGTTTCTTGGCTGGGGTCCCGACT         300
 E  E  V  F  P  L  A  M  N  Y  L  D  R  F  L  A  G  V  P  T          93
CCGAAGTCCCATCTGCAACTGCTGGGTGCTGTCTGCATGTTCCTGGCCTCCAAACTCAAA       360
 P  K  S  H  L  Q  L  L  G  A  V  C  M  F  L  A  S  K  L  K         113

GAGACCAGCCCGCTGACCGCGGAGAAGCTGTGCATTTACACCGACAACTCCATCAAGCCT       420
 E  T  S  P  L  T  A  E  K  L  C  I  Y  T  D  N  S  I  K  P         133
CAGGAGCTGCTGGAGTGGGAACTGGTGGTGCTGGGGAAGTTGAAGTGGAACCTGGCAGCT       480
 Q  E  L  L  E  W  E  L  V  V  L  G  K  L  K  W  N  L  A  A         153

GTCACTCCCTCATGACTTCATTGAGCACATCTTGCGCAAGCTGCCCCAGCAGCGGGAGAAG      540
 V  T  P  H  D  F  I  E  H  I  L  R  K  L  P  Q  Q  R  E  K         173
CTGTCTCTGATCCGCAAGCATGCTCAGACCTTCATTGCTCTGTGTGCCACCGACTTTAAG       600
 L  S  L  I  R  K  H  A  Q  T  F  I  A  L  C  A  T  D  F  K         193

TTTGCCATGTACCCACCGTCGATGATCGCAACTGGAAGTGTGGGAGCAGCCATCTGTGGG       660
 F  A  M  Y  P  P  S  M  I  A  T  G  S  V  G  A  A  I  C  G         213
CTCCAGCAGGATGAGGAAGTGAGCTCGCTCACTTGTGATGCCCTGACTGAGCTGCTGGCT       720
 L  Q  Q  D  E  E  V  S  S  L  T  C  D  A  L  T  E  L  L  A         233
```

FIG. 3A

```
AAGATCACCAACACAGACGTGGATTGTCTCAAAGCTTGCCAGGAGCAGATTGAGGCGGTG    780
 K  I  T  N  T  D  V  D  C  L  K  A  C  Q  E  Q  I  E  A  V     253
CTCCTCAATAGCCTGCAGCAGTACCGTCAGGACCAAGACCAACGTGACGGATCCAAGTCGGAGGAT    840
 L  L  N  S  L  Q  Q  Y  R  Q  D  Q  R  D  G  S  K  S  E  D     273

GAACTGGACCAAGCCAGCACCCCTACAGACGTGCGGGATATCGACCTGTGAGGATGCCAG    900
 E  L  D  Q  A  S  T  P  T  D  V  R  D  I  D  L  *   290 (SEQ ID NO. 4)

GTTCTTGTGTTTAGGGTGAAACTTAAAAAAAAATTCTGCCCCACCTAGATCATATT    1020
TAAAGATCTTTTAGAAGTGAGAGAAAAAGTCCTACGAAAACGGAATAATAAAAGCATT    1080
TGGTGCCTATTGAAGTACAGCATAAGGGAATCCCTTGTATATGCGAACAGTTATTGTTT    1140
GATTATGAAAGTAATAGTAAAAATGCTTACAGGGAAACCTGCAGAGTAGTTAGAGAATA    1200
TGTATGCCTGCAATATGGGACCAAATTAGAGAGAGACTTTTTTTTCATGTTATGAGCTA    1260
GCACATACACCCCTGTAGTATAATTTCAAGGACTGTGTACGCCATTTATCGATGATT     1320
AGATTGCAAAGCAATGAACTCAAGAAGAATTGAAATAAGGAGGACATGATGGGAAGG     1380
AGTACAAAACAATTCTCAACATGATTGGGATGGAGAAGCACCTTTGCTCT            1440
CAGCCACCTGTTACTAAGTCAGGAGTGTAGTTGGATCTCTACATTAATGTCCTCTTGCTG  1500
TCTACAGTAGCTGCTACCTAAAAAAAGATGTTTTATTTTGCCAGTTGGACACAGGTGATT  1560
GGCTCCTGGTTCATGTTCGTGACATCCTGCTCTTCCAAATGCAGTTCAGTTCATTGCA    1620
GACACCACCATATTGCTATCTAATGGGAAATGTAGCTATGGGCCATAACCAAAACTCAC   1680
ATGAAACGGAGGCAGATGTAATGTGGCCTTGGCCATTTCTTCTTAGAAAAAACTAATTTTGG 1740
GTATTTAAAGGGTAATGTGGCCTTGGCCATTTCTTCTTAGAAAAACTAATTTTTGGTG   1800
CTGATTGGCATGTCTGGTTCACAGTTTAGCATTGTTATAAACCATTCCATTCGAAAAGCA 1860
CTTTGAAAATTGTTCCCGAGCGATAGATGGGATGTTATGCAGGAATTC  1911
(SEQ ID NO. 3)
```

FIG. 3B

```
GAATTCCGATCCCCAGCCCCGCCCGCCGCTCTCCGCCTGCCTTGGGACTC                      60
GCGAGCCCGCACTCCCGCCTGCCTGTTGCGCTGCCCGAGTATGGAGCTGCTGTGTTGCGA           120
                                    M  E  L  L  C  C  E                 7
AGGCACCCGGCACGCGCCCCCGGGCCCGGACCCCGGCGCTGCTGGGGACCAGCCGTGT             180
 G  T  R  H  A  P  R  A  G  P  D  P  R  L  L  G  D  Q  R  V            27
CCTGCAGAGCCTGCTCCGCCTGGAGGAGCGCTACGTACCCCGCGCCTCCTACTTCCAGTG           240
 L  Q  S  L  L  R  L  E  E  R  Y  V  P  R  A  S  Y  F  Q  C            47
CGTGCAGCGGGAGATCAAGCCGCACATGCGGAAGATGCTGGCTTACTGGATGCTGGAGGT           300
 V  Q  R  E  I  K  P  H  M  R  K  M  L  A  Y  W  M  L  E  V            67
ATGTGAGGAGCAGCGCTGTGAGGAGGAAGTCTTCCCCCTGGCCATGAACTACCTGGATCG           360
 C  E  E  Q  R  C  E  E  E  V  F  P  L  A  M  N  Y  L  D  R            87
CTACCTGTCTTGCGTCCCCACCCGAAAGGCGCAGTTGCAGCTCCTGGGTGCGGTCTGCAT           420
 Y  L  S  C  V  P  T  R  K  A  Q  L  Q  L  L  G  A  V  C  M           107
GCTGCTGGCCCTCCAAGCTGCGGAGACCTGCGCGAGACCACGCCCCTGACCATCGAAAAACTGTGCATCTA 480
 L  L  A  S  K  L  R  E  T  T  P  L  T  I  E  K  L  C  I  Y          127
CACCGACCACGCTGTCTCTCCCCGCCAGTTGCGGGACTGGGAGGTGCTGGTCTGTAGGGAA          540
 T  D  H  A  V  S  P  R  Q  L  R  D  W  E  V  L  V  L  G  K          147
GCTCAAGTGGGACCTGGCTGCTGTGATTGCACATGATTTCCTGGCCTTCATTCTGCACCG          600
 L  K  W  D  L  A  A  V  I  A  H  D  F  L  A  F  I  L  H  R         167
GCTCTCTCTGCCCCGTGACCGACAGGCCCTTGTCAAAAAGCATGCCCAGACCTTTTTGGC          660
 L  S  L  P  R  D  R  Q  A  L  V  K  K  H  A  Q  T  F  L  A         187
CCTCTGTGCTACAGATTATACCTTTGCCATGTACCCGCCATCCATGATCGCCACGGGCAG          720
 L  C  A  T  D  Y  T  F  A  M  Y  P  P  S  M  I  A  T  G  S         207

FIG. 4A
```

```
CATTGGGGCTGCAGTGCAAGGCCTGGGTGCTGCTCCATGTCCGGGGATGAGCTCACAGA        780
  I  G  A  A  V  Q  G  L  G  A  C  S  M  S  G  D  E  L  T  E        227
GCTGCTGGCAGGGATCACTGGCACTGAAGTGGACTGCCTGCGGGCCTGTCAGGAGCAGAT        840
  L  L  A  G  I  T  G  T  E  V  D  C  L  R  A  C  Q  E  Q  I        247

CGAAGCTGCACTCAGGGAGAGCCTCAGGGAAGCCGCTCAGACAGCTCCAGCCCAGCGCC         900
  E  A  A  L  R  E  S  L  R  E  A  A  Q  T  S  S  P  A  P            267
CAAAGCCCCCCGGGGCTCCAGCAGCCAAGGCCCAGCCAGACCAGCCACTCCTACAGATGT        960
  K  A  P  R  G  S  S  S  Q  G  P  P  S  Q  T  S  T  P  T  D  V    287

CACAGCCATACACCTGTAGCCCTGAGAGGCCCCTCTGAGAGTGGCCACTAAGCAGAGAGG       1020
  T  A  I  H  L  *  292 (SEQ ID NO. 6)
GGCCGCTGCACCCACCTCCCTGCCTCCAGGAACCACACCACATCTAAGCCTGAAGGGGCG      1080

TCTGTTCCCCTTCACAAAGCCCAAGGATCTGGTCCTACCCATCCCGCAGTGTGCACT          1140
AAGGGGCCCGGCCAGCCATGTCTGCATTCGGTGCTAGTCAAGCTCCTCCTCCTGCAT          1200
CTGACCAGCAGCGCCTTTCCCAACTCTAGCTGGGGTGGCCAGGCTGATGGGACAGAAT         1260
TGGATACATACACCAGCATTCCTTTTGAACGCCCCACCCTGTGGGGCTCTCATGT            1320
TTTCAACTGCCAAAATGCTCTAGTGCCTTCTAAAGTGTTGTCCCTTCTAGGGTTATTGC        1380
ATTTGGATTGGGGTCCCTCTCAGTACTTTGGAGGCCCCTATGTAGTCCGTGCTGACAGCTGCTCC  1440
CTAGATGGCTCCTCTCAGTACTTTGGAGGCCCCTATGTAGTCCGTGCTGACAGCTGCTCC       1500
TAGAGGAGGGCCTAGGCTCAGCCAGAGAAGCTATAAATTCCTCTTTGCTTTGCTTTCT         1560
GCTCAGCTTCTCCTGTGATTGACAGTTTGCTGCTGAAGGCTCATTTTAATTTATTAA          1620
TTGCTTTGAGCACAACTTTAAGAGAGAGACGTAATGGGTCCTGGCCATCCCACAAGTGGTGG     1680
TAACCCTGGTGCTGTGTTTCCTCCCTCTGCTACTGCCCCTCCTCGGCAAAAGGATCTTGTGGCCA  1740
AGGAGCTGCTATAGCCTGGGGTGGGTCATGCAGGGATGCCCTGAGCCCTGTCTAGAGA         1800
TCCTCCAGGAGAAATGCAGCAGGTCTTTCCTAAGGCTGCAAGTTTAGGCTGTGGCCC          1860
GGGAGGCAAGCCTGTTGACACAGTGGCCTGTCTAATAAAGATGATTGTGGGAATTC     1962 (SEQ ID NO. 5)
```

| | |
|---|---|
| CYCD1-Hs | QLCCEVETIRRAYPDANLLNDRVLRAMLKAEETCAPSVSYFKCVQKEVLPSMRKIVATWMLEVCEEQKCEEVFPLAMNYLDRFL<br>SLEPVKKSRLQLLGATCMF |
| CYCA-Hs | SIVLEDEKPVSVNEVPDYHEDIHTYLR-EMEVKCKPKVGYMKKQP-DITNSMRAILVDWLVEVGEEYKLQNETLHLAVNYIDRFL<br>SSMSVLRGKLQLVGTAAML |
| CYCA-Dm | KELPPRNDRQRFLEVVQYQMDILEYFR-ESEKKHRPKPRYMRRQK-DISHNMRSILIDWLVEVSEEYKLDTETLYLSVFYLDRFL<br>SQMAVVRSKLQLVGTAAMY |
| CYCB1-Hs | VNDVDAEDGADPNLCSEYVKDIYAYLR-QLEEEQAVRPKYLLGR--EVTGNMRAILIDWLVQVQMKFRLLQETMYMTVSIIDRFM<br>QNNCVPKKMLQLVGTAMF |
| CDC13-Sp | WDDLDAEDWADPLMVSEYVVDIFEYLN-ELEIETMPSPTYMDRQ-KELAWKMRGILTDWLIEVHSRFRLLPETLFLAVNIIDRFL<br>SLRVCSLNKLQLVGIAALF |
| CLN1-Sc | IELSNAELLTHYETIQEYHEEISQNVL-VQSSKTKPDIKLIDQQPEMNPHQTREAIVTFLYQLSVMTRVSNGIFFHSVRFYDRYC<br>SKRVVLKDQAKLVVGTCLW |
| CLN3-Sc | PNLVKRELQAHHSAISEYNNDQLDHYF-RLSHTERPLYNL3NSQPQVNP-KMRFLIFDFIMYCHTRLNLSTSTLFLTFTILDKYS<br>SRFIIKSYNYQLLSLTALW |
| CYCD1-Hs | VASKMKETIPLTAEKLCIYTDGSIRPEELLQMELLLVNKLKWNLAAMTPHDFIEHFLSKMPEAEENKQIIRKHAQTFVALCATDV<br>KFISNPPSMVAAGSVVAAV (SEQ ID NO. 7) |
| CYCA-Hs | LASKFEEIYPPEVAEFVYITDDTYTKKQVLRMEHLVLKVLTFDLAAPTVNQFLTQ-YFLHQQ2NCKVESLAMFLGELSLIDAT--<br>PYLKYLPSVIAGAAFHLAL (SEQ ID NO. 8) |
| CYCA-Dm | IAAKYEEIYPPEVGEFVFLTDDSYTKAQVLRMEQVILKILSFDLCTPTAYVFINT-YAVLCDMPEKLKYMTLYISELSLMEGE--<br>TYLQYLPSLMSSASVALAR (SEQ ID NO. 9) |
| CYCB1-Hs | IASKYEEMYPPEIGDFAFVTDNTYTKHQIRQMEMKILRALNFGLGRPLPLKFLRR-ASKIGEVDVEQHTLAKYLMELTMLDYD--<br>-MVHFPPSQIAAGAFCLAL (SEQ ID NO. 10) |
| CDC13-Sp | IASKYEEVMCPSVQNFVYMADGGYDEEEILQAERYILRVLEFNLAYPNPMNFLRR-ISKADFYDIQTRTVAKYLVEIGLLDHK--<br>-LLPYPPSQQCAAAMYLAR (SEQ ID NO. 11) |
| CLN1-Sc | LAAKTWG25RLSELVHYCGGSDLFDESMFIQMERHILDTLNWDVYEPMINDYI (SEQ ID NO. 12) |
| CLN3-Sc | ISSKFWD3RMATLKVLQNLCCNQYSIKQFTTMEMHLFKSLDWSI2SATFDSYI (SEQ ID NO. 13) |

FIG. 5A

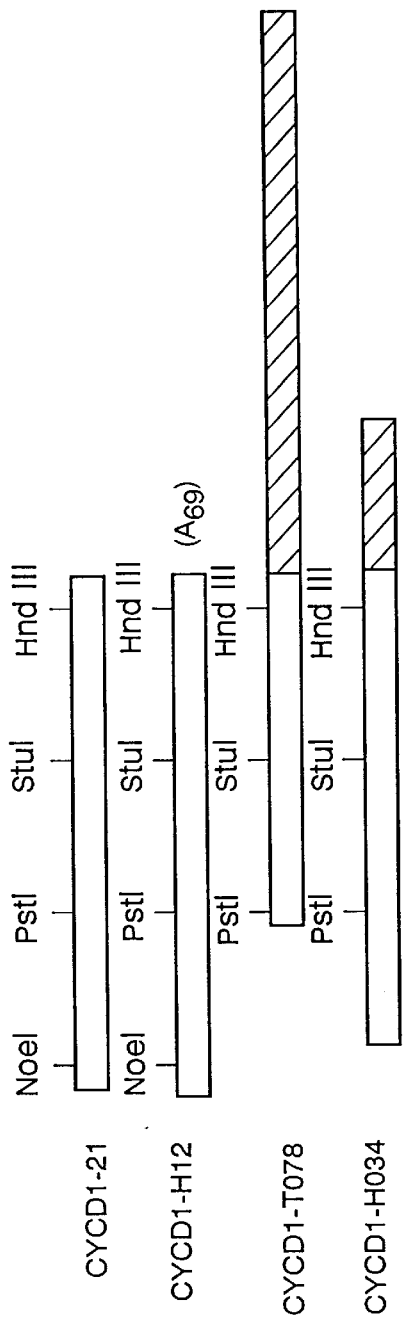

```
CYCD1-21   CCCAAAAACTGTCTTTXXXcDNAX(Glioblastoma)      (SEQ ID NO. 14)
CYCD1-H12  CCCAAAAACTGTCTTTAAAAGAGAGAGAGAGAGAGAGAG       cDNAX(HeLa)xxxxx(SEQ ID NO. 15)
CYCD1-H034 CCCAAAAACTGTCTTTAAAAGAGAGAGAGAGAGAGAGAGAGAAAAAAAAAATAGTATT
CYCD1-T078 CCCAAAAACTGTCTTTAAAAGAGAGAGAGAGAGAGAGAGAGAAAAAAAAA-TAGTATT
CYCD1-G068 CCCAAAAACTGTCTTTAAAAGAGAGAGAGAGAGAGAGAGAGAAAAAAAAAATAGTATT
CTCD1-H034 TGCATAACCCTGAGCGGTGGGGGAGGAGGGTT...              cDNAx(HeLa)xxSEQ ID NO. 16)
CYCD1-T078 TGCATAACCCTGAGCGGTGGGGGAGGAGGGTT...              cDNAx(Teratocarcinoma)xxxx(SEQ ID NO. 17)
CYCD1-G068 TGCATAACCCTGAGCGGTGGGGGAGGAGGGTT...              genomicx(liver)xx(SEQ ID NO. 18)
```

FIG. 6A

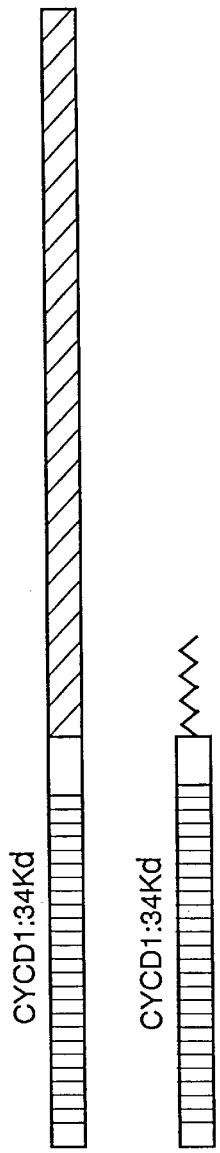

```
CYCD1-Hs  MEHQLLCCEVETI-RRAYPDANLL-NDRVLRAMLKAEETCAPSVSYFKCVQKEVLPS
CYL1-Mm   MENQLLCCEVETI-RRAYPDTNLL-NDRVLRAMLKTEETCAPSVSYFKCVQKEIVPS
CYCD2-Hs       MELLCHEVDPVRRAVRDRNLLR-DDRVLQNLLTIEERYLPQCSYFKCVQKDIQPY
CYL2-Mm
CYCD3-Hs       MELLCCEGTRHAPRAGPDPRLLGDQRVLQSLLRLEERYVPRASYFQCVQREIKPH
CYL3-Mm
CYCA-Hs
CYCB1-Hs
CYCB2-Hs
CYCC-Hs
CYCE-Hs
```

CYCLIN BOX

```
         HCND11   HCND12                                              HCND13
MRKIVATWMLEVCEEQKCEEEVFPLAMNYLDRFLSLEPVKKSRLQLLGATCMFVASKMKETIPLTAEKLCIYTDGSIRPEELLQMELLLVNKLKWNLAAMTPHDFI
MRKIVATWMLEVCEEQKCEEEVFPLAMNYLDRFLSLEPVKKSRLQLLGATCMFVASKMKETIPLTAEKLCIYTDGSIRPEELLQMELLLVNKLKWNLAAMTPHDFI
MRKIVATWMLEVCEEQKCEEEVFPLAMNYLDRFLSLEPLKKSRLQLLGATCMFVASKMKETIPLTAEKLCIYTDNSIRPEELLQMELLLVNKLKWNLAAMTPHDFI
MRRMVATWMLEVCEEQKCEEEVFPLAMNYLDRFLAGVPTPKSHLQLLGAVCMFLASKLKETSPLTAEKLCIYTDNSIKPQELLEWELVVLGKLKWNLAAVTPHDFI
MRRMVATWMLEVCEEQKCEEEVFPYLAMNYLDRFLAGVPTPKTHLQLLGAVCMFLASKLKETIPLTAEKLCIYTDNSVKPQELLEWELVVLGKLKWNLAAVTPHDFI
MRKMLAYWMLEVCEEQRCEEEVFPLAMNYLDRYLSCVPTRKAQLQLLGAVCMLLASKLRETTPLTIEKLCIYTDHAVSPRQLRDWEVLVLGKLKWDLAAVIAHDFL
MRKMLAYWMLEVCEEQRCEEDVFPLAMNYLDRYLSCVPTRKAQLQLLGTVCILLASKLRETTPLTIEKLCIYTDQAVAPWQLREWEVLVLGKLKWDLAAVIAHDFL
MRAILVDWLVEVGEEYKLQNETLHLAVNYIDRFLSSMSVLRGKLQLVGTAAMLLASKFEEIYPPEVAEFVYITDDTYTKKQVLRMEHIVLKVLTFDLAAPTVNQFL
MRAILIDMLVQVMKFRLLQETMYMTVSIIDRFMQNNCVPKKMLQIVGVTAMFIASKYEEMYPPEIGDFAFVTDNTYTKHQIRQMEMKILRALNFGLGRPLPLHFL
MRAILVDMLVQVHSKFRLLQETLYMCVGIMDRFLQVQPVSRKKLQLVGITALLLASKYEEMFSPNIEDFVYITDNAYTSSQIREMETLILKELKFELGRPLPLHFL
LQIFFTNVIQALGEHLKLRQQVIATATVYFKRFYARYSLKSIDPVLMAPTCVFLASKVEE16LKTRFSYAFPKEFPYRMNHILECEFYLLELMDCCLIVYHPYRPL
MRAILLDWLMEVCEVYKLHRETFYLAQDFFDRYMA2ENVVKTLLQLIGISSLFIAAKLEEIYPPKLHQFAYVTDGACSGDEILTMEIMMKALKWRLSPLTIVSWL
```

```
EHFLSKMPEAEENKQIIRKHAQTFVALCATDVKFISN  XXX(SEQ ID NO. 25)
EHFLSKMPEAEDNKQTIRKHAQTFVALCATDVKFISN  XXX(SEQ ID NO. 26)
EHILRKLPQQREKLSLIRKHAQTFIALCATDFKFAMY  XXX(SEQ ID NO. 27)
EHILRKLPQQKEKLSLIRKHAQTFIALCATDFKFAMY  XXX(SEQ ID NO. 28)
AFILHRLSLPRDRQALVKKHAQTFLALCATDYTFAMY  XXX(SEQ ID NO. 29)
ALILHRLSLPSDRQALVKKHAQTFLALCATDYTFAMY
```

FIG. 7C

CYCD1-Hs  PPSMVAAGSVVAAVQGLNLRSPNNFLSYYRLTRFLSRVIKCDPDCLRACQEQIEALLESSLRQAQQNMDPKA-AEEEEEEEVDLACTPTDVRDVDI*
(SEQ ID NO. 19)

CYL1-Mm   PPSMVAAGSMVAAMQGLNLGSPNNFLSRYRTTHFLSRVIKCDPDCLRACQEQIEALLESSLRQAQQNVDPKA-TEEEGEVEEEAGLACTPTDVRDVDI*
(SEQ ID NO. 20)

CYCD2-Hs  PPSMIATGSVGAAICGLQQDEEVSSLTCDALTELLAKITNTDVDCLKACQEQIEAVLLNSLQQYRQDQRD------GSKSEDELDQASTPTDVRDIDL*
(SEQ ID NO. 21)

CYL2-Mm   PPSMIATGSVGAAICGLQQDDEVNTLTCDALTELLAKITHTDVDCLKACQEQIEALLLNSLQQFRQEQHNA------GSKSVEDPDQATTPTDVRDVDL*
(SEQ ID NO. 22)

CYCD3-Hs  PPSMIATGSIGAAVQGLGACS-----MSGDELTELLAGITGTEVDCLRACQEQIEAALRESLREAAQTSSSPAPKAPRGSSSQGPSQTSTPTDVTAIHL*
(SEQ ID NO. 23)

CYL3-Mm   PPSMIATGSIGAAVIGLGACS-----MSADELTELLAGITGTEVDCLRACQEQIEAALRESLREAAQTAPSPVPKAPRGSSSQGPSQTSTPTDVTAIHL*
(SEQ ID NO. 24)

FIG. 7D

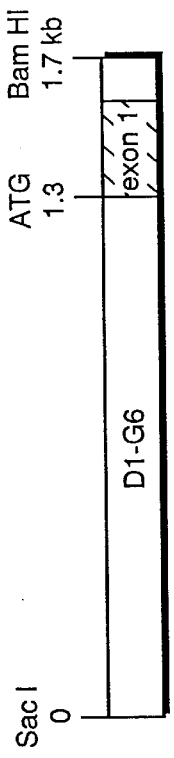
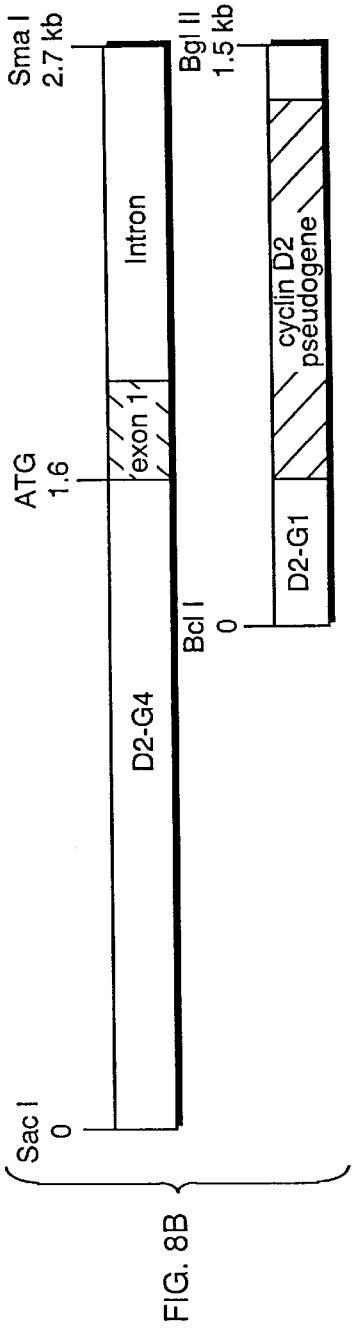
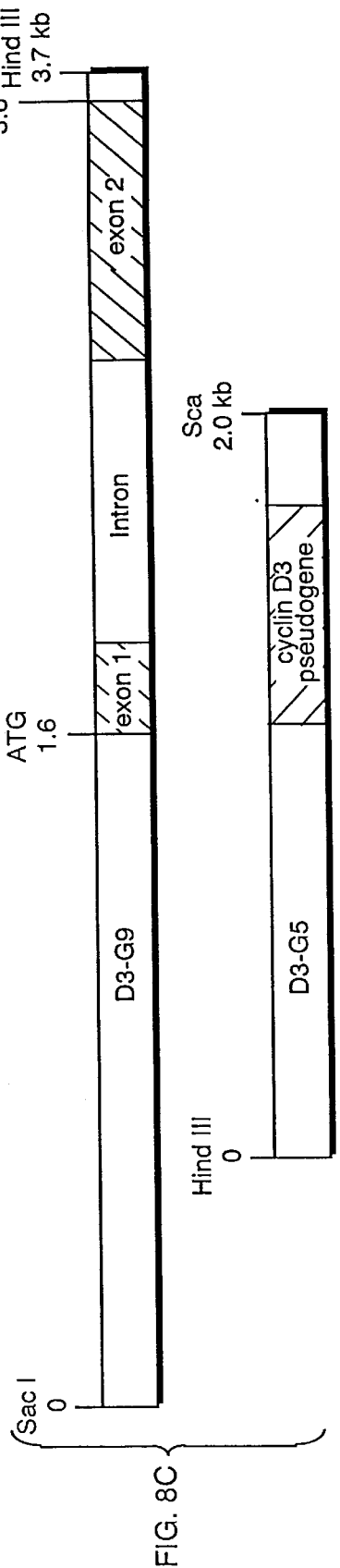
FIG. 8A
FIG. 8B
FIG. 8C

```
TGATCAAGTTGACACTCAATATTAACCCTCATAGACTGTGATCCCTATGTGCTGCCTTC      60
CCTCGTTTCTATTGCTTCTTTGGCCCCAAACCCAAATAAGGTTCCTTGGACACTAAGA      120
AGGAGGTGGAGTTGAAGGGAGGAGATGTGAGCGAGGCAGGCAGGGAAGCTCTGCTC        180
GCCCACTGCCAATCCTCACCTCTCCTAGAGAAGGATGAGGGGAATGCTTTTGCCTTCCC     240
CTCTGAAAACCCCTATTGAGCCAAAGGAGAGATGAGGGGAATGCTTTTGCCTTCCC        300
CTCCAAAACAAAAACAAAAACACACTTTTCCAGTCCAGAGAAAGCAGGGAGTGAG         360
GGGTCACAGAGCTGGCCATGCAGCTGCTGGGCTGTGAGGTAGACCCGTCCTCAGAGCCA     420
         M  Q  L  L  G  C  E  V  D  P  V  L  R  A
CGAGGGACTGCAACTACTCCAAGTTGACCGTGTCCTGAAGAACCTGCTTGCTATCAAGA     480
 T  R  D  C  N  L  L  Q  V  D  R  V  L  K  N  L  L  A  I  K

AAGCGCTACCTTCAGTAATGCTCCTACTTAAGTGTGTGCAGAAGGCCATCCAGCCCGTACA   540
 K  R  Y  L  Q  *  C  S  Y  F  K  C  V  Q  K  A  I  Q  P  Y
TGCACAGGATGGTGCCACTTCTGATGTGCCATTTGATTGGTGCCACTTCTGATGTGG       600
 M  H  R  M  V  P  L  L  M  V  (   insertion CCAACATGATTGAACCATTTGGGATGGAAAGCACCTTTACTCTCAGCCACCTGTTAACT    660
    insertion
AATGCTGGAGGTCTGTGAGGAACAGTGTGAAGAAGGTTTCCCTCTGGCCACGAT          720
 )  M  L  E  V  C  E  E  Q  K  C  E  E  K  V  F  P  L  A  T  I TTACCTGGACTGTTTCTTCGCCAGGATCCCAACTTCAAAGTCCCATCTGCAACTCCTGGG   780
 Y  L  D  C  F  F  A  R  I  P  T  S  K  S  H  L  Q  L  L  G
TGCTGTGTCGCATGTTCCTGGCCTCCAGCTCAAAGAGTCCAGCCCACTGACTGCCAAAAA    840
 A  V  C  M  F  L  A  S  R  L  K  E  S  S  P  L  T  A  K  K GCTGTGCATTTATACCGACAACTCCATCAAGCCTCAAGAGCTGCTGGAGTGGGAACTGGT    900
 L  C  I  Y  T  D  N  S  I  K  P  Q  E  L  L  E  W  E  L  V
GGTGTTGGGAAAGTTGAAGTGGAACCTGGCAGCTGTCACGCCTCATGACTTCATTTAGTA   960
 V  L  G  K  L  K  W  N  L  A  A  V  T  P  H  D  F  F  I  *  Y
```

FIG. 9A

```
CATCTTGCACAAGCTGCCCCAGCAGCGGGAGAAGCTGTCTCCAATCTGCAAGCAAGTCA                    1080
 I  L  H  K  L  P  Q  Q  R  E  K  L  S                   ( deletio
GAACTTCAATGCTCTGTATGCAATGTACCCGCCATCAATGGTTGCAACTGGAAGTGTAGG                    1140
 n       )  A  M  Y  P  P  S  M  V  A  T  G  S  V  G
AGCAGCTATCTGTGGACTTCAGCAACATGAGGAAGTGAGCTTACTCCCTTGCAATGCCCT                    1200
 A  A  I  C  G  L  Q  Q  H  E  E  V  S  S  L  P  C  N  A  L
GACTGAGCTGCTGGCAAAGATCACCAACACAGATGTGGATTGTCTCAAAAGCCAACCGGG                    1260
 T  E  L  L  A  K  I  T  N  T  D  V  D  C  L  K \ A  N  R
AGCATATTGAGGTGGTCTTCCTCAACAGCCTGCAGTGCCATCAGGACCAGCAGGACA                       1320
 E  H  I  E  V  V  F  L  N  S  L  Q  C  H  Q  D  Q  Q  D
GATCCAAGTCAGAGAGGATGAACTGGGCCAAGCAGCACCCCTATAGACCTGTGAGATATCGA                  1380
 R  S  K  S  E  D  E  L  G  Q  A\S  T  P  I  D  L  *  D  I  D
CCTGTGAGGATGGCCAGTCCAGCTGAGAGGCGCATTCATAATCTGCTGTCCTTCTTTCT                     1440
 XXLXX*XX(SEQ ID NO. 31)
GGTTATGTTTGTTCTTTGTATCTTAGGGCGAAACTTAAAAAAAAAAACCTCTGCCCCCA

CATAGTTCGTGTTTAAAGATCT  1462 (SEQ ID NO. 30)
```

FIG. 9B

```
AAGCTTCCAGATTAGAAAGAAAAAATAAAACTATCTTTATTTGCAGATGACATGATCGG           60
TCCATTCTCATGCTGCTTATAAAGACATACCCAAGACTGGATAATTTATAAAGGAAAGAG         120
GTTTGGCTCACAGTTCCCCATGGTGGAGAGGCCTCACAATCATGGCGAAAGAGCAAGGA          180
GCATCTCACATGGCAGCAGGAAGAAAAGAAGAATGAGAGGCCACGCCAGAGGGAAACCCTTA       240
TAAAATCATCAGATCTGAGAGACTTATTCACTGTCAGGAGAACAGTATGGAGGAAACGC          300
CCTTATGATTCAATTATCTCGCACTGTGTTCCTCCCACACACACATGGGAATTATGGAGC         360
TACAATTCAAGATGAGATTGGGTGGAGACACAGCCAAACCATATCAATCTTTTTTTCT           420
TATTCTTTTTTTTTTTTTTTTTTTGAGATGGAGTCCCACTCTGTTATCTAGGCTGG             480
AGTGCAGTGGTGTGATCTTGGCTCACTGCAACCTCAGCCTCCCAGGTTCAAGCGATTC           540
TCCTGCCCTGAGACTCCTGAATAGCTGAAATTACAGGCACCTGCCACTACGCCTGGCAAAT        600
ATTTTTGTTTGTTTGTTTGTTTGTTTGTTTGTTTTGAGACAGAGTCTCTCTCTGTCGCC          660
CAGGCTGGAGTGCAGTGGCGCGATCTCAGCTCACTGCAAACTCTGCCTCCCGGGTTCAAG         720
CCATTCCCTGCCTCAGCTCCCAAGTAGCTGGGACTACAGGCGCCCACCACCACCATGCC          780
AGCCTAATTTTTGTATTTTAGTAGAGACAGGGTTTCACCGTGTTAGCCAGGATGGTCT           840
CAATCTCCTGACCTCGTGATCCGCCCACCTCGGCCTCCCAAAGTGCTGGGATTACAGGCG         900
TGAGCCACTACGCCCAACCTATCAATCTTGTATATAGAAAAACCTAAGAATCTAGAAA           960
AAAACCCTATTATAACTAATAATAATAATCTGCAAAGTTGTAGACTATGAGATCAATA          1020
TACAAAAATTAACTCAATTTCTTTACATGTACAATGAATAACCCCAAAACAAAACTGGGA        1080
ATATAATTCTATTTTTAATAGTATCACAAAGAATGACAATACTTAGAAACAAATGATGGG        1140

CGCTAGCTTGCACTCCCGCCCTGCCTGTGCCGAGTGTGGAGCTGCTATGCTGCG              1200
A  L  A  C  T  P  A  L  P  V  R  C  P  S  V  E  L  L  C  C
                                                    *  W

AAGGCTCGAGAGACCCGCAGACGCCAGGGGATCAGCGCGTCCTGCAGAGCTTGCTCCCCTT      1260
E  G  S  R/D  P  Q  T  P  G  D  Q  R  V  L  Q  S  L  L  P  L
GGAGTAGCGCTGCGTGCACTGCGCCTACTTCCAGTGCGTGCAAAGGGAGAGCAAGCCGCA       1320
E  *  R  C  V  H  C  A  Y  P  Q  C  V  Q  R  E  S  K  P  H

FIG. 10A
```

```
CATGCGGAAGATGCTGGTTACTGGATGCTGGAGGTGTGTGAGGAGCAGTGCTGTGAGGA    1380
 M  R  K  M  L  V  Y  W  M  L  E  V  C  E  E  Q  C  C  E  E
GGAGCAGTGCTGTAAGGAGGAAGTCTTTCCCTGGCCATGAACCACCTGCATGCTACCTG    1440
 E  Q  C  C  K  E  E  V  F  P  L  A  M  N  H  L  H  A  T  C
TCCTACGTCCCCACCCACCCGAAAGCACAGTTGCAGCTCTTGGTTGCGGTCTCCATGCG    1500
 P  T  S  P  P  T  R  K  A  Q  L  Q  L  L  V  A  V  S  M  R
GCTGGCCTCCAAGCTGCGTAAGACTGGGCCCATGACCATTGAGAAAATGTGCATCTACAC    1560
 L  A  S  K  L  R  K  T  G  P  M  T  I  E  K  M  C  I  Y  T
CGACCACGCTGTCTCTCCCTGCCAGTTGCGGGACTGGGAGGTGATGGTCCTGGGAAGCT    1620
 D  H  A  V  S  P  C  Q  L  R  D  W  E  V  M  V  L  G  K  L
CAAATGGACCTGGCCGCGTGTGATTGCTCATGACTTCTTGGCCCTCATTCTGCACCGACC    1680
 K  W  D  L  A  A  V  I  A  H  D  F  L  A  L  I  L  H  R  \
GACAGGCCTTGGTCAAAAAGCATGCCCAGATCTTTTTGGCTGTCTGTGCTACAGATTACA    1740
 R  Q  A  L  V  K  K  H  A  Q  I  F  L  A  V  C  A  T  D  Y
CCTTTGCCATGTACCCACCATCCAGTTGTGAAAACAACCCAAATGCCTGTTAACTGATGA    1800
 T  F  A  M  Y  P  P  S  S  C  E  N  N  P  N  A  C  *
(SEQ. ID NO. 33)
ACAGATAACCATATGTGATATATATATCAATACAATGGAATAATGGCCTGCATGCTGCTTA    1860
CGCTGTAATCCTGCACTTTGGGAGGCCAAAGTGAGGATCACTTGAGCCGAGGAGTTCAA    1920
GGCCAGCCTGGGCACAAAGTGAGACTCCTTCTAAAAAATAAAATAAAATAAAAAAATAAA    1980
AACAATGTAATATTATTCAGCCATAGAAAGGAATAAAGTACT    2021
(SEQ. ID NO. 32)
```

FIG. 10B

```
GAGCTCGATCAGTACACTCGTTTGTTTAATTGATAATTGTCCTGAATTATGCCGGCTCCT
GCAGCCCCCTCACGCTCACGAATTCAGTCCCAGGGCAAATTCTAAAGGTGAAGGGACGTC
TACACCCCCAACAAAACCAATTAGGAACCTTCGGTGGGTCTTGTCCCAGGCAGAGGGGAC
TAATATTTCCAGCAATTTAATTTCTTTTTAATTAAAAAAAATGAGTCAGAATGGAGATC
ACTGTTTCTCAGCTTTCCATTCAGAGTGTGTTTCTCCCGTTAAATTGCCGGCACGGGA
AGGGAGGGGTGCAGTTGGGACCCCCGCAAGGACCGACTGGTCAAGGTAGGAAGGCAGC
CCGAAGAGTCTCCAGGCTAGAAGGACAAGATGAAGAAATGCTGGCCACCATCTTGGCT
GCTGCTGGAATTTTCGGGCATTTATTTTATTTTTGAGCGAGCCATGCTAAGCT
GAAATCCCTTAACTTTTAGTTAGTTACCCCCTGGGCATTTGCAACGACGCCCCTGTGCCCG
GAATGAAACTGCACAGGGTTGTGTGCCCGGTCCTCCCCCGTCCTTGCATGCTAAATTAG
TTCTTGCAATTTACACGTGTTAATGAAAATGAAAAGAAGATGCAGTCGCTGAGATTCTTTG
GCCGTCTGTCCGCCCGTGGGGTGCCGCCGCCCGCCCCAGTCACCCTCTGAAATGCGCCATTCTGCCGG
CTTGGATATGGGGTGTCGCCGCCCTTCCTAGTTGTCCCCTACTGTCCCCTGCAGAGCCACCTCACCTCACCCCTAAA
TGCTGGCCGGCCCTTCCTAGTTGTCCCCTACTGTCCCCTGCAGAGCCACCTCACCTCACCCCTAAA
TCCCGGGACCCACTCGAGGCGACGGCCCCCTGCACCCCTCTCGGCGGGAGAAAGGCT
GCAGCGGGGCGATTTGCATTTCTATGAAAACCGGACTACAGGGCAACTGCCCGCAGGGC
AGCGGCGGCGCCTCAGGGATGCTTTTCGTCTGCCCCCTCGCTGCTCCCGGCGTTCTGCCCG
CGCCCCCGCCCCCGCCGCCCCCCCCTCCCGCCCTCCCATTCTCTGCGGCTTT
GATCTTTGCTTAACAACAGTAACGTCACACGGACTACAGGGAGTTTTGTTGAAGTTGCA
AAGTCCTGGAGCCTCCAGAGGGCTGTGCGGGCGTGTGCCGCAGTAGCAGCAGAGTCCGCACG
CTCCGGCGAGGGCAGAAGAGCGCGAGGAGCCGGCAGAAGCGAGAGCCGAGCG
CGGACCCAGCCAGGACCCCACACCCTCCCCAGCTGCCCAGGAAGAGCCCCAGCCATG (SEQ ID No. 34)
```

GAGCTCGAGCCACGCCATGCCCGCTGCACGTGCCAGCTTGGCCAGCACATCAGGGCGCTG
GTCTCTCCCCTTCCTCCTGGAGTGAAATACACCAAAGGGCGCGTGGGGTGGGGGGTGA
CGGGAGGAAGGAGGTGAAGAAACGCCACCAGATCGTATCTCCTGTAAAGACAGCCTTGAC
TCAAGGATGCGTTAGAGCACGTGTCAGGGCCGACCGTGCTGGGCGGCGACTTCACCGCAGT
CGGCTCCCAGGGAGAAAGCCTGGCGAGTGAGGCCCTCATGCTCCGGGAAACCGAGGGGTCGGCGAGGATG
CGGGCGAAGGACCGAGCGTGGAGGGGAGCCGAGCCGACCTAATCCCTTCACTCGCCCCTTCCCTCCCG
TGCGCAGGGGGAGCGAGGGGAGCCGACCTAATCCCTTCACTCGCCCCCTTCCCTCCCG
GGCCATTTCCTAGAAAGCTGCATCGTGTGCCACGCTCAGCGCAGACACCTCGGGCGGC
TTGTCAGCAGATGCAGGGGGCGAGGAAGCCGGGTTTTTCCGTGGCCGCTGGCCGCTGCGGGG
AACCGCTGGGAGCCCTGCCCCCCGGCCTGCGGCGGCCCTAGAGCGCTGCACCGCGTCGCCCC
ACGGCGCCCGAAGAGCCCCAGAAACACGATGGTTTCTGCTCGAGGATCACATTCTATCC
CTCCAGAGAAGCACCCCCCCTTCCTTCCTAATACCCACCACCTCTCCTCCTCCTTCCTCT
GCACACACTCTGCAGGGGGCAGAAGGACGTTGTTCTGGTCCCTTAATCGGGGCTT
TCGAAACAGCTTCGAAGTTATCAGGAACACAGACTTCAGGGACATGACCTTTATCCTCTGG
GTATGCGAGGTTGCTATTTTCTAAAATCACCCCCCTATTTTCACTTAAGGACCT
ATTTCTAAATTGTCTGAGGTCACCCATCTGCGTTTTGAAGAAGCCAAAGTTGGAGGGTCGT
TAAATACAAGGCAGGAGATTAGGATCGTTTTGAAGAATAGAGGCCAGAAATAGGAGTCGGTA
ATTTGGCGTGCTACACCTACAGAATGAGTGAAATTAGAGGCCAGCTTGATGAGGGAGAGG
GTTTTTTTGTGGGTTGCCCTGTCCGGCCATGCAGGCTTCGGGCCAGCTGCTGTTCTCCTTAA
GTTGGGGGTTGCGGGGACCGCGTTTGAAGTTGGGTCGGGCCAGCTGCTGTTCTCCTTAA
TAACGAGAGGGAAAAGGGGAGGAGAACCAGAGCGGGAGCGGGAGAGAGCAGGGAGGACCGGG
AGGGGAGGAAAAGGGGAGGAGAACCAGAGCGGGAGCGGGAGAGAGCAGGGAGGAGAGCTAA
CTGCCCAGCCAGCTTCGGTCACGCTTCAGACGGAGCGGAGAAGAGCGAGCAGGGAGAGCGAGA
CCAGTTTAAGGGAGGACCGGTGCGAGTGAGGCAGCCCCTAGGCTCTGCTCGCCCACCA
CCCAATCCTCGCCTCCCTTCTGCTCCACCTTCTCTCTGCCCTCACCTCTCCCCCGAAA
ACCCCCTATTTAGCAACAGAAAAACCCTTTCCAGGCCGGGAAAGCAGGAGGGAAAGCGCCGGGCTGC
CATG (SEQ ID No. 35)

```
GAGCTCCCGTCCCCATACTACAGGTTCACATCCAGCTTTCAGGACTAGTCAGTCTATGTG
GCCCTCCCTCAATTAATAAATCAGCAACTAATTTGCCAGGTGCGGTGGTTTGTGCCTGTA
ATCCCAGCACTTTAGGAAGCTGAGGCAGGCAGATCACTTGAGGTCAGGAGTTCGAGACCA
GCCTGGCCAACATGGTGAAATCCCGTATCTACTGAAAATACAAAAATTAGCCGGGCATGG
TGGTATGCACCCGTAATCCCAGCTACTCAGGAAGCTGAGGCAGGAGAATCACTTGAAACC
GGGAGGCAGAGGTTGCAGTAAGCTGCACTCCAGCCTGGTGACAAGAGCAAAACTTTGTGT
CAAAAAAACAAAGAAAACCAAAAAACAAAGGAAAACAGAAAAAACCCTTCTATTTGTTAA
AAAAAAAAAAATCCACCGTGAACCAAAAATTAGTAAAAACAATGAACTAAAATTTTGTTT
TTGCAAAATGTATGATAACAAAATGTTAAGGAAGGTCATGTGCCGTTATGGTTCACTGCA
GCCTTGAACTCCTGGGCTCAAGCGATCCTCCTGCTTCGGTCTCCCTAGTAGCTGGGACTA
CAGGCTTGTGCCACCGCACCCAGCTTATTTTTTTTTTTATTTTTTGTAGAGATAGGAGT
CTTGCTTTGTTGTCCAGGCTGGTCTTCAACTCCTAGCTTCCAGTGATCCTCCTGCCTCAG
CCTCCCAAGTGCTGGGCCTGATGGGACATTTTTATACATAGTGCCATGTACCTATAAATG
AGAAGTTTTAAAAATACTGATTTTAAAAATTAATTTATGTCAAGAATTTTTATACCAAAG
TTAAAAAACCAAACCGAAAATATGAAAAGGGTTAATATCTTTGAGAGGTGATGAGAACTT
ATAAGTCAATAAGAGAAAACAAACATCCCTATAAATGAATAAGCTAAGGACATGAATGGG
TAATGTACATAAGAAATGTAAATGTCTAGTAATATGCCAAAATAGATTTATTATTACTAA
TAAGCCACTTTCACTCTCTAGTTGGCAGAGTTGTTTTGAAAAATAGATATGTAATGATGG
TGGAAAAGATTGGTTTAACTATTCAGCAGGAAAATTTGGCAATTAGAAGTGTATCAAAAG
CCTTAGAATGTTTCATAACCTTAGATTGGGAAATTCCACTTCTAGAAATTAATTCACTTC
TAGAAATAATCATGAGTGTGCACAAGATATTACCACAAAATATTTTACAGTATTATGT
CTAATAGAGAAGAACTAGAAATAATTTAAATTTCCACCAATACAGGTTTGCCAAAATACA
TTTTGTACATTCACCTAATGGTATATTATGTCCCTATTACAAATTACGTCCTAGAATATT
TAATAGCATGGAAAAGTGTTAACAGTATTTTTTTAATGAAAAAAGCTTACAAAACAGTTT
GTGATGATTCCATTTAAAATGTGTGTTTATTCATAGAACAAAGATTAGAAAAATAAACAT
TGATATATTAAAGGGTTATTTCATGGCAAATTGCAAATGATTATTTCCTTTTTTTGTGGC
TTATTTGTATTTTTGAAGTTTTCTACAATGTAAAAGAATATTTTATGATATGAAAACTAC
AATACAATTTATAATATAAGAAAGAATAATTCGGCCGGGAACGGTGGCTCACGCCTGTAA
TCCCAGCACTTTTGGAGGCCGAGACCGGCGGATCACGAGGTCAGGGGTTCAAGACTAGCC
TGGCCAACATAGTGAAACCCCATCTCTACGAAAAATACAAAAATTAGTCAGGCATGGTGG
TGCGTGCCTGTAGTCCCAGCTACTCGGGAATTGCTTGAACCCGGGAGGTGGAGGTTGCAG
TGAGCCCAGATCGCACCACTGCACTCCAGCTTGAGCAACAGAGTAGACTTCGTCTCAAAA
AAAAAAAAAAAAAAAAAGAATAATTAACAGAAAATGGTTAGACACTTCCTTAGTGTCT
CCTAAGTCAGGAGGACCCCAGTAGGGCAGGGATCCTCATGGCCTCCTCCCATTTGGAGCA
TTATTGGAGGTCTTTTTCGGCCTCTTCGTCAAGTGGAATCTAGCTTCCGGTAAAACTACA
AAGTAACCAAAAGTTTGGGAGGTGGAAGAAATGCAACCGGTAGATCTCACAGAGTCTGTG
CAAGAAACTGATTCAATGAGAATCTAGTTTCTCCGTCCACAGTTTCTCCAAACAGAAACT
AAGGCCGACTTTAGGGGCTTGTCCAAACCTAGGCAAGCAACTTAACAAGGTGAGGCCATG
```

FIG. 13A

ACTCCATGGCCTTTCCGTTCTGTTATATGCTGACTTAGACTAAAGCTCTCATACTTTAAA
GTGCACAGAAATCTAGTTAAAATGCAGATTCTGATTCAGGTTAGGGGTGGGCCTGAGAGT
CTGCATTTCTAACCAGCTCCCAGGCGATGACCACGCACGGGACAGGTCTGGGATCACAGT
TTAACTAGCAATGGTGTAGAACACAGAATCTGCAGCAAGAAGGCCAGCTTCCCAATCCTA
GCTCTGCCACGGACCAACTGAATGACAGTTGCCTCGGTTTCCGAGTTTTCGTGAAGATGT
AGTGAGTCATTACATCGTGAGGCTTTCGAGCAGCGTTCACTAAGAACTAGCTCTGACATT
ATTTATCGCATTCCTTACAGCAAGCAGCCGGTGAAGTAGGGTTTGACGAATGAATAAGTG
AATGAATGACCTTTGGAGAAAAATTGTTTCCTGGGTGACTAGAGTCCGAGAAGCAAAATG
GGAGGGCCCGTGGTGGGTAGGAGGCCCACCTCCTAGAAAGTTCTCTGCACCCGGTGGTCC
AGAGGGCCTGGAGTGCCGGAAGCCGGCCGCGTTGCGCTCACGGCCCAATGGGGCCGCGGG
AGGGAGGGGAGAGCGCTCAGCCAACCCTTTCCGTTCCGGGCGCCGCAGCCCCGCCCCTCG
GAGCGTTGCGACGTCCGAGCATTCCACGGTTGCTACATCGTCGCGAGGGGGGCGCCTGT
CAGGGAAGCGGCGCGCGCGGGCGGCGGGCGGCTGGGGATCCGCCGCGCAGTGCCAGC
GCCAGCGCCAGACCCGCGCCCCGCGCTCTCCGGCCCGTCGCCTGTCTTGGGACTCGCGAG
CCCGCACTCCCGCCCTGCCTGTTCGCTGCCCGAGT<u>ATG</u> (SEQ ID No. 36)

FIG. 13B

| | | | | | | | | | | |
|---|---|---|---|---|---|---|---|---|---|---|
| CCT | GCC | GCC | GCG | ATG | CAG | AAA | TAC | GAG | AAA | CTG | GAA | AAG | ATT | GGG | GAA | GGC | ACC | 54 |
| | | | | M | Q | K | Y | E | K | L | E | K | I | G | E | G | T | 14 |

| TAC | GGA | ACT | GTG | TTC | AAG | GCC | AAA | AAC | CGG | GAG | ACT | CAT | GAG | ATC | GTG | GCT | CTA | 108 |
| Y | G | T | V | F | K | A | K | N | R | E | T | H | E | I | V | A | L | 32 |

| AAA | CGG | GTG | AGG | CTG | GAT | GAC | GAT | GAG | GGT | GTG | CCG | AGT | TCC | GCC | CTC | CGG | 162 |
| K | R | V | R | L | D | D | D | E | G | V | P | S | S | A | L | R | 50 |

| GAG | ATC | TGC | CTA | CTC | AAG | GAG | CTG | AAG | CAC | AAG | AAC | ATC | GTC | AGG | CTT | CAT | GAC | 216 |
| E | I | C | L | L | K | E | L | K | H | K | N | I | V | R | L | H | D | 68 |

| GTC | CTG | CAC | AGC | GAC | AAG | AAG | CTG | ACT | TTG | GTT | TTT | GAA | TTC | TGT | GAC | CAG | GAC | 270 |
| V | L | H | S | D | K | K | L | T | L | V | F | E | F | C | D | Q | D | 86 |

| CTG | AAG | AAG | TAT | TTT | GAC | AGT | TGC | AAT | GGT | GAC | CTC | GAT | CCT | GAG | ATT | GTA | AAG | 324 |
| L | K | K | Y | F | D | S | C | N | G | D | L | D | P | E | I | V | K | 104 |

| TCA | TTC | CTC | TTC | CAG | CTA | CTA | AAA | GGG | CTG | GGA | TTC | TGT | CAT | AGC | CGC | AAT | GTG | 378 |
| S | F | L | F | Q | L | L | K | G | L | G | F | C | H | S | R | N | V | 122 |

| CTA | CAC | AGG | GAC | CTG | AAG | CCC | CAG | AAC | CTA | CTA | ATA | AAC | AGG | AAT | GGG | GAG | CTG | 432 |
| L | H | R | D | L | K | P | Q | N | L | L | I | N | R | N | G | E | L | 148 |

| AAA | TTG | GCT | GAT | TTT | GGC | CTG | GCT | CGA | GCC | TTT | GGG | ATT | CCC | GTC | CGC | TGT | TAC | 486 |
| K | L | A | D | F | G | L | A | R | A | F | G | I | P | V | R | C | Y | 158 |

FIG. 14A

```
TCA GCT GAG GTG GTC ACA CTG TGG TAC CGC CCA CCG GAT GTC CTC TTT GGG GCC    540
 S   A   E   V   V   T   L   W   Y   R   P   P   D   V   L   F   G   A    176

AAG CTG TAC TCC ACG TCC ATC GAC ATG TGG TCA GCC GGC TGC ATC TTT GCA GAG    594
 K   L   Y   S   T   S   I   D   M   W   S   A   G   C   I   F   A   E    194

CTG GCC AAT GCT GGG CGG CCT CTT TTT CCC GGC AAT GAT GTC GAT GAC CAG TTG    648
 L   A   N   A   G   R   P   L   F   P   G   N   D   V   D   D   Q   L    212

AAG AGG ATC TTC CGA CTG CTG GGG ACG CCC ACC GAG GAG CAG TGG CCC TCT ATG    702
 K   R   I   F   R   L   L   G   T   P   T   E   E   Q   W   P   S   M    230

ACC AAG CTG CCA GAC TAT AAG CCC TAT CCG ATG TAC CCG GCC ACA ACA TCC CTG    756
 T   K   L   P   D   Y   K   P   Y   P   M   Y   P   A   T   T   S   L    248

GTG AAC GTC GTG CCC AAA CTC AAT GCC ACA GGG AGG AGC CTG CTG CAG AAC CTT    810
 V   N   V   V   P   K   L   N   A   T   G   R   S   L   L   Q   N   L    266

CTG AAG TGT AAC CCT GTC CAG CGT ATC TCA GCA GAA GAG GCC CTG CAG CAC CCC    864
 L   K   C   N   P   V   Q   R   I   S   A   E   E   A   L   Q   H   P    284

TAC TTC TCC GAC TTC TGT CCG CCC TAG GCC CGG GAC CCC CGG CCT CAG CTG GGC    918
 Y   F   S   D   F   C   P   P                                             292

CTG GCC TAT TTA AGC CCC TCT TGA GAG GGG TGA GAG GGG TGA GAC AGT GGG GGT GCC TGG TGC    972
GCT GTG CTC AGC AGT GCT GGG CCA GCC GGG GTG GGG TGC CTG AGC TGC CCG AGC TTC           1026
TCA CTC CCT TTG ACT TTG TGG AAT TTC ATA AAT TTA TTT AAT TTC CTT TCC CAC AAA           1080
AAA AAA AGG                                                                            1089
```

FIG. 14B

D-TYPE CYCLINS AND USES RELATED THERETO

RELATED APPLICATIONS

This application a Divisional of application Ser. No. 07/963,308 filed on Oct. 16, 1992, which is is a continuation-in-part of U.S. Ser. No. 07/888,178 filed May 26, 1992 and entitled "D-Type Cyclin and Uses Related Thereto", now abandoned, which corresponds to and claims priority to Patent Cooperation Treaty Application No. PCT/US92/04146, filed May 18, 1992 and entitled "D-Type Cyclin and Uses Related Thereto", and to U.S. Ser. No. 07/701,514, filed May 16, 1991 and entitled "D-Type Cyclin and Uses Related Thereto." The teachings of U.S. Ser. Nos. 07/888,178, 07/701,514 and the PCT Application are incorporated herein by reference.

FUNDING

Work described herein was supported by National Institutes of Health Grant GM39620 and the Howard Hughes Medical Institute. The United States Government has certain rights in the invention.

BACKGROUND OF THE INVENTION

A typical cell cycle of a eukaryotic cell includes the M phase, which includes nuclear division (mitosis) and cytoplasmic division or cytokinesis and interphase, which begins with the G1 phase, proceeds into the S phase and ends with the G2 phase, which continues until mitosis begins, initiating the next M phase. In the S phase, DNA replication and histone synthesis occurs, while in the G1 and G2 phases, no net DNA synthesis occurs, although damaged DNA can be repaired. There are several key changes which occur during the cell cycle, including a critical point in the G1 phase called the restriction point or start, beyond which a cell is committed to completing the S, G2 and M phases.

Onset of the M phase appears to be regulated by a common mechanism in all eukaryotic cells. A key element of this mechanism is the protein kinase p34$^{cdc2}$, whose activation requires changes in phosphorylation and interaction with proteins referred to as cyclins, which also have an ongoing role in the M phase after activation.

Cyclins are proteins that were discovered due to their intense synthesis following the fertilization of marine invertebrate eggs (Rosenthal, E. T. et al., *Cell* 20:487–494 (1980)). It was subsequently observed that the abundance of two types of cyclin, A and B, oscillated during the early cleavage divisions due to abrupt proteolytic degradation of the polypeptides at mitosis and thus, they derived their name (Evans, T. et al., Cell 33:389–396 (1983); Swenson, K. I. et al., *Cell* 47:867–870 (1986); Standart, N. et al., *Dev. Biol.* 124:248–258 (1987)).

Active rather than passive involvement of cyclins in regulation of cell division became apparent with the observation that a clam cyclin mRNA could cause activation of frog oocytes and entry of these cells into M phase (Swenson, K. I. et al., *Cell* 7:867–870 (1986)). Activation of frog oocytes is associated with elaboration of an M phase inducing factor known as MPF (Masui, Y. and C. L. Markert, *J. Exp. Zool.* 177:129–146 (1971); Smith, L. D. and R. E. Ecker, *Dev. Biol.* 25:232–247 (1971)). MPF is a protein kinase in which the catalytic subunit is the frog homolog of the cdc2 protein kinase (Dunphy, W. G. et al., *Cell* 54:423–431 (1988); Gautier, J. et al., *Cell* 54:433–439 (1988); Arion, D. et al., *Cell* 55:371–378 (1988)).

Three types of classes of cyclins have been identified to date: B, A and CLN cyclins. The B-type cyclin has been shown to act in mitosis by serving as an integral subunit of the cdc2 protein kinase (Booher, R. and D. Beach, *EMBO J.* 6:3441–3447 (1987); Draetta, G. et al., *Cell* 56:829–838 (1989); Labbe, J. C. et al., *Cell* 57:253–263 (1989); Labbe, J. C. et al., *EMBO J.* 8:3053–3058 (1989); Meier, L. et al., *EMBO J.* 8:2275–2282 (1989); Gautier, J. et al., *Cell* 60:487–494 (1990)). The A-type cyclin also independently associates with the cdc2 kinase, forming an enzyme that appears to act earlier in the division cycle than mitosis (Draetta, G. et al., *Cell* 56:829–838 (1989); Minshull, J. et al., *EMBO J.* 9:2865–2875 (1990); Giordano, A. et al., *Cell* 58:981–990 (1989); Pines, J. and T. Hunter, *Nature* 346:760–763 (1990)). The functional difference between these two classes of cyclins is not yet fully understood.

Cellular and molecular studies of cyclins in invertebrate and vertebrate embryos have been accompanied by genetic studies, particularly in ascomycete yeasts. In the fission yeast, the cdc13 gene encodes a B-type cyclin that acts in cooperation with cdc2 to regulate entry into mitosis (Booher, R. and D. Beach, *EMBO J.*, 6:3441–3447 (1987); Booher, R. and D. Beach, *EMBO J.* 7:2321–2327 (1988); Hagan, I. et al., *J. Cell Sci.* 91:587–595 (1988); Solomon, M., *Cell* 54:738–740 (1988); Goebl, M. and B. Byers, *Cell* 54:433–439 (1988); Booher, R. N. et al., *Cell* 58:485–497 (1989)).

Genetic studies in both the budding yeast and fission yeast have revealed that cdc2 (or CDC28 in budding yeast) acts at two independent points in the cell cycle: mitosis and the so-called cell cycle "start" (Hartwell, L. H., *J. Mol. Biol.*, 104:803–817 (1971); Nurse, P. and Y. Bissett, *Nature* 292:558–560 (1981); Piggot, J. R. et al., *Nature* 298:391–393 (1982); Reed, S. I. and C. Wittenberg, *Proc. Nat. Acad. Sci. USA* 87:5697–5701 (1990)).

In budding yeast, the start function of the CDC28 protein also requires association of the catalytic subunit of the protein kinase with ancillary proteins that are structurally related to A and B-type cyclins. This third class of cyclin has been called the Cln class, and three genes comprising a partially redundant gene family have been described (Nash, R. et al., *EMBO J.* 7:4335–4346 (1988); Hadwiger, J. A. et al., *Proc. Natl. Acad. Sci. USA* 86:6255–6259 (1989); Richardson, H. E. et al., *Cell* 59:1127–1133 (1989)). The CLN genes are essential for execution of start and in their absence, cells become arrested in the G1 phase of the cell cycle. The CLN1 and CLN2 transcripts oscillate in abundance through the cell cycle, but the CLN3 transcript does not. In addition, the CLN2 protein has been shown to oscillate in parallel with its mRNA (Nash, R. et al., *EMBO J.* 7:4335–4346 (1988); Cross, F. R., *Mol. Cell. Biol.* 8:4675–4684 (1988); Richardson, H. E. et al., *Cell* 59:1127–1133 (1988); Wittenberg, et al., 1990)).

Although the precise biochemical properties conferred on cdc2/CDC28 by association with different cyclins have not been fully elaborated, genetic studies of cyclin mutants clearly establishes that they confer "G1" and "G2" properties on the catalytic subunit (Booher, R. and D. Beach, *EMBO J.* 6:3441–3447 (1987); Nash, R. et al., *EMBO J.* 7:4335–4346 (1988); Richardson, H. E. et al., *Cell* 56:1127–1133 (1989)).

cdc2 and cyclins have been found not only in embryos and yeasts, but also in somatic human cells. The function of the cdc2/cyclin B enzyme appears to be the same in human cells as in other cell types (Riabowol, K. et al., *Cell* 57:393–401 (1989)). A human A type cyclin has also been found in association with cdc2. No CLN type cyclin has yet been described in mammalian cells. A better understanding of the elements involved in cell cycle regulation and of their interactions would contribute to a better understanding of cell replication and perhaps even alter or control the process.

SUMMARY OF THE INVENTION

The present invention relates to a novel class of cyclins, referred to as D-type cyclins, which are of mammalian origin and are a new family of cyclins related to, but distinct from, previously described A, B or CLN type cyclins. In particular, it relates to human cyclins, encoded by genes shown to be able to replace a CLN-type gene essential for cell cycle start in yeast, which complement a deficiency of a protein essential for cell cycle start and which, on the basis of protein structure, are on a different branch of the evolutionary tree from A, B or CLN type cyclins. Three members of the new family of D-type cyclins, referred to as the human D-type cyclin gene family, are described herein. They encode small (33–34 KDa) proteins which share an average of 57% identity over the entire coding region and 78% in the cyclin box. One member of this new cyclin family, cyclin D1 or CCND1, is 295 amino acid residues and has an estimated molecular weight of 33,670 daltons (Da). A second member, cyclin D2 or CCND2, is 289 amino acid residues and has an estimated molecular weight of 33,045 daltons. It has been mapped to chromosome 12p band pl3. A third member, cyclin D3 or CCND3, is 292 amino acid residues and has an estimated molecular weight of approximately 32,482 daltons. It has been mapped to chromosome 6p band p21. The D-type cyclins described herein are the smallest cyclin proteins identified to date. All three cyclin genes described herein are interrupted by an intron at the same position. D-type cyclins of the present invention can be produced using recombinant techniques, can be synthesized chemically or can be isolated or purified from sources in which they occur naturally. Thus, the present invention includes recombinant D-type cyclins, isolated or purified D-type cyclins and synthetic D-type cyclins. Two of the three novel D-type cyclins (cyclin D1 and cyclin D3) have been shown to bind to a novel cyclin dependent kinase (CDK), designated CDK5, which is also the subject of the present invention. Using the methods described herein and an appropriate test system, such as a cell line which expresses cyclin D2, it is possible to determine whether cyclin D2 also binds CDK5. Unlike other cyclin dependent kinases, CDK5 has a PSSALRE motif (amino acid sequence 45–51), rather than the PSTAIRE motif which is conserved in other known members of the CDK family. CDK5 has been shown to be expressed in all cultured cells examined thus far and, therefore, it seems likely that it may perform important, yet unique, role(s) in the cell cycle.

The present invention also relates to DNA or RNA encoding a D-type cyclin of mammalian origin, particularly of human origin, as well as to antibodies, both polyclonal and monoclonal, specific for a D-type cyclin of mammalian, particularly human, origin. Antibodies specific for each of the D-type cyclins described specifically herein (cyclin D1, cyclin D2 and cyclin D3) are in particular the subject of the present invention.

The present invention further relates to a method of isolating genes encoding other cyclins, such as other D-type cyclins and related (but non-D type) cyclins. It also has diagnostic and therapeutic aspects. For example, it relates to a method in which the presence and/or quantity of a D-type cyclin (or cyclins) in tissues or biological samples, such as blood, urine, feces, mucous or saliva, is determined, using a nucleic acid probe based on a D-type cyclin gene or genes described herein or an antibody specific for a D-type cyclin. This embodiment can be used to predict whether cells are likely to undergo cell division at an abnormally high rate (i.e., if cells are likely to be cancerous), by determining whether their cyclin levels or activity are elevated (elevated level of activity being indicative of an increased probability that cells will undergo an abnormally high rate of division). The present method also relates to a diagnostic method in which the occurrence of cell division at an abnormally high rate is assessed based on abnormally high levels of a D-type cyclin(s), a gene(s) encoding a D-type cyclin(s) or a transcription product(s) (RNA).

In addition, the present invention relates to a method of modulating (decreasing or enhancing) cell division by altering the activity of at least one D-type cyclin, such as D1, D2 or D3, the activity of another molecule or molecules with which D-type cyclin associates or interacts, or the activity of both in cells. The present invention particularly relates to a method of inhibiting increased cell division by interfering with the activity or function of a D-type cyclin(s) or of a molecule(s) with which a D-type cyclin associates or interacts. D-type cyclins of the present invention have been shown to associate, in eukaryotic cells, particularly human cells, with multiple cyclin dependent kinases. They have also been shown to co-precipitate with three polypeptides: a cyclin-dependent kinase, a well characterized DNA replication and repair factor (i.e., proliferating cell nuclear antigen or PCNA) and a polypeptide of 21 kDa apparent molecular weight. Results suggest that D-type cyclin, CDK, PCNA and p21 exist in a quaternary complex, that many combinatorial variations of the components (e.g., cyclin D1 or D3 and CDK2, CDK4 and CDK5) assemble in vivo and that each of the quaternary complexes may have a subtly different role in the cell cycle or in different cell types. This knowledge serves as the basis for a variety of approaches to modulating cell division by altering the activity (directly or indirectly) of a D-type cyclin. In one embodiment, it offers specificity in modulating cell division (i.e., the ability to selectively alter cell division in particular cell types or at a particular point in the cycle) because of the specificity of expression of D-type cyclins in cells and the number of possible combinations of the components of the quaternary complex which appear to be formed by D-type cyclin, CDK, PCNA and p21. In a second embodiment, it offers a means by which cell division can be non-specifically altered by interfering with a common component of the quaternary complex of which D-type cyclin is a constituent, such as by interfering with PCNA.

For example, in one embodiment of a therapeutic method of the present invention, function of D-type cyclin(s) is blocked (totally or partially) by interfering with its ability to activate the protein kinase it would otherwise (normally) activate (e.g., p34 or a related protein kinase), by means of agents which interfere with D-type cyclin activity, either directly or indirectly. Such agents include anti-sense sequences or other transcription modulators which bind D cyclin-encoding DNA or RNA; antibodies which bind either the D-type cyclin or a molecule with which a D-type cyclin must interact or bind in order to carry out its role in cell cycle start; substances which bind the D-type cyclin(s); agents (e.g., proteases) which degrade or otherwise inactivate the D-type cyclin(s); or agents (e.g., low molecular weight inhibitors, small organic molecules) which interfere with association of the D-type cyclin with the catalytic subunit of the kinase or inactivate the catalytic subunit itself. In another embodiment, formation of the quaternary complex described above is prevented or enhanced or the activity of a complex member is altered as an approach to altering cell division. Here, too, agents which act indirectly or directly to prevent or enhance complex formation or to alter a constituent's activity can be used. For example, as described above, catalytic activity can be inhibited by preventing activation of the protein kinase. Alternatively, PCNA inhibitors can be introduced into cells in which cell cycle start is to be inhibited, resulting in inhibition of cell division. PCNA inhibitors can act indirectly (e.g., to reduce production of PCNA by interfering with transcription or translation) or directly (e.g., to bind PCNA and prevent it from joining with other complex members). Inhibitors of p21 can also be introduced into cells and interfere, indirectly or directly, with p21 function and/or binding to the complex members. Protein-protein interactions (between or among complex components) can also be altered (reduced or enhanced) to have the desired effect on the cell cycle (to reduce or increase cell division). Agents which block such protein—protein interactions can be used. These include low molecular weight inhibitors, agents which bind to complex components (e.g., antibodies) and agents which degrade or otherwise destroy a component's ability to form a complex with the other proteins. If enhanced quaternary complex formation is desired, agents which increase the ability of complex members to interact and bind (e.g., agents which change the configuration of a complex component so that it is more available for protein—protein interactions necessary for complex formation can be introduced into cells). Enhanced complex formation can also be brought about by increasing in cells the number, activity or availability of the limiting member(s) of the quaternary complex, thus enhancing the rate at which it is formed and its availability to act.

The subject invention also related to agents (e.g., oligonucleotides, antibodies, peptides) useful in the isolation, diagnostic or therapeutic methods described.

BRIEF DESCRIPTION OF THE DRAWINGS

FIG. 2 is the human cyclin D1 nucleic acid sequence (SEQ ID No. 1) and amino acid sequence (SEQ ID No. 2), in which nucleotide numbers and amino acid numbers are on the right, amino acid numbers are given with the initiation methionine as number one and the stop codon is indicated by an asterisk.

FIG. 3 is the human cyclin D2 nucleic acid sequence (SEQ ID No. 3) and amino acid sequence (SEQ ID No. 4) in which nucleotide numbers and amino acid numbers are on the right, amino acid numbers are given with the initiation methionine as number one and the stop codon is indicated by an asterisk.

FIG. 4 is the human cyclin D3 nucleic acid sequence (SEQ ID No. 5) and amino acid sequence (SEQ ID No. 6), in which nucleotide numbers and amino acid numbers are on the right, amino acid numbers are given with the initiation methionine as number one and the stop codon is indicated by an asterisk.

FIGS. 5A and 5B show the cyclin gene family.

FIG. 5A shows the amino acid sequence alignment of seven cyclin genes (CYCD1-Hs, SEQ ID No. 7; CYCA-Hs, SEQ ID No. 8; CYCA-Dm, SEQ ID No. 9; CYCB1-Hs, SEQ ID No. 10; CDC13-Sp, SEQ ID No. 11; CLN1-Sc, SEQ ID No. 12; CLN3-Sc, SEQ ID No. 13), in which numbers within certain sequences indicate the number of amino acid residues omitted from the sequence as the result of insertion.

FIG. 5B is a schematic representation of the evolutionary tree of the cyclin family, constructed using the Neighbor-Joining method; the length of horizontal line reflects the divergence.

FIG. 6 shows alternative polyadenylation of the cyclin D1 gene transcript.

FIG. 6, panel A is a comparison of several cDNA clones isolated from different cell lines. Open boxes represent the 1.7 kb small transcript containing the coding region of cyclin D1 gene. Shadowed boxes represent the 3' fragment present in the 4.8 kb long transcript. Restriction sites are given above each cDNA clone to indicate the alignment of these clones.

FIG. 6, panel B shows the nucleotide sequence surrounding the first polyadenylation site for several cDNA clones (CYCD1-21, SEQ ID No. 14; CYCD1-H12, SEQ ID No. 15; CYCD1-HO34, SEQ ID No. 16; CYCD1-TO78, SEQ ID No. 17 and a genomic clone; CYCD1-GO68, SEQ ID No. 18).

FIG. 6, panel C is a summary of the structure and alternative polyadenylation of the cyclin D1 gene. Open boxes represent the small transcript, the shadowed box represents the 3' sequence in the large transcript and the filled boxes indicate the coding regions.

FIG. 8 is a schematic representation of the genomic structure of human cyclin D genes, in which each diagram represents one restriction fragment from each cyclin D gene that has been completely sequenced. Solid boxes indicate exon sequences, open boxes indicate intron or 5' and 3' untranslated sequences and hatched boxes represent pseudogenes. The positions of certain restriction sites, ATG and stop codons are indicated at the top of each clone.

FIG. 9 is the nucleic acid sequence (SEQ ID No. 30) and amino acid sequence (SEQ ID No. 31) of a cyclin D2 pseudogene.

FIG. 10 is the nucleic acid sequence (SEQ ID No. 32) and the amino acid sequence (SEQ ID No. 33) of a cyclin D3 pseudogene.

FIG. 11 is the nucleic acid sequence (SEQ ID No. 34) of 1.3 kb of human cyclin D1 promoter; the sequence ends at initiation ATG codon and transcription starts at approximately nucleotide −160.

FIG. 12 is the nucleotide sequence (SEQ ID No. 35) of 1.6 kb of human cyclin D2 promoter; the sequence ends at initiation ATG codon and transcription starts at approximately nucleotide −170.

FIG. 13 is the nucleotide sequence (SEQ ID No. 36) of 3.2 kb of human cyclin D3 promoter; the sequence ends at initiation ATG codon and transcription starts at approximately nucleotide −160.

FIG. 14 is the nucleotide sequence (SEQ ID No. 37) of human CDK4 cDNA, which encodes an open reading frame of 292 amino acid residues which are shown in single-letter code (SEQ ID No. 37). The underlined peptide (right amino acid residues) at the carboxy-terminus of CDK4 was synthesized to generate peptide antibody.

FIG. 15A: $^{35}$S-methionine-labelled 293 (lanes 1, 2 and 3) or WI38 (lanes 4, 5 and 6) cell lysates were immunoprecipitated with pre-immune serum (lanes 1 and 4), anti-cyclin D1 antiserum (lanes 2 and 5) and anti-CDK2 antiserum (lanes 3 and 6).

FIG. 15B: $^{35}$S-methionine-labelled WI38 cell lysate was precipitated with pre-immune (lane 1), anti-cyclin D1 (lane 2), and anti-CDK4 antiserum.

FIG. 15C: $^{35}$S-methionine-labelled WI38 cell lysates were immunoprecipitated with pre-immune serum (lane 1), anti-CDK5 peptide antibody in the absence (lane 2) or in the presence of competing CDK5 peptide (lane 3), anti-cyclin D1 (lane 4), or anti-PCNA (lane 5) antisera. The immunoprecipitated polypeptides were analyzed in each case by SDS-polyacrylamide gel electrophoresis as described in Experimental Procedures. The mobility of protein molecular weight standards (BRL) and relevant proteins are indicated.

FIG. 16A is a summary of established pair-wise protein—protein interactions, in which each arrow indicates a demonstrated co-precipitation between two proteins.

FIG. 16B is a schematic representation of the proposed quaternary complex between D-type cyclins, CDKs, p21 and PCNA.

DETAILED DESCRIPTION OF THE INVENTION

Figure 1:
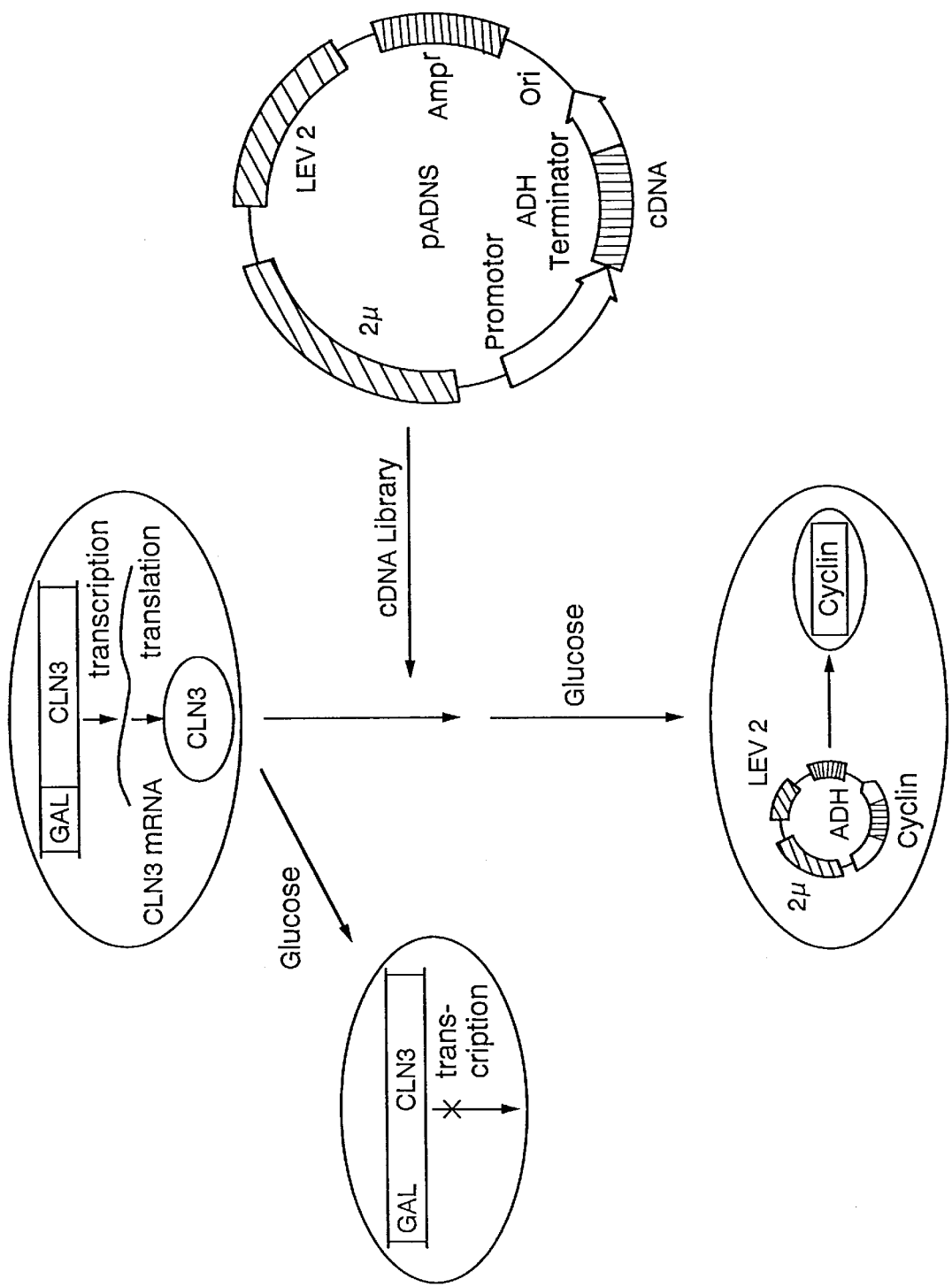
FIG. 1 is a schematic representation of a genetic screen for human cyclin genes.

As described herein, a new class of mammalian cyclin proteins, designated D-type cyclins, has been identified, isolated and shown to serve as a control element for the cell cycle start, in that they fill the role of a known cyclin protein by activating a protein kinase whose activation is essential for cell cycle start, an event in the G1 phase at which a cell becomes committed to cell division. Specifically, human D-type cyclin proteins, as well as the genes which encode them, have been identified, isolated and shown to be able to replace CLN type cyclin known to be essential for cell cycle start in yeast. The chromosomal locations of CCND2 and CCND3 have also been mapped.

As a result, a new class of cyclins (D type) is available, as are DNA and RNA encoding the novel D-type cyclins, antibodies specific for (which bind to) D-type cyclins and methods of their use in the identification of additional cyclins, the detection of such proteins and oligonucleotides in biological samples, the inhibition of abnormally increased rates of cell division and the identification of inhibitors of cyclins. In addition, two novel D-type cyclins have been shown to bind to a novel cyclin dependent kinase, designated CDK5 and described herein. CDK5 has been shown to differ from all known members of the CDK kinase family in that it has a PSSALRE motif (amino acid residues 45–51) and not the PSTAIRE motif which is conserved among all other known CDKs.

Further, as described herein, Applicant has determined that in eukaryotic cells, specifically human cells, D-type cyclin associates with multiple catalytic subunits (cyclin dependent kinases or CDK). Applicant has also shown that D-type cyclin and CDK co-precipitate with two additional polypeptides: a well characterized DNA replication and repair factor (i.e., proliferating cell nuclear antigen or PCNA) and a polypeptide of 21 kDa apparent molecular weight. Results described herein suggest that D cyclin, CDK, PCNA and p21 exist in a quaternary complex, that many combinatorial variations of the components (e.g., cyclin D1 or D3 and CDK2, CDK4 and CDK5) assemble in vivo and that each of the resulting quaternary complexes may have a subtly different role in the cell cycle or in different cell types.

Applicant's work, thus, links a human D cyclin whose biochemical function is unknown and which appears to be a G1 cyclin which is identical to a putative oncogene (PRAD1) with a DNA replication and repair factor. Thus, Applicant's work also provides the first biochemical indication of a possible function of D-type cyclins (i.e., as modulators of PCNA function) and, for the first time, provides evidence of a role for D-type cyclins in G1 or S phase of the cell cycle. In addition, Applicant has shown that D-type cyclins are differentially expressed among various cell types and are also differentially expressed or regulated within the same type of cells, depending on the differentiation state of the cells. Therefore, methods of the present invention offer the particular advantage of flexibility and specificity, in that D-type cyclin activity can be altered on the basis of type of D-type cyclin (e.g., D1, D2, D3), across cell types, in a cell-type specific manner or on the basis of cell cycle phase or stage. Further, because of the key roles cyclins have been shown to have in cell cycle control and the evidence, provided herein, of a role for D-type cyclins in the G1 to S transition, the present work provides the basis for a method of regulating the cell cycle which extends to a wide variety of proliferative disorders (any such disorders in which a D-type cyclin plays a determinative role in regulating cell cycle start). Disorders in which the method of the present invention can be used to inhibit cell proliferation include leukemia and tumorigenesis.

Each of the components of the D-type cyclin-containing complex represented in FIG. 16 is a potential target for the present method of altering, particularly inhibiting, cell cycle start and, thus, altering cell division. Selection of the proper "target" constituent of the complex makes the present method highly specific, if desired.

Applicant's work, thus, provides the basis for a better understanding of D-type cyclins, their roles and interactions with other molecules in cell cycle start and approaches to altering or modulating (decreasing or enhancing) eukaryotic cell division, particularly human cell division.

The following is a description of the identification and characterization of human D-type cyclins and of the uses of these novel cyclins and related products, the identification and characterization of a novel cyclin dependent kinase (CDK5); evidence of a role for D-type cyclins in G1 or S phase of the cell cycle; and the discovery that D-type cyclin is associated with three additional polypeptides (CDK, PCNA and p21) in what appears to be a quaternary complex in which many combinatorial variations are possible, resulting in a variety of resulting complexes which may play different roles in the cell cycle or in different cell types.

Isolation and Characterization of Human Cyclin D1, D2 and D3

As represented schematically in FIG. 1 and described in detail in Example 1, a mutant yeast strain in which two of the three CLN genes (CLN1 and CLN2) were inactive and expression of the third was conditional, was used to identify human cDNA clones which rescue yeast from CLN deficiency. A human glioblastoma cDNA library carried in a yeast expression vector (pADNS) was introduced into the mutant yeast strain. Two yeast transformants (pCYCD1-21 and pCYCD1-19) which grew despite the lack of function of all three CLN genes and were not revertants, were identified and recovered in E. coli. Both rescued the mutant (CLN deficient) strain when reintroduced into yeast, although rescue was inefficient and the rescued strain grew relatively poorly. pCYCD1-19 and pCYCD1-21 were shown, by restriction mapping and partial DNA sequence analysis, to be independent clones representing the same gene. A HeLa cDNA library was screened for a full length cDNA clone, using the 1.2 kb insert of pCYCD1-21 as probe. Complete sequencing was done of the longest of nine positive clones identified in this manner (pCYCD1-H12; 1325 bp). The sequence of the 1.2 kb insert is presented in FIG. 2; the predicted protein product of the gene is of approximate molecular weight 34,000 daltons.

Cyclin D2 and cyclin D3 cDNAs were isolated using the polymerase chain reaction and three oligonucleotide probes derived from three highly conserved regions of D-type cyclins, as described in Example 4. As described, two 5' oligonucleotides and one 3' degenerate oligonucleotide were used for this purpose. The nucleotide and amino acid sequences of the CCND2 gene and encoded D2 cyclin protein are represented in FIG. 3 and of the CCND3 and encoded D3 cyclin protein are represented in FIG. 4. A deposit of plasmid pCYC-D3 was made with the American Type Culture Collection (Rockville, Md.) on May 14, 1991, under the terms of the Budapest Treaty. Accession number 68620 has been assigned to the deposit.

Comparison of the CYCD1-H12-encoded protein sequence with that of known cyclins (see FIG. 5A) showed that there was homology between the new cyclin and A, B and CLN type cyclins, but also made it clear that CYCD1 differs from these existing classes.

Figure 5B:
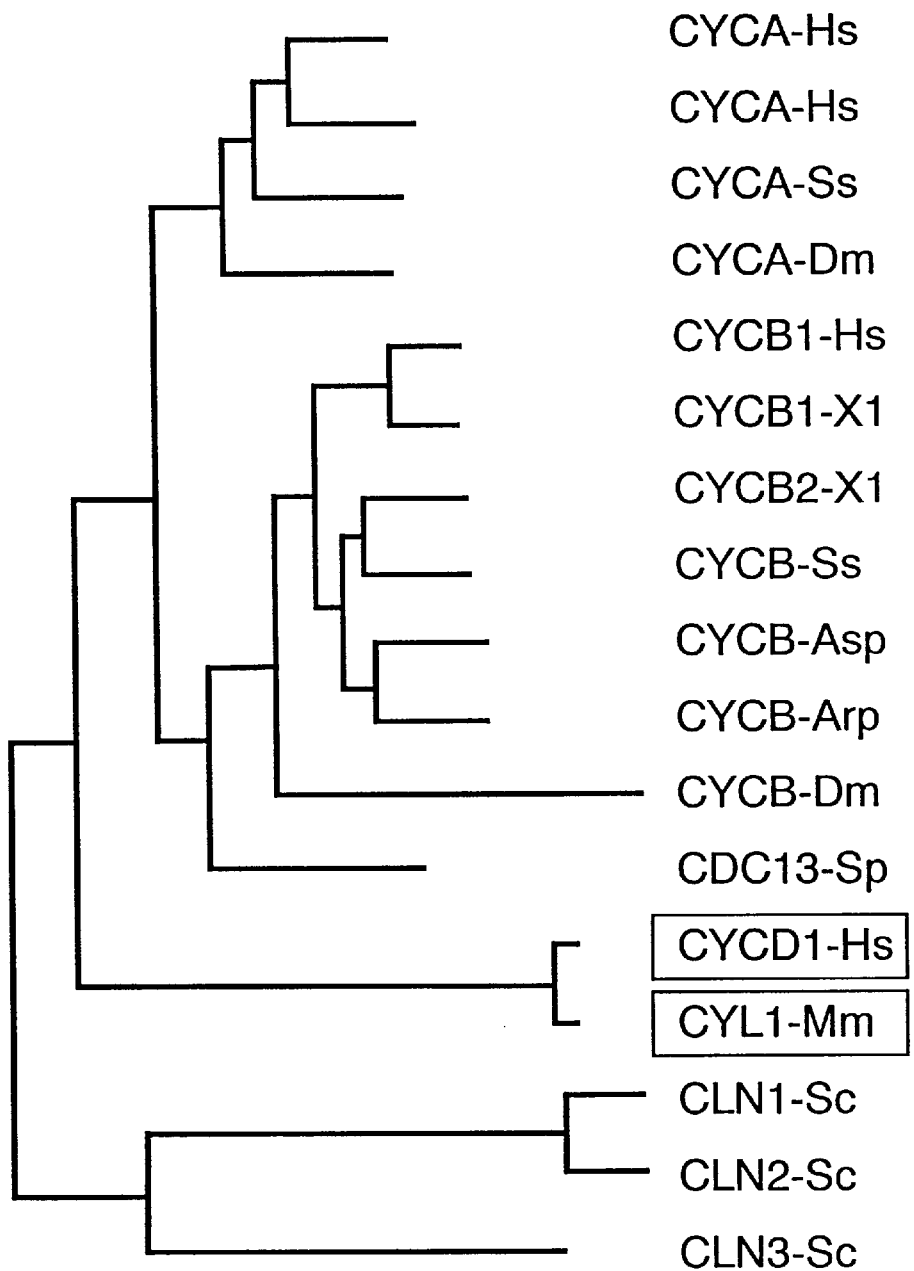

An assessment of how this new cyclin gene and its product might be related in an evolutionary sense to other cyclin genes was carried out by a comprehensive comparison of the amino acid sequences of all known cyclins (FIG. 5B and Example 1). Results of this comparison showed that CYCD1 represents a new class of cyclin, designated herein cyclin D.

Expression of cyclin D1 gene in human cells was studied using Northern analysis, as described in Example 2. Results showed that levels of cyclin D1 expression were very low in several cell lines. The entire coding region of the CYCD1 gene was used to probe poly(A)+RNA from HeLa cells and demonstrated the presence of two major transcripts, one approximately 4.8 kb and the other approximately 1.7 kb, with the higher molecular weight form being the more abundant. Most of the cDNA clones isolated from various cDNA libraries proved to be very similar to clone ACYCD1-H12 and, thus, it appears that the 1.7 kb transcript detected in Northern blots corresponds to the nucleotide sequence of FIG. 2. The origin of the larger (4.8 kb) transcript was unclear. As described in Example 2, it appears that the two mRNAs detected (4.8 kb and 1.7 kb) arose by differential polyadenylation of CYCD1 (FIG. 6).

Differential expression of cyclin D1 in different tissues and cell lines was also assessed, as described in Example 3. Screening of cDNA libraries to obtain full length CYCD1 clones had demonstrated that the cDNA library from the human glioblastoma cell line (U118 MG) used to produce yeast transformants produced many more positives than the other three cDNA libraries (human HeLa cell cDNA, human T cell cDNA, human teratocarcinoma cell cDNA). Northern and Western blotting were carried out to determine whether cyclin D1 is differentially expressed. Results showed (Example 3) that the level of transcript is 7 to 10 fold higher in the glioblastoma (U118 MG) cells than in HeLa cells, and that in both HeLa and U118 MG cells, the high and low molecular weight transcripts occurred. Western blotting using anti-CYL1 antibody readily detected the presence of a 34 kd polypeptide in the glioblastoma cells and demonstrated that the protein is far less abundant in HeLa cells and not detectable in the 293 cells. The molecular weight of the anti-CYCL1 cross-reactive material identified in U118 MG and HeLa cells is exactly that of the human CYCD1 protein expressed in $E.\ coli$. Thus, results demonstrated differential occurrence of the cyclin D1 in the cell types analyzed, with the highest levels being in cells of neural origin.

As also described herein (Example 6), human genomic libraries were screened using cDNA probes and genomic clones of human D-type cyclins, specifically D1, D2 and D3, have been isolated and characterized. Nucleic acid sequences of cyclin D1, D2 and D3 promoters are represented in FIGS. 11–13. Specifically, the entire 1.3 kb cyclin D1 cDNA clone was used as a probe to screen a normal human liver genomic library, resulting in identification of three positive clones. One of these clones (G6) contained a DNA insert shown to contain 1150 bp of upstream promoter sequence and a 198 bp exon, followed by an intron. Lambda genomic clones corresponding to the human cyclin D2 and lambda genomic clones corresponding to the human cyclin D3 were also isolated and characterized, using a similar approach. One clone ($\lambda$D2-G4) was shown to contain (FIG. 8B) a 2.7 kb SacI SmaI fragment which includes 1620 bp of sequence 5' to the presumptive initiating methionine codon identified in D2 cDNA (FIG. 3) and a 195 bp exon followed by a 907 bp intervening sequence. One clone (G9) was shown to contain (FIG. 8C) 1.8 kb of sequence 5' to the presumptive initiating methionine codon identified in D3 cDNA (FIG. 4), a 198 bp exon 1, a 684 bp exon 2 and a 870 bp intron.

Thus, as a result of the work described herein, a novel class of mammalian cyclins, designated cyclin D or D-type cyclin, has been identified and shown to be distinct, on the basis of structure of the gene (protein) product, from previously-identified cyclins. Three members of this new class, designated cyclin D1 or CCND1, cyclin D2 or CCND2 and cyclin D3 or CCND3, have been isolated and sequenced. They have been shown to fulfill the role of another cyclin (CLN type) in activation of the protein kinase (CDC28) which is essential for cell cycle start in yeast. It has also been shown that the cyclin D1 gene is expressed differentially in different cell types, with expression being highest in cells of neural origin.

Identification of a Novel Kinase Associated with D-Type Cyclins and Demonstration that D-type DNA Replication and Repair Factor PCNA As described in Example 8, a novel cyclin-dependent kinase, designated CDK5, has been identified, characterized and sequenced. As described briefly below and in detail in Example 8, a human cDNA clone coding for a polypeptide which cross-reacts with antiserum raised against $S.\ pombe$ $p34^{cdc}$ was isolated. The cDNA encodes a 33 Kd polypeptide which shares 56.8% and 60.3% homology with human CDC2 and CDK2, respectively. The protein was shown, as also described in Example 8, to complex with human cyclin D1 and D3. Based on these findings, the gene product of this clone is designated CDK5. The nucleotide sequence of the human CDK5 cDNA and the amino acid sequence of the encoded protein are shown in FIG. 14.

As also described below and in Example 8, immunological procedures have been used to establish that D-type cyclins associate, in eukaryotic cells, with a variety of potential catalytic subunits (e.g., CDKs, such as CDK2, CDK4 and CDK5). In addition, these procedures have shown that the D-type cyclin and CDK associate with the replication factor PCNA and a polypeptide of 21 kDa apparent molecular weight. The various pair-wise interactions possible are summarized in FIG. 16A.

Human cyclin D1 has been associated with a wide variety of proliferative diseases, but its biochemical role is unknown. As described herein, in human diploid cells, specifically human diploid fibroblasts, cyclin D1 is complexed with many other cellular proteins. Among them are protein kinase catalytic subunits CDK2, CDK4 (previously called PSK-J3), and CDK5 (also called PSSALRE). In addition, polypeptides of 21 kDa and 36 kDa are identified in association with cyclin D1. As described in Example 8, it has been shown that the 36 kDa protein is the proliferating cell nuclear antigen, PCNA. PCNA has been described as an essential accessory factor to the delta polymerase, which is required for leading-strand DNA replication and DNA repair. Cyclin D3 also associates with multiple protein kinases, p21 and PCNA, as shown herein. It is proposed that there exists a quaternary complex of D cyclin CDK, PCNA and p21 and that many combinatorial variations (cyclin D1, D3, CDK2, 4 and 5) may assemble in vivo. These findings link a human putative G1 cyclin that is associated with oncogenesis with a well characterized DNA replication and repair factor.

Investigation of Proteins that Associate with Cyclin D

It is well established that the cdc2-cyclin B protein kinase plays a critical role in controlling the G2/M transition in both mammalian and yeast cells (Draetta, G., *Trends. Biol. Sci.* 15:378–383 (1990)).

Considerable effort has also been directed toward the isolation of mammalian cyclins that might function at the G1 and S phases of the cell cycle. In a search for a putative oncogene located on band q13 of human chromosome 11, the site of the BCL1 rearrangement in certain lymphomas and leukemias, and also of gene amplification in 15–20% human breast cancers, a cyclin (PRADL) was identified as the putative oncogene (Motokura et al.,*Nature* 350:512–515 (1991); Withers et al., *Mol. Cell. Biol.* 11:4846–4853 (1991)). The identical gene, called cyclin D1, in addition to two further human cyclin genes, cyclin C and cyclin E, were isolated by virtue of their ability to rescue a budding yeast strain that lacks G1 cyclin (Cln) function (Xiong et al., *Current Biology* 1:362–364 (1991); Koff et al., *Cell* 66:1217–1228 (1991); Lew et al., *Cell* 66:1197–1206 (1991)), reviewed in Xiong and Beach, *Current Biology* 1:362–364 (1991)). In yet another approach, three mouse homologs of human cyclin D1, named CYL1, 2 and 3 were identified as cellular genes whose expression is stimulated by CSF-1 (colony-stimulating factor 1) in macrophage cell lines (Matsushime et al., *Cell* 65:701–713 (1991)). Two additional human D-type cyclins, cyclin D2 and D3, were isolated as human homologs of murine cyl2 and cyl3 using PCR and low stringency hybridization techniques (Inaba et al., *Genomics* 13:565–574 (1992); Xiong et al., *Genomics* 13:575–584 (1992)).

Several lines of very indirect evidence suggest a G1 or S phase role for D-type cyclins. Following stimulation of murine macrophages CSF-1, the levels of both cyclin D1/cyl1 and cyclin D2/cyl2 mRNA increased in the early or middle G1 phase and reached a maximum of the G1/S border. The level of cyclin D/cyl1 protein also increases throughout G1, declines during S and G2 and reaches a nadir after mitosis (Matsushime et al., *Cell* 65:701–713 (1991); Kiyokawa et al., *Proc. Natl. Acad. Sci. USA* 89:2444–2447 (1992)). In similar experiments carried out with human diploid fibroblasts, the level of both cyclin D1 and D3 mRNA increases gradually throughout G1 and peaks prior to the onset of S phase. Despite these observations, however, there has been no direct evidence for a G1/S function of any of the D-type cyclins. Applicant has investigated proteins that associate with cyclin D and found a substantial physical association between D cyclins and a DNA replication factor (i.e., PCNA).

Multiple Cyclin D1-Associated Proteins

To identify proteins that specifically associate with cyclin D, anti-cyclin D1 immunoprecipitates of [$^{35}$S ] methionine-labelled WI38 human diploid fibroblasts lysates were examined (see Example 8, Experimental Procedures). WI38 cells were initially chosen for this study because they are a relatively normal cell line that expresses reasonably high levels of cyclin D1 and a low level of cyclin D3 mRNA (Won et al., *Proc. Natl. Acad. Sci.* (1992). Human 293 transformed primary embryonal kidney cells were used as controls because they express all three D cyclin mRNAs and proteins at extremely low levels (Xiong, et al., *Cell* 65:691–699 (1991); FIG. 1A, lane 5). W138 cells express a readily detectable 35 kDa polypeptide that can be immunoprecipitated by the anti-cyclin D1 antiserum. The identity of the 35 kDa protein as cyclin D1 was confirmed by comparison of an immunoprecipitate of the same W138 cell lysate with pre-immune serum (FIG. 1A, lane 4), and with a similar precipitation of 293 cell lysate with the same anti-cyclin D1 antiserum (FIG. 1A, lane 2). Because of the existence of three closely related cyclin D genes in human cells, and weak cross-reactivity of the anti-cyclin D1 antibody to other cyclin D proteins, the identity of the 35 kDa band was further investigated by partial proteolytic mapping. *S. aureus* V8 partial proteolysis of the 35 kDa band revealed the same pattern as that of similar cleaved cyclin D1 synthesized in vitro, but not as that of cyclin D2 or D3.

In addition to the intense 35 kDa band corresponding to cyclin D1, three other major bands, p33 and p21 and one minor band, p31, appeared specifically in the anti-cyclin D1 precipitates (FIG. 1A, lane 5; FIG. 1C, lane 4). These polypeptides are absent from precipitates of W138 cell lysate using pre-immune serum (FIG. 1A, lane 4) or precipitates of 293 cell lysates with the same anti-cyclin D1 antibody (FIG. 1A, lane 2). The possibility that any of these four bands, in particular p31 and p33, might be cyclin D2 or D3 was ruled out by comparing their partial V8 proteolysis patterns with those of in vitro translated D2 and D3. Precipitation of these polypeptides with anti-cyclin D1 serum is also not likely due to the presence of cross-reactive epitopes in any of these proteins, since they were not detected following immunoprecipitation coupled with Western blotting using the same antibody. Experiments to identify the cyclin D1-associated proteins are described below.

CKD5 Associates with D-Type Cyclins

It has been previously reported that murine macro-phages cyclin D1/cyl1 associates with a polypeptide that cross-reacts with an antibody to full-length p34cdc2 of *Schizosaccharomyces pombe* (G8), but not with an antibody prepared against the C-terminus of human p34cdc2 (Draetta et al., *Cell* 50, 319–325 (1987); Draetta and Beach, *Cell* 54,17–26. (1988); Matsushime et al., *Cell* 65,701–713 (1991). Essentially identical results were obtained in human W138 cells, suggesting that cyclin D1 associates with a relative of human CDC2.

The G8 antibody was used to screen human cDNA expression libraries (see Experimental Procedures), in order to isolate putative D-type cyclin-associated kinases. Thirty four G8-positive cDNA clones were identified from a HeLa cell cDNA library. Among these, 17 clones encoded CDC2 and another 14 encoded for CDK2. One of the remaining clones encodes an ORF of 292 amino acid residues with a predicted molecular weight of 33,283 daltons. This clone is designated CDK5, since it shares extensive amino acid identity to the known cyclin-dependent kinases (CDKs), including *S. pombe* CDC2 (53.4%), *S. cerevisiae* CDC28 (55.9%), human CDC2 (56.8%), and human CDK2 (60.3%), and associates with human D-type cyclins (see below). CDK5 has an inferred amino-acid sequence that is almost identical to a putative protein kinase which was recently identified using polymerase chain reaction (PCR) with primers that are conserved among cdc2 genes (Meyerson et al., *EMBO J.* 11, 2909–2917 (1992)). CDK5 encodes a sequence of DLKKYFD at amino acid sequence 86 to 92 and the protein referred to as PSSALRE (Meyerson et al., *EMBO J.* 11:2090–2917 (1992)) contains DLK-NFD at the corresponding region. It is not known whether these two polypeptides are derived from two genes, spliced differently, or whether the discrepancy might have arisen from a cloning or sequencing artifact. In the corresponding region, human CDC2 has the sequence of DLKKYLD and CDK2 has DLK KFMD.

To determine whether CDK5 associates with D cyclins, an antiserum was raised against a peptide corresponding to the unique carboxy-terminal region of CDK5 (see Example 8, Experimental Procedures). This serum does not cross react with human CDC2, CDK2, or CDK4. Immunoprecipitation (FIG. 1C, lane 2) or Western-blotting following immunoprecipitation showed that this antiserum detected a polypeptide with a $M_r$ 31 kDa (p31) from cell lysate, which comigrated with CDK5 polypeptide synthesized in vitro and was effectively competed away by the CDK5 antigenic peptide (FIG. 1C, lane 3). The identity of the 31 kDa protein precipitated by the anti-CDK5 antibody was further confirmed to be CDK5 by comparing the partial V8 proteolytic mapping of p31 with in vitro translated CDK5.

Immunoprecipitation of cell lysates of $^{35}$S-methionine labeled W138 cells using the anti-CDK5 antiserum revealed several polypeptides, in addition to $p31^{CDK5}$. Among these, polypeptides of 36 kDa (p36), p35 kDa (p35), 33 kDa (p33) and 21 kDa (p21, FIG. 1C, lane 2) were most prominent and specifically coprecipitated by the anti-CDK5 antiserum. All four polypeptides were absent from precipitates with the pre-immune serum or in the presence of excess amount of the CDK5 carboxy-terminal peptide (FIG. 1C, lanes 1 and 3).

The electrophoretic mobilities of p35 and p33 were found to be the same as that of in vitro translated human cyclin D1 and D3, respectively. To directly test the possibility that the CDK5-associated p35 might correspond to cyclin D1, CDK5 immunoprecipitates were blotted with anti-cyclin D1 antisera. A 35 kDa polypeptide, which comigrated with $p35^{cyclin\ D1}$, was detected by the anti-cyclin D1 antiserum. Reciprocal blotting of anti-cyclin D1 immunocomplexes by the CDK5 antiserum also revealed the presence of a 31 kDa polypeptide which had the same mobility as $p31^{CDK5}$. Similarly, CDK5 has also been detected in anti-cyclin D3 immunoprecipitates. These data suggest that the CDK5-associated p35 is cyclin D1 and CDK5-associated p33 is cyclin D3.

To seek conclusive evidence of the identity of the CDK5-associated p35 and p33 proteins, partial proteolytic mapping was employed (Cleveland et al., *J. Biol. Chem.* 252:1102–1106 (1977)). $^{35}$S-labelled p35 purified from anti-CDK5 immunoprecipitates was subjected to partial *S. aureus* V8 protease digestion and compared with similarly treated human $p35^{cyclinD1}$ obtained either from in vitro translation or from an anti-cyclin D1 immunoprecipitation. The V8 proteolytic pattern of p35 from anti-CDK5 immunoprecipitates was identical to that of cyclin D1, but distinct from that of cyclin D3. Similar experiments were also performed to confirm the identity of p33. The partial proteolytic pattern of the CDK5-associated p33 is identical to that of an vitro translated human cyclin D3, but not D1. Conversely, it has also been determined that the partial V8 digestion pattern of the cyclin D1-associated p31 (FIG. 1A, lane 5 and FIG. 1C, lane 4) is identical to CDK5 obtained either from in vitro translation or anti-CDK5 immunoprecipitation.

CDK2 Associates with Cyclin D

The apparent molecular weight of the cyclin D1-associated p33 (FIG. 1A, lanes 4 and 5) and also the cross reactivity of $p33^{CDK2}$ with the G8 antibody suggests the possibility that p33 might be CDK2. To test this, anti-CDK2 precipitate of a [$^{35}$S] methionine-labelled WI38 cell lysate was compared with an anti-cyclin D1 precipitate (FIG. 1A, lanes 5 and 6). As expected, the anti-C terminal CDK2 serum precipitated a 33 kDA protein which was confirmed to be $p33^{CDK2}$ by comparing the partial *S. aureus* V8 proteolysis pattern of the 33 kDa band with that of in vitro translated CDK2. $p33^{CDK2}$ comigrated with the p33 present in the anti-cyclin D1 precipitate. Reciprocally, anti-CDK2 antiserum also precipitated a 35 kDa protein which comigrated with cyclin D1 (FIG. 1A, lanes 5 and 5).

To seek further evidence for the existence of a possible association between CDK2 and cyclin D1, a WI38 cell lysate was immunoprecipitated with anti-cyclin D1, separated on SDS-PAGE and immunoblotted with anti-CDK2 antiserum. The anti-CDK2 antibody was raised against a carboxy-terminal peptide (Pagano et al., *EMBO J.* 11:961–971 (1992b)) and its specificity was checked by immunoblotting bacterially expressed human CDC2, CDK2, CDK3, CDK4 and CDK5. Only CDK2, and not the other four CDK proteins, was recognized by this antibody. CDK2 protein was detected in the precipitate with anti-CDK2 and anti-cyclin D1, but not in that with pre-immune serum nor with anti-CDK2 pre-incubated with competing antigenic peptides. In a reciprocal Western blot experiment, cell lysate was immunoprecipitated with anti-CDK2 and blotted with anti-cyclin D1. Cyclin D1 was detected in the anti-cyclin D1 aod anti-CDK2 immunoprecipitates, but not in precipitates with either preimmune serum or anti-CDK2 antiserum pre-incubated with a competing CDK2 peptide.

To test whether CDK2 also associates with cyclin D3, immunoprecipitates using antiserum to the C-terminal peptide of human cyclin D3 (see Example 8, Experimental Procedures) were blotted with anti-CDK2 antiserum. CDK2 was weakly detected in the anti-cyclin D3 precipitate, but not in the control precipitate with anti-cyclin D3 antiserum pre-incubated with a competing antigen peptide.

Finally, to further confirm the association between CDK2 and cyclin D, partial proteolytic mapping experiments were conducted. Initially, attempts were made to proteolytically map the cyclin D1-associated p33 to compare it with CDK2. However, because of the comigration of CDK2 with yet another predominant protein kinase in the anti-cyclin D1 precipitates, a different proteolytic pattern was obtained. Therefore, the converse experiment was performed. The 35 kDa band in anti-CDK2 immunoprecipitates was excised from SDS-polyacrylamide gel, partially digested with V8 protease and electrophoretically separated and compared with V8 digested $p35^{cyclin\ D1}$ derived either from in vitro translation or from an anti-cyclin D1 immunoprecipitation. The pattern of proteolytic cleavage was the same in each case.

pSK-J3/CDK4 is the Predominant p33 Protein Associated with Cyclin D1

The difference in the proteolytic pattern of cyclin D1-associated p33 from that of CDK2 suggested that the majority of D1-associated p33 corresponds to a protein other than CDK2. During attempts to identify this protein, it was suggested to us by Dr. Charles Sherr (St. Jude Children's Research Hospital, Tennessee) that a protein kinase called PSK-J3, originally identified in a screen with mixed oligonucleotide probes derived from conserved regions of serine/threonine kinases (Hanks, S. K., *Proc. Natl. Acad. Sci. USA* 84:388–392 (1987)), may have cyclin D binding properties. The predicted molecular mass of PSK-J3 is 34 kDa, close to that of p33. Because of its association with D cyclins, as demonstrated below, PSK-J3 is referred to hereinafter as CDK4. In vitro translated CDK4, and that precipitated from a cell lysate with anti-CDK4 serum, showed the same electrophoretic mobility as CDK2 and the D1-associated p33 (FIG. 1B, lanes 2 and 3). The identify of CDK4 precipitated by the anti-CDK4 antiserum was confirmed by comparing its partial V8 mapping pattern to that of in vitro translated CDK4.

Immunoprecipitation-Western blotting experiments were carried out to directly test whether the cyclin D1-associated p33 is CDK4. An anti-CDK4 serum reacted with a 33 kDa protein present in anti-cyclin D1 immunoprecipitates that has the same mobility as the CDK4 precipitated by anti-CDK4, but did not react with precipitates of either CDK2 or CDK5. Reciprocally, the anti-CDK4 antiserum also precipitated a 35 kDa protein detected by anti-cyclin D1 antibody. To further confirm the identity of the cyclin D1-associated p33, the partial V8 digestion pattern of p33 was compared to that of immunoprecipitated CDK4 and CDK2. The cyclin D1-associated p33 displayed a very similar pattern to that of CDK4, but was quite dissimilar to that of CDK2. This result indicates that CDK4 is considerably more abundant (at least as crudely assayed by methionine labelling) than CDK2 in anti-cyclin D1 precipitates of WI38 cells. Similarly, a 33 kDa polypeptide (p33) seen in anti-CDK4 immunoprecipitate has been identified to be cyclin D3 by partial V8 peptide mapping.

Association of p21 with Cyclin D1 and CDK2

In [$^{35}$S] methionine-labelled WI38 lysate precipitated with anti-cyclin D1 serum, a 21 kDa protein (p21) appeared to associate specifically with cyclin D1 (FIG. 1). p21 was not present in the precipitates with pre-immune serum (FIG. 1A, lane 4; FIG. 1B, lane 1), nor in the anti-cyclin D1 precipitate derived from 293 cells which contains undetectable levels of cyclin D1 (FIG. 1A, lane 2). Specific association of p21 with cyclin D1 was further supported by the presence of a comigrating 21 kDA protein in immunoprecipitates with sera against CDK2 (FIG. 1A, lane 6), CDK4 (FIG. 1B, lane 3) and CDK5 (FIG. 1C, lane 2). If anti-CDK2 antiserum was preblocked with a competing CDK2 peptide, the p21 band, and also p33$^{CDK2}$ and p35$^{cyclin\ D1}$ were not seen. Similarly, p21 was also absent from anti-CDK5 immunoprecipitates if the antiserum was pre-incubated with the CDK5 carboxyterminal antigen peptide (FIG. 1C, lane 3). p21 was not recognized in Western blots by any of the anti-CDK or anti-cyclin D antibodies used in this study. Furthermore, although the total immunoprecipitable CDK2 in 293 cells is similar to that in WI38 cells (FIG. 1A, lanes 3 and 6), the p21 band was not present in the CDK2 immunoprecipitates from 293 cell lysates. This finding suggests that the association of CDK2 and p21 is dependent on cyclin D.

To determine whether the p21 from cyclin D1 immunoprecipitates and CDK2 immunoprecipitates correspond to the same polypeptide, the partial V8 proteolytic pattern of the p21 purified from each source were compared. They are indeed the same. The p21 precipitated by anti-CDK5 antiserum was also found to be the same as cyclin D1-associated p21. The p21 in the anti-CDK4 immunoprecipitation was also proteolytically mapped (FIG. 1B, lane 3). It gave an identical pattern to the cyclin D1-associated p21. p21 does not correspond to the human max protein or p21$^{ras}$, as its electrophoretic mobility is faster than that of either and it was not recognized by an anti-human ras antibody on Western blots. The molecular identity of p21 is presently unknown.

Cyclin D1-Associated p36 is PCNA

Cyclin D1 precipitates of WI38 cells show associated polypeptides of 21 kDa, 31 kDa and 33 kDa and also a prominent protein of 36 kDa (FIG. 1A, lane 5). p36 was not detected in control precipitates, using either pre-immune serum (FIG. 1A, lane 4; FIG. 1B, lane 1) or in 293 lysates (FIG. 1A, lane 2). A 36 kDa protein, in a lower abundance was also detected in CDK2 (FIG. 1A, lane 6), CDK4 (FIG. 1B, lane 3) and CDK5 (FIG. 1C, lane 2) immunoprecipitates, but not in the precipitates with antiserum pre-incubated with competing peptides (FIG. 1C, lane 3).

While attempting to establish the identity of the p36, four observations suggested the possibility that it might be the human proliferating nuclear antigen, PCNA. First, in an asynchronous population of proliferating WI38 cells, cyclin D1 was predominantly a nuclear protein (data not shown), although the distribution is not identical to the speckled pattern of PCNA (Bravo, R. and H. MacDonald-Bravo, *EMBO J.*, 4:655–661 (1985); Madsen, P. and J. E. Celis, *FEBS Lett.*, 193:5–11 (1985). Second, while the level of cyclin D1 is relatively constant in mitogenically activated WI38 cells, the p36 in [$^{35}$S] methionine-labelled cyclin D1 immunoprecipitates was low in quiescent cells and increased at 10–14 hours after stimulation. Ten to fourteen hours after serum stimulation, many WI38 cells are in the late G1, a time which coincides with the onset of PCNA synthesis in serum-stimulated 3T3 fibroblasts (Bravo, R. and H. MacDonald-Bravo, *EMBO J.*, 3:3177–3181 (1984); Celis, J. E. and A. Celis, *Proc. Natl. Acad. Sci., USA*, 82:3262–3268 (1985); Madsen P. and J. E. Celis, *FEBS Lett.*, 193:5–11 (1985). Third, the apparent molecular weight of p36 is similar to that of PCNA (FIG. 1C, lanes 4 and 5). Finally, anti-PCNA antibody precipitated a 35 kDa polypeptide whose electrophoretic mobility is similar to that of p35$^{cyclin\ D1}$ (FIG. 1C, lanes 4 and 5). The identify of the p36 precipitated by the anti-PCNA antibody has been confirmed as PCNA by comparing its V8 peptide map to that of in vitro translated PCNA.

Immunoprecipitation-Western blot experiments were carried out to directly test the possibility that p36 is PCNA. PCNA was readily detected in anti-cyclin D1, cyclin D3, CDK2 and CDK5 immunoprecipitates, but not in the respective control precipitates. In a reciprocal experiment, cyclin D1 and CDK2 were also detected in anti-PCNA immunoprecipitates. It has not been possible to convincingly detect cyclin D3 or CDK5 in PCNA precipitates, possibly due to the low abundance of both proteins in WI38 cells and the relatively poor sensitivity of the D3 and CDK5 antisera in Western blots.

To further assess the similarity between the PCNA and the p36 polypeptide associated with cyclin D1 and CDK2, p36 bands were purified from cyclin D1 and CDK2 immunoprecipitates, separated on SDS-PAGE and their partial V8 proteolytic mapping pattern was compared with that of PCNA. Digestion of cyclin D1-associated p36 by V8 protease revealed the same pattern as that of PCNA derived from anti-PCNA immunoprecipitates and in vitro translated PCNA. Similarly, the digestion patterns of CDK2- and CDK5-associated p36 also match to that of PCNA. The p36 associated with cyclin D1 is PCNA. In addition, proteolytic mapping of the p21 seen in anti-PCNA immunoprecipitate (FIG. 1C, lane 5) showed it to be the same as cyclin D1-associated p21.

Figure 16B:
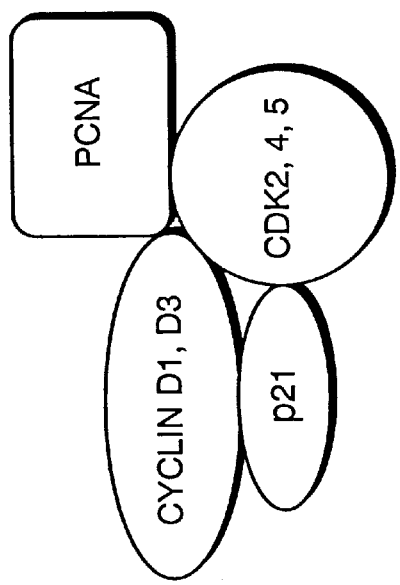
FIGS. 16A and 16B are schematic representations of potential combinational interactions of D-type cyclins, cyclindependent kinases, PCNA and p21.
Figure 16A:
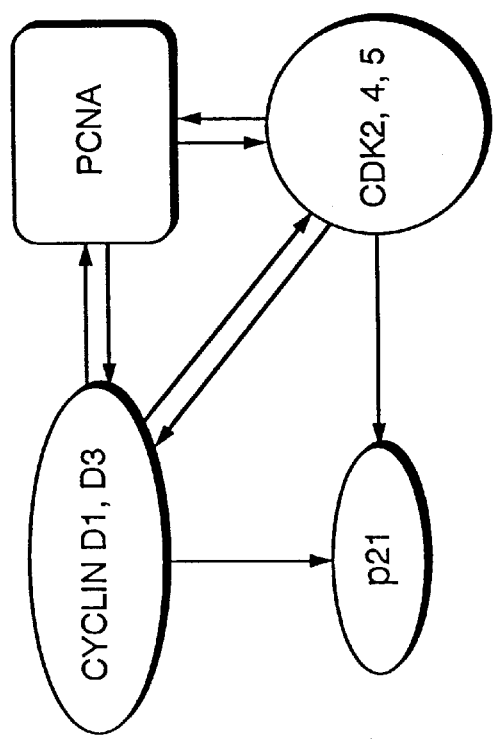

Although the experimental techniques used in this study do not formally allow a distinction between the existence of multiple pair-wise interactions between each protein, the data are most simply explained if D cyclin, PCNA, CDK and p21 form a quaternary complex, as illustrated (FIG. 16B). As judged by the intensity of the methionine-labelled bands in the immunoprecipitation reactions, not all the cyclin D is present in the complex (FIG. 1), nor is all the PCNA (FIGS. 1 and 6). However, the relative intensity of the p36 (PCNA), p33 (CDK4) and p21 bands in an anti-cyclin D precipitate is very similar (FIG. 1A, lane 5; FIG. 1B, lane 2; FIG. 1C, lane 4). The results presented herein do not rule out the possibility that cyclin D, with or without the associated proteins described here, might associate with additional partners in vivo. In particular, two polypeptides that migrate either side of the 97 KD molecular weight marker are apparent in anti-cyclin D precipitation reaction (FIG. 1C, lane 4).

PCNA has been described as an essential accessory factor to the delta polymerase, that is required both for leading-strand DNA replication and also for DNA repair (Prelich, G. et al., *Nature*, 326:517–520 (1987); Prelich G. and B. Stillman, *Cell*, 53:117–126 (1988); Toschi, L. and R. Bravo, *J. Cell Biol.* 107:1623–1628 (1988); M. K. K. Shiviji, et al., *Cell*, 69:367–374 (1992). It localizes in the nucleus at sites of active DNA synthesis and the localization of PCNA, but not its synthesis, is dependent on DNA synthesis. The present studies do not address the specific role of the cyclin D, CDK, PCNA or p21 interactions. It was not possible to detect phosphorylation of any of the respective subunits in in vitro kinase reactions, suggesting that neither PCNA nor p21 is a primary substrate of cyclin D/CDK. Whether cyclin D might be having an activating or inhibitory effect on PCNA functions remains to be determined.

The cyclin D/CDK enzymes that associate with PCNA and p21 might assemble in vivo into a more elaborate multi-protein-DNA synthetic complex, one component of which might be the physiological substrate of cyclin D/CDK. PCNA has generally been biochemically purified from cells in a monomeric form that is unassociated with other proteins (Prelich, G. et al., *Nature* 346:760–763 (1987)). It is possible that the multi-protein complexes described in the present study were over-looked because they do not comprise the majority of the cellular PCNA. Alternatively, it is possible that PCNA has further non-DNA synthetic cell cycle regulatory roles that have not previously been described and that involve cyclin D and CDK proteins. However, the present studies do provide the first biochemical indication of a possible function of D-type cyclins, as modulators of PCNA function.

As represented in FIG. 16B, the present data are most simply explained if there exists, in vivo, a quaternary cyclin D-p21-CDK-PCNA complex. In addition, there are at least three known human D-type cyclins (Inaba, T. et al., *Genomics* 13:565–574 (1992); Xiong, Y. et al., *Genomics* 13:575–584 (1992)) and apparently at least three cyclin D-associated catalytic subunits (CDK2, 4, and 5). All three cyclin D1-associated kinase catalytic subunits, CDK2, CDK4 and CDK5 also associate with cyclin D3. These findings raise the interesting possibility that each of the potential variants of the quaternary complex illustrated in FIG. 16B might exist in vivo. Each might have a subtly different role in the cell cycle or in different cell types.

Uses of the Invention

It is possible, using the methods and materials described herein, to identify genes (DNA or RNA) which encode other cyclins (DNA or RNA which replaces a gene essential for cell cycle start). This method can be used to identify additional members of the cyclin D class or other (non-D type) cyclins of either human or nonhuman origin. This can be done, for example, by screening other cDNA libraries using the budding yeast strain conditional for CLN cyclin expression, described in Example 1, or another mutant in which the ability of a gene to replace cyclin expression can be assessed and used to identify cyclin homologues. This method is carried out as described herein, particularly in Example 1 and as represented in FIG. 1. A cDNA library carried in an appropriate yeast vector (e.g., pADNS) is introduced into a mutant yeast strain, such as the strain described herein (Example 1 and Experimental Procedures). The strain used contains altered CLN genes. In the case of the specific strain described herein, insertional mutations in the CLN1 and CLN2 genes rendered them inactive and alteration of the CLN3 gene allowed for its conditional expression from a galactose-inducible, glucose-repressible promoter; as exemplified, this promoter is a galactose-inducible, glucose-repressible promoter but others can be used.

Mutant yeast transformed with the cDNA library in the expression vector are screened for their ability to grow on glucose-containing medium. In medium containing galactose, the CLN3 gene is expressed and cell viability is maintained, despite the absence of CLN1 and CLN2. In medium containing glucose, all CLN function is lost and the yeast cells arrest in the G1 phase of the cell cycle. Thus, the ability of a yeast transformant to grow on glucose-containing medium is an indication of the presence in the transformant of DNA able to replace the function of a gene essential for cell cycle start. Although not required, this can be confirmed by use of an expression vector, such as pADNS, which contains a selectable marker (the LEU2 marker is present in pADNS). Assessment of the plasmid stability shows whether the ability to grow on glucose-containing medium is the result of reversion or the presence of DNA function (introduction of DNA which replaces the unexpressed or nonfunctional yeast gene(s) essential for cell cycle start). Using this method, cyclins of all types (D type, non-D type) can be identified by their ability to replace CLN3 function when transformants are grown on glucose.

Screening of additional cDNA or genomic libraries to identify other cyclin genes can be carried out using all or a portion of the human D-type cyclin DNAs disclosed herein as probes; for example, all or a portion of the D1, D2 or D3 cDNA sequences of FIGS. 2–4, respectively, or all or a portion of the corresponding genomic sequences described herein can be used as probes. The hybridization conditions can be varied as desired and, as a result, the sequences identified will be of greater or lesser complementarity to the probe sequence (i.e., if higher or lower stringency conditions are used). Additionally, an anti-D type cyclin antibody, such as CYL1 or another raised against D1 or D3 or other human D-type cyclin, can be used to detect other recombinant D-type cyclins produced in appropriate host cells transformed with a vector containing DNA thought to encode a cyclin.

The cyclin-dependent kinase, designated CDK5 and DNA encoding CDK5 are also available as a result of the work described herein. CDK5 has been shown to co-precipitate with D-type cyclin, PCNA and p21 and it is proposed herein that they form a quaternary complex which has a role in vivo in the cell cycle. If this is the case, CDK5 function and/or association with other members of the complex can be altered (enhanced or decreased) in much the same manner as described above for the D-type cyclin. If CDK5 is prevented from binding to D-type cyclin, kinase activation will be prevented. This can be effected as described below. Formation of CDK5—containing quaternary complexes can also be prevented or enhanced, as can formation of complexes containing other CDKs.

Based on work described herein, it is possible to detect altered expression of a D-type cyclin or increased rates of cell division in cells obtained from a tissue or biological sample, such as blood, urine, feces, mucous or saliva. This has potential for use for diagnostic and prognostic purposes since, for example, there appears to be a link between alteration of a cyclin gene expression and cellular transformation or abnormal cell proliferation. For example, several previous reports have suggested the oncogenic potential of altered human cyclin A function. The human cyclin A gene was found to be a target for hepatitis B virus integration in a hepatocellular carcinoma (Wand, J. et al., *Nature* 343:555–557 (1990)). Cyclin A has also been shown to associate with adenovirus E1A in virally infected cells (Giordano, A. et al., *Cell* 58:981–990 (1989); Pines, J. and T. Hunter, *Nature* 346:760–763 (1990)). Further, the PRAD1 gene, which has the same sequence as the cyclin D1 gene, may play an important role in the development of various tumors (e.g., non-parathyroid neoplasia, human breast carcinomas and squamous cell carcinomas) with abnormalities in chromosome 11q13. In particular, identification of CCND1 (PRAD1) as a candidate BCL1 oncogene provides the most direct evidence for the oncogenic potential of cyclin genes. This also suggests that other members of the D-type cyclin family may be involved in oncogenesis. In this context, the chromosomal locations of the CCND2 and CCND3 genes have been mapped to 12p13 and 6p21, respectively. Region 12p13 contains sites of several translocations that are associated with specific immunophenotypes of disease, such as acute lymphoblastic leukemia, chronic myelomoncytic leukemia, and acute myeloid leukemia. Particularly, the isochromosome of the short arm of chromosome 12 [1(12p)] is one of a few known consistent chromosomal abnormalities in human solid tumors and is seen in approximately 90% of adult testicular germ cell tumors. Region 6p21, on the other hand, has been implicated in the manifestation of chronic lymphoproliferative disorder and leiomyoma. Region tp21, the locus of HLA complex, is also one of the best characterized regions of the human genome. Many diseases have been previously linked to the HLA complex, but the etiology of few of these diseases is fully understood. Molecular cloning and chromosomal localization of cyclins D2 and D3 should make it possible to determine whether they are directly involved in these translocations, and if so, whether they are activated. If they prove to be involved, diagnostic and therapeutic methods described herein can be used to assess an individual's disease state or probability of developing a condition associated with or caused by such translocations, to monitor therapy effectiveness (by assessing the effect of a drug or drugs on cell proliferation) and to provide treatment.

The present invention includes a diagnostic method to detect altered expression of a cyclin gene, such as cyclin D1, D2, D3 or another D-type cyclin. The method can be carried out to detect altered expression in cells or in a biological sample. As shown herein, there is high sequence similarity among cyclin D genes, which indicates that different members of D-type cyclins may use similar mechanisms in regulating the cell cycle (e.g., association with the same catalytic subunit and acting upon the same substrates). The fact that there is cell-type-specific differential expression, in both mouse and human cells, makes it reasonable to suggest that different cell lineages or different tissues may use different D-type cyclins to perform very similar functions and that altered tissue-specific expression of cyclin D genes as a result of translocation or other mutational events may contribute to abnormal cell proliferation. As described herein, cyclin D1 is expressed differentially in tissues analyzed; in particular, it has been shown to be expressed at the highest levels in cells of neural origin (e.g., glioblastoma cells). Other D-type cyclins are also expressed differentially among various cell types and further, are differentially expressed even within the same type of cells, depending on the differentiation state. For example, cyclin D2 is differentially expressed in two different T-cell lines which represent distinct stages of T-cell differentiation. In addition, Applicant has shown that expression of D-type cyclin genes correlates with the state of cell growth using human diploid fibroblasts. Thus, differential diagnosis is also possible, in that the type of D cyclin whose function is altered can be determined and a therapeutic agent or drug targeted to that D-type cyclin can be administered, resulting in selective treatment. For example, in those instances where cyclin D1 function is altered, which might be the case in oncogenesis (e.g., in some leukemias and solid tumors), altered cyclin D1 function can be detected and treatment instituted accordingly. This can take the form of administration of a therapeutic agent which specifically inhibits cyclin D1 activity and, thus, specifically inhibits further cell division in those cells in which cyclin D1 is the controlling D-type cyclin. It is possible to combine a drug which specifically alters cyclin D1 function with another agent, such as an antibody, to further target cells in which the anti-cyclin D1 drug is to have its effect. For example an anti-cyclin D1 drug (e.g., an antibody which binds cyclin D1, a peptide which mimics a peptide to which cyclin D1 normally binds) can be attached to a targeting molecule, such as an antibody specific for a marker, such as a cell surface receptor, on cells in which cyclin D1 activity is to be altered. The resulting anti-cyclin D1 drug—targeting molecule conjugate provides specificity in two ways: it delivers an anti-cyclin D1 drug to a specific cell type or types. It is also possible to detect altered D-type cyclin expression and function in a generic sense as well (e.g., to detect all D-type cyclins or a combination of two or more selected D-type cyclins whose altered functions are associated with a condition or disease to be diagnosed).

As a result of the work described herein, D-type cyclin expression can be detected and/or quantitated and results used as an indicator of normal or abnormal (e.g., abnormally high rate of) cell division. Differential expression (either expression in various cell types or of one or more of the types of D cyclins) can also be determined.

In a diagnostic method of the present invention, cells obtained from an individual are processed in order to render nucleic acid sequences in them available for hybridization with complementary nucleic acid sequences. All or a portion of the D1, D2 and/or D3 cyclin (or other D-type cyclin gene) sequences can be used as a probe(s). Such probes can be a portion of a D-type cyclin gene; such a portion must be of sufficient length to hybridize to complementary sequences in a sample and remain hybridized under the conditions used and will generally be at least six nucleotides long. Hybridization is detected using known techniques (e.g., measurement of labeled hybridization complexes, if radiolabeled or fluorescently labeled oligonucleotide probed are used). The extent to which hybridization occurs is quantitated; increased levels of the D-type cyclin gene is indicative of increased potential for cell division.

Alternatively, the extent to which a D-type cyclin (or cyclins) is present in cells, in a specific cell type or in a body fluid can be determined using known techniques and an antibody specific for the D-type cyclin(s). In a third type of diagnostic method, complex formation between the D-type cyclin and the protein kinase with which it normally or typically complexes is assessed, using exogenous substrate, such as histone Hl, as a substrate. Arion, D. et al., *Cell*, 55:371–378 (1988). In each diagnostic method, comparison of results obtained from cells or a body fluid being analyzed with results obtained from an appropriate control (e.g., cells of the same type known to have normal D-type cyclin levels and/or activity or the same body fluid obtained from an individual known to have normal D-type cyclin levels and/or activity) is carried out. Increased D-type cyclin levels and/or activity may be indicative of an increased probability of abnormal cell proliferation or oncogenesis or of the actual occurrence of abnormal proliferation or oncogenesis. It is also possible to detect more than one type of cyclin (e.g., A, B, and/or D) in a cell or tissue sample by using a set of probes (e.g., a set of nucleic acid probes or a set of antibodies), the members of which each recognize and bind to a selected cyclin and collectively provide information about two or more cyclins in the tissues or cells analyzed. Such probes are also the subject of the present invention; they will generally be detectably labelled (e.g., with a radioactive label, a fluorescent material, biotin or another member of a binding pair or an enzyme).

A method of inhibiting cell division, particularly cell division which would otherwise occur at an abnormally high rate, is also possible. For example, increased cell division is reduced or prevented by introducing into cells a drug or other agent which can block, directly or indirectly, formation of the protein kinase-D type cyclin complex and, thus, block activation of the enzyme. In one embodiment, complex formation is prevented in an indirect manner, such as by preventing transcription and/or translation of the D-type cyclin DNA and/or RNA. This can be carried out by introducing antisense oligonucleotides into cells, in which they hybridize to the cyclin-encoding nucleic acid sequences, preventing their further processing. It is also possible to inhibit expression of the cyclin by interfering with an essential D-type transcription factor. There are reasons to believe that the regulation of cyclin gene transcription may play an important role in regulating the cell cycle and cell growth and oscillations of cyclin mRNA levels are critical in controlling cell division. The G1 phase is the time at which cells commit to a new round of division in response to external and internal sequences and, thus, transcription factors which regulate expression of G1 cyclins are surely important in controlling cell proliferation. Modulation of the transcription factors is one route by which D-type cyclin activity can be influenced, resulting, in the case of inhibition or prevention of function of the transcription factor(s), in reduced D-type cyclin activity. Alternatively, complex formation can be prevented indirectly by degrading the D-type cyclin(s), such as by introducing a protease or substance which enhances cyclin breakdown into cells. In either case, the effect is indirect in that less D-type cyclin is available than would otherwise be the case.

In another embodiment, protein kinase-D type cyclin complex formation is prevented in a more direct manner by, for example, introducing into cells a drug or other agent which binds the protein kinase or the D-type cyclin or otherwise interferes with the physical association between the cyclin and the protein kinase it activates (e.g., by intercalation) or disrupts the catalytic activity of the enzyme. This can be effected by means of antibodies which bind the kinase or the cyclin or a peptide or low molecular weight organic compound which, like the endogenous D-type cyclin, binds the protein kinase, but whose binding does not result in activation of the enzyme or results in its being disabled or degraded. Peptides and small organic compounds to be used for this purpose can be designed, based on analysis of the amino acid sequences of D-type cyclins, to include residues necessary for binding and to exclude residues whose presence results in activation. This can be done, for example, by systematically mapping the binding site(s) and designing molecules which recognize or otherwise associate with the site(s) necessary for activation, but do not cause activation. As described herein, there is differential expression in tissues of D-type cyclins. Thus, it is possible to selectively decrease mitotic capability of cells by the use of an agent (e.g., an antibody or anti-sense or other nucleic acid molecule) which is designed to interfere with (inhibit) the activity and/or level of expression of a selected type (or types) of D cyclin. For example, in treating tumors involving the central nervous system or other non-hematopoietic tissues, agents which selectively inhibit cyclin D1 might be expected to be particularly useful, since D1 has been shown to be differentially expressed (expressed at particularly high levels in cells of neural origin).

Formation of complexes of D-type cyclin, CDK, PCNA and p21 can also be prevented in a similar manner as that described above for inhibiting protein kinase D-type cyclin complex formation. That is, complex formation can be prevented directly (e.g., by means of a drug or agent which binds a component of the complex or otherwise interferes with the physical association of complex components. Complex formation can also be prevented in an indirect manner, such as by preventing transcription and/or translation of DNA and/or RNA encoding a component of the complex, in a similar manner to that described above for blocking D-type cyclin—protein kinase complex formation. Alternatively, complex formation can be prevented indirectly by degrading one or more of its constituents.

Direct inhibition of complex formation can be effected in a variety of ways. Because of the fact that D-type cyclins are differentially expressed in different cell types and at various stages in the cell cycle and that there are numerous combinatorial variations of the quaternary cyclin-containing complex, inhibition can be specific in nature and the agent or drug used can be selected to inhibit the cell cycle (cell proliferation) in a particular cell type and/or at a particular phase of proliferation. For example, a drug which selectively inhibits cyclin D1 can be used to inhibit proliferation of cells (e.g., cells of neural origin) in which it is expressed at high levels.

Alternatively, a drug which selectively inhibits cyclin D2 or cyclin D3 function or its ability to form a quaternary complex can be used. Each of the other complex constituents is also a target whose function or availability for complex formation can be altered. For example, CDK2, CDK4, CDK5 and other cyclin dependent kinases which complex with a D-type cyclin can be inhibited or enhanced, either in terms of their function or their availability for incorporation into the quaternary complex. Drugs or agents which alter PCNA function or availability and drugs or agents which alter p21 function or availability can also be used to inhibit or enhance cell division. In the case of each quaternary complex constituent, it is possible to introduce into cells an agent, such as a small peptide or other organic molecule, which mimics the complex constituent in terms of binding but lacks its active region(s), which results in formation of complexes lacking the activity or interactions of the normally-produced complex.

Direct inhibition of complex formation can also be non-specific (i.e., can affect the majority of cells or all cells in which the D-type cyclin-containing quaternary complex is formed). This can be done, for example, by introducing into cells a drug which inhibits function or availability of a common component of the quaternary complex (e.g., PCNA) or by introducing a mixture or cocktail of drugs, which together inhibit all D-type cyclins.

Alternatively, indirect inhibition of quaternary complex is possible. That is, a drug or agent which acts to cause less of a complex constituent (e.g., D-type cyclin, CDK, PCNA or p21) available can be used. Such drugs or agents include those, such as anti-sense oligonucleotides, which block transcription or translation and those, such as an enzyme, which degrade complex constituents, either prior to or after their incorporation into a quaternary complex.

Drugs or agents useful in the present method of altering, particularly inhibiting, cell cycle start and, thus, cell division, can be existing compounds or molecules (e.g., small organic molecules, anti-sense oligonucleotides, and inorganic substances) or materials designed for use in the present method. In either case, such drugs can be identified by the method of the present invention.

Once an appropriate drug or agent has been identified, it can be administered to an individual, particularly a human or other vertebrate, by any route effective in introducing the drug or agent into cells in sufficient quantity to have the desired effect (i.e., alteration of cell division). For example, a selected drug can be administered intravenously, intramuscularly, by direct injection into a tumor, via the gastrointestinal tract (e.g., orally), intraperitoneally or intra-nasally. In some cases, ex vivo administration is appropriate (e.g., in instances where blood or bone marrow is removed from the body, treated and returned to the body).

Generally, the drug or agent used to alter cell division will be included in a formation which can also include a physiological carrier (e.g., a buffer or physiological saline), stabilizers, an adjuvant, and flavoring agents. The quantity of the drug to be administered can be determined empirically and will vary depending on considerations such as the age, weight and height of the recipient and the severity of the condition to be treated.

Antibodies specifically reactive with D-type cyclins of the present invention can also be produced, using known methods. For example, anti-D type cyclin antisera can be produced by injecting an appropriate host (e.g., rabbits, mice, rats, pigs) with the D-type cyclin against which anti sera is desired and withdrawing blood from the host animal after sufficient time for antibodies to have been formed. Monoclonal antibodies can also be produced using known techniques. Sambrook, J. et al., *Molecular Cloning: A Laboratory Manual*, Cold Spring Harbor Laboratory, Cold Spring Harbor, N.Y. (1989); Hallow, E. and D. Lane, *Antibodies: A Laboratory Manual*, Cold Spring Harbor Press, New York (1988). Antibodies specifically reactive with CDK5, can also be produced using known methods. The present invention also includes a method of screening compounds or molecules for their ability to inhibit or suppress the function of a cyclin, particularly a D-type cyclin. For example, mutant cells as described herein, in which a D-type cyclin such as D1 or D3, is expressed, can be used. A compound or molecule to be assessed for its ability to inhibit a D-type cyclin is contacted with the cells, under conditions appropriate for entry of the compound or molecule into the cells. Inhibition of the cyclin will result in arrest of the cells or a reduced rate of cell division. Comparison of the rate or extent of cell division in the presence of the compound or molecule being assessed with cell division of an appropriate control (e.g., the same type of cells without added test drug) will demonstrate the ability or inability of the compound or molecule to inhibit the cyclin. Existing compounds or molecules (e.g., those present in a fermentation broth or a chemical "library") or those developed to inhibit the cyclin activation of its protein kinase can be screened for their effectiveness using this method. Drugs which inhibit D-type cyclin are also the subject of this invention.

The present invention also includes a method of screening compounds or molecules for their ability to alter formation of the quaternary complex described herein. This method is carried out in much the same way as the method, described above, for identifying compounds or molecules which inhibit a D-type cyclin. In the subject method, the compound or molecule to be tested and cells in which D-type cyclin-containing complex is formed are combined, under conditions appropriate for complex formation to occur and entry into cells of the compound or molecule being tested. Complex formation can be determined, as described herein. Inhibition of a complex constituent or of complex formation will result in arrest of the cells or a reduced rate of cell division. Comparison of the rate or extent of cell division in the presence of the compound or molecule being tested with the rate or extent in the absence of the compound or molecule will demonstrate whether it has an effect on cell division (i.e., division to a lesser extent in the presence of the compound or molecule tested than in its absence is an indication the compound or molecule is an inhibitor). Drugs or agents which inhibit complex formation and, as a result, cell division, are also the subject of this invention.

The present invention will now be illustrated by the following examples, which are not intended to be limiting in any way.

EXAMPLES

Experimental procedures for Examples 1–3 are presented after Example 3.

Example 1
Identification of Human cDNA Clones that Rescue CLN Deficiency

In *S. cerevisiae*, there are three Cln proteins. Disruption of any one CLN gene has little effect on growth, but if all three CLN genes are disrupted, the cells arrest in G1 (Richardson, H. E. et al., *Cell* 59:1127–1133 (1989)). A yeast strain was constructed, as described below, which contained insertional mutations in the CLN1 and CLN2 genes to render them inactive. The remaining CLN3 gene was further altered to allow for conditional expression from the galactose-inducible, glucose-repressible promoter GAL1 (see FIG. 1). The strain is designated 305–15d #21. In medium containing galactose the CLN3 gene is expressed and despite the absence of both CLN1 and CLN2, cell viability is retained (FIG. 1). In a medium containing glucose, all CLN function is lost and the cells arrest in the G1 phase of the cell cycle.

A human glioblastoma cDNA library carried in the yeast expression vector pADNS (Colicelli, J. et al., *Pro. Natl.*

Acad. Sci. USA 86:3599–3603 (1989)) was introduced into the yeast. The vector pADNS has the LEU2 marker, the 2μ replication origin, and the promoter and terminator sequences from the yeast alcohol dehydrogenase gene (FIG. 1). Approximately $3 \times 10^6$ transformants were screened for the ability to grow on glucose containing medium. After 12 days of incubation, twelve colonies were obtained. The majority of these proved to be revertants. However, in two cases, the ability to grow on glucose correlated with the maintenance of the LEU2 marker as assessed by plasmid stability tests. These two yeast transformants carried plasmids designated pCYCD1-21 and pCYCD1-19 (see below). Both were recovered in E. coli. Upon reintroduction into yeast, the plasmids rescued the CLN deficient strain, although the rescue was inefficient and the rescued strain grew relatively poorly.

The restriction map and partial DNA sequence analysis revealed that pCYCD1-19 and pCYCD1-21 were independent clones representing the same gene. The 1.2 kb insert of pCYCD1-21 was used as probe to screen a human HeLa cDNA library for a full length cDNA clone. Approximately 2 million cDNA clones were screened and 9 positives were obtained. The longest one of these clones, pCYCD1-H12 (1325 bp), was completely sequenced (FIG. 2). The sequence exhibits a very high GC content within the coding region (61%) and contains a poly A tail (69 A residues). The estimated molecular weight of the predicted protein product of the gene is 33,670 daltons starting from the first in-frame AUG codon at nucleotide 145 (FIG. 2). The predicted protein is related to other cyclins (see below) and has an unusually low pI of 4.9 (compared to 6.4 of human cyclin A, 7.7 of human cyclin B and 5.6 of CLN1), largely contributed by the high concentration of acidic residues at its C-terminus.

There are neither methionine nor stop codons 5' to the predicted initiating methionine at nucleotide 145. Because of this and also because of the apparent N-terminal truncation of CYCD1 with respect to other cyclins (see below for more detail), four additional human cDNA libraries were further screened to see if the λCYCD1-H12 clone might lack the full 5' region of the cDNA. Among more than 100 cDNA clones isolated from these screens, none was found that had a more extensive 5' region than that of λCYCD1-H12. The full length coding capacity of clone H12 was later confirmed by Western blot analysis (see below).

CYCD1 encodes the smallest (34 kd) cyclin protein identified so far, compared to the 49 kd human cyclin A, 50 kd human cyclin B and 62 kd S. cerevisiae CLN1. By comparison with A and B type cyclins, the difference is due to the lack of almost the entire N-terminal segment that contains the so called "destruction box" identified in both A and B type cyclins (Glotzer, M. et al., Nature 349:132–138 (1991)).

Sequence Analysis of D1 and Comparison with Other Cyclins

Sequence analysis revealed homology between the CYCD1-H12 encoded protein and other cyclins. However, it is clear that CYCD1 differs from the three existing classes of cyclins, A, B and CLN. To examine how this new cyclin gene might be evolutionary related to other cyclins, a comprehensive amino acid sequence comparison of all cyclin genes was conducted. Fifteen previously published cyclin sequences as well as CYCD1 were first aligned using a strategy described in detail by Xiong and Eickbush (Xiong, Y. and T. H. Eickbush, EMBO J. 9:3353–3362 (1990)). Effort was made to reach the maximum similarity between sequences with the minimum introduction of insertion/deletions and to include as much sequence as possible. With the exception of CLN cyclins, this alignment contains about 200 amino acids residues which occupies more than 70% of total coding region of CYCD1 (FIG. 5A). There is a conserved domain and some scattered similarities between members of A and B type cyclins N-terminal to the aligned region (Glotzer, M. et al., Nature 349:132–138 (1991)), but this is not present in either CLN cyclins or CYCD1 and CYL1 and so they were not included in the alignment.

The percent divergence for all pairwise comparisons of the 17 aligned sequences was calculated and used to construct an evolutionary tree of cyclin gene family using the Neighbor-Joining method (Saitou, N. and M. Nei, Mol. Biol. Evol. 4:406–425 (1987) and Experimental Procedures). Because of the lowest similarity of CLN cyclins to the other three classes, the tree (FIG. 5B) was rooted at the connection between the CLN cyclins and the others. It is very clear from this evolutionary tree that CYCD1, CYCD2 and CYCD3 represent a distinct new class of cyclin, designated cyclin D.

Example 2

Expression of the Cyclin D1 Gene in Human Cells

Expression of cyclin D1 gene in human cells was studied by Northern analysis. Initial studies indicated that the level of cyclin D1 expression was very low in several cell lines. Poly (A)+RNA was prepared from HeLa cells and probed with the entire coding region of CYCD1 gene. Two major transcripts of 4.8 kb and 1.7 kb were detected. The high molecular weight form was the most abundant. With the exception of a few cDNA clones, which were truncated at either the 5' or 3' ends, most of the cDNA clones isolated from various different cDNA libraries are very similar to the clone λCYCD1-H12 (FIG. 2). Thus, it appears that the 1.7 kb transcript detected in Northern blots corresponds to nucleotide sequence in FIG. 2.

To understand the origin of the larger 4.8 kb transcript, both 5' and 3' end sub-fragments of the λCYCD1-H12 clone were used to screen both cDNA and genomic libraries, to test whether there might be alternative transcription initiation, polyadenylation and/or mRNA splicing. Two longer cDNA clones, λCYCD1-H034 (1.7 kb) from HeLa cells and λDYDC1-T078 (4.1 kb) from human teratocarcinoma cells, as well as several genomic clones were isolated and partially sequenced. Both λCYCD1-H034 and λCYCD1-T078 have identical sequences to λCYCD1-H12 clone from their 5' ends (FIG. 6). Both differ from λCYCD1-H12 in having additional sequences at the 3' end, after the site of polyadenylation. These 3' sequences are the same in λCYCD1-H034 and λCYCD1-T078, but extend further in the latter clone (FIG. 6). Nucleotide sequencing of a genomic clone within this region revealed colinearity between the cDNAs and the genomic DNA (FIG. 6). There is a single base deletion (an A residue) in λCYCD1-T078 cDNA clone. This may be the result of polymorphism, although it is not possible to exclude the possibility that some other mechanism is involved. The same 4.8 kb transcript, but not the 1.7 kb transcript, was detected using the 3' end extra fragment from clone T078 as a probe.

It appears that the two mRNAs detected in Northern blots arise by differential polyadenylation (FIG. 6). Strangely, there is no recognizable polyadenylation sequence (AAUAAA) anywhere within the sequence of clone λCYCD1-H12, even though polyadenylation has clearly occurred (FIG. 2). There is also no close variant of AAUAAA (nothing with less than two mismatches).

Example 3
Differential Expression of Cyclin D1 Gene in Different Cell Types

During the screening of cDNA libraries to obtain full length clones of CYCD1, it became evident that the cDNA library derived from the human glioblastoma cell line (U118 MG) from which the yeast transformants were obtained gave rise to many more positives than the other four cDNA libraries. Northern and Western blotting were carried out to explore the possibility that cyclin D1 might be differentially expressed in different tissues or cell lines. Total RNA was isolated from U118 MG cells and analyzed by Northern blot using the CYCD1 gene coding region as probe. The level of transcript is 7 to 10 fold higher in the glioblastoma cells, compared to HeLa cells. In both HeLa and U118 MG cells, both high and low molecular weight transcripts are observed.

To investigate whether the abundant CYCD1 message in the U118 MG cell line is reflected at the protein level, cell extracts were prepared and Western blotting was performed using anti-CYL1 prepared against mouse CYL1 (provided by Matsushime, H. et al.). This anti-CYL1 antibody was able to detect nanogram quantities of recombinant CYCD1 on Western blots (data not shown), and was also able to detect CYCD1 in the original yeast transformants by immunoprecipitation and Western analysis. Initial experiments using total cell extracts, from HeLa, 293 or U118 MG cells failed to detect any signal. However, if the cell extracts were immunoprecipitated with the serum before being subjected to SDS-PAGE and immunoblotting, a 34 kd polypeptide was readily detected in U118 MG cells. The protein is far less abundant in HeLa cells and was not detectable in 293 cells. The molecular weight of the anti-CYCL1 crossreactive material from U118 MG and HeLa is exactly that of the human CYCD1 protein expressed in *E. coli*. This argues that the sequenced cDNA clones contain the entire open reading frame.

EXPERIMENTAL PROCEDURES
Strain Construction

The parental strain was BF305-15d (MATa leu2-3 leu2-112 his3-11 his3-15 ura3-52 trp1 ade1 met14 arg5,6) (Futcher, B. and J. Carbon, *Mol. Cell. Biol.* 6:2213–2222 (1986)). The strain was converted into a conditional cln- strain in three steps. First, the chromosomal CLN3 gene was placed under control of the GAL1 promoter. A 0.75 kb EcoRI-BamHI fragment containing the bidirectional GAL10-GAL1 promoters was fused to the 5' end of the CLN3 gene, such that the BamHI (GAL1) end was attached 110 nucleotides upstream of the CLN3 start codon. An EcoRI fragment stretching from the GAL10 promoter to the middle of CLN3 (Nash, R. et al., *EMBO J.* 7:4335–4346 (1988)) was then subcloned between the XhoI and EcoRI sites of pBF30 (Nash, R. et al., *EMBO J.* 7:4335–4346 (1988)). The ligation of the XhoI end to the EcoRI end was accomplished by filling in the ends with Klenow, and blunt-end ligating (destroying the EcoRI site). As a result, the GAL1 promoter had replaced the DNA normally found between −110 and −411 upstream of CLN3. Next, an EcoRI to SphI fragment was excised from this new pBF30 derivative. This fragment had extensive 5' and 3' homology to the CLN3 region, but contained the GAL1 promoter and a URA3 marker just upstream of CLN3. Strain BF305-15d was transformed with this fragment and Ura+ transformants were selected. These were checked by Southern analysis. In addition, average cell size was measured when the GAL1 promoter was induced or uninduced. When the GAL1 promoter was induced by growing the cells in 1% raffinose and 1% galactose, mode cell volume was about 25 $\mu m^3$ (compared to a mode volume of about 40 $\mu m^3$ for the parental strain) whereas when the promoter was not induced (raffinose alone), or was repressed by the presence of glucose, cell volume was much larger than for the wildtype strain. These experiments showed that CLN3 had been placed under control of the GAL1 promoter. It is important to note that this GAL1-controlled, glucose repressible gene is the only source of CLN3 protein in the cell.

Second, the CLN1 gene was disrupted. A fragment of CLN1 was obtained from I. Fitch, and used to obtain a full length clone of CLN1 by hybridization, and this was subcloned into a pUC plasmid. A BamHI fragment carrying the HIS3 gene was inserted into an NcoI site in the CLN1 open reading frame. A large EcoRI fragment with extensive 5' and 3' homology to the CLN1 region was then excised, and used to transform the BF305-15d GAL-CLN3 strain described above. Transformation was done on YNB-his raffinose galactose plates. His+ clones were selected, and checked by Southern analysis.

Finally, the CLN2 gene was disrupted. A fragment of CLN2 was obtained from I. Fitch, and used to obtain a full length clone of CLN2 by hybridization, and this was subcloned into a pUC plasmid. An EcoRI fragment carrying the TRP1 gene was inserted into an SpeI site in the CLN2 open reading frame. A BamHI-KpnI fragment was excised and used to transform the BF305-15d GAL-CLN3 HIS3::cln1 strain described above. Transformation was done on YNB-trp raffinose galactose plates. Trp+ clones were selected. In this case, because the TRP1 fragment included an ARS, many of the transformants contained autonomously replicating plasmid rather than a disrupted CLN2 gene. However, several percent of the transformants were simple TRP1::cln2 disruptants, as shown by phenotypic and Southern analysis.

One particular 305 -15d GAL1-CLN3 HIS3::cln1 TRP1::cln2 transformant called clone #21 (referred to hereafter as 305-15d #21) was analyzed extensively. When grown in 1% raffinose and 1% galactose, it had a doubling time indistinguishable from the CLN wild-type parental strain. However, it displayed a moderate Wee phenotype (small cell volume), as expected for a CLN3 overexpressor. When glucose was added, or when galactose was removed, cells accumulated in G1 phase, and cell division ceased, though cells continued to increase in mass and volume. After overnight incubation in the G1-arrested state, essentially no budded cells were seen, and a large proportion of the cells had lysed due to their uncontrolled increase in size.

When 305-15d #21 was spread on glucose plates, revertant colonies arose at a frequency of about 10-7. The nature of these glucose-resistant, galactose-independent mutants was not investigated.

Yeast Spheroplasts Transformation

*S. cerevisiae* spheroplasts transformation was carried out according to Burgers and Percival and Allshire (Burgers, P. M. J. and K. J. Percival, *Anal. Biochem.* 163:391–397 (1987); Allshire, R. C., *Proc. Natl. Acad. Sci. USA* 87:40433–4047 (1990)).

Cell Culture

HeLa and 293 cells were cultured at 37-C either on plates or in suspension in Dulbecco's modified Eagle's medium (DMEM) supplemented with 10% fetal calf serum. Glioblastoma U118 MG cells were cultured on plates in DMEM supplemented with 15% fetal bovine serum and 0.1 mN non-essential amino acid (GIBCO).

Nucleic Acid Procedures

Most molecular biology techniques were essentially the same as described by Sambrook et al. (Sambrook, J. et al.,

*Molecular Cloning: A Laboratory Manual* Cold Spring Harbor Laboratory, Cold Spring Harbor, N.Y. (1989)). Phagmid vectors pUC118 or pUC119 (Vieira, J. and J. Messing, et al. *Meth. Enzymol.* 153:3–11 (1987)) or pBlueScript (Stratagene) were used as cloning vectors. DNA sequences were determined either by a chain termination method (Sanger, F. et al. *Proc. Natl. Acad. Sci. USA* 74:5463–5467 (1977)) using Sequenase Kit (United States Biochemical) or on an Automated Sequencing System (373A, Applied Biosystems).

Human HeLa cell cDNA library in λZAP II was purchased from Stratagene. Human T cell cDNA library in λgtl0 was a gift of M. Gillman (Cold Spring Harbor Laboratory). Human glioblastoma U118 MG and glioblastoma SW1088 cell cDNA libraries in λZAP II were gifts of M. Wigler (Cold Spring Harbor Laboratory). Human teratocarcinoma cell cDNA library λgtl0 was a gift of Skowronski (Cold Spring Harbor Laboratory). Normal human liver genomic library λGEM-11 was purchased from Promega.

Total RNA from cell culture was extracted exactly according to Sambrook et al. (Sambrook, J. et al., *Molecular Cloning: A Laboratory Manual* Cold Spring Harbor Laboratory, Cold Spring Harbor, N.Y. (1989)) using guanidium thiocyanate followed by centrifugation in CsCl solution. Poly(A)+RNA was isolated from total RNA preparation using Poly (A)+Quick push columns (Stratagene). RNA samples were separated on a 1% agaroseformaldehyde-MOPS gel and transferred to a nitrocellulose filter. Northern hybridizations (as well as library screening) were carried out at 68° C. in a solution containing 5×Denhardt's solution, 2×SSC, 0.1% SDS, 100 μg/ml denatured Salmon sperm DNA, 25 μM $NaPO_4$ (pH7.0) and 10% dextran sulfate. Probes were labelled by the random priming labelling method (Feinberg, A. and B. Vogelstein, *Anal. Biochem.* 132:6–13 (1983)). A 1.3 kb Hind III fragment of cDNA clone pCYCD1-H12 was used as coding region probe for Northern hybridization and genomic library screening, a 1.7 kb Hind III-EcoRI fragment from cDNA clone pCYCD1-T078 was used as 3' fragment probe.

To express human cyclin D1 gene in bacteria, a 1.3 kb Nco I-Hind II fragment of pCYCD1-H12 containing the entire CYCD1 open reading frame was subcloned into a T7 expression vector (pET3d, Studier, F. W. et al., *Methods in Enzymology* 185:60–89 (1990)). Induction of *E. coli* strain BL21 (DE3) harboring the expression construct was according to Studier (Studier, F. W. et al., *Methods in Enzymology* 185:60–89 (1990)). Bacterial culture was lysed by sonication in a lysis buffer (5 mM EDTA, 10% glycerol, 50 mM Tris-HCL, pH 8.0, 0.005% Triton X-100) containing 6 M urea (CYCD1 encoded p34 is only partial soluble in 8 M urea), centrifuged for 15 minutes at 20,000 g force. The pellet was washed once in the lysis buffer with 6 M urea, pelleted again, resuspended in lysis buffer containing 8 M urea, and centrifuged. The supernatant which enriched the 34 kd CYCD1 protein was loaded on a 10% polyacrymide gel. The 34 kd band was cut from the gel and eluted with PBS containing 0.1% SDS.

Sequence Alignment and Formation of an Evolutionary Tree

Protein sequence alignment was conducted virtually by eye according to the methods described and discussed in detail by Xiong and Eickbush (Xiong, Y. and T. H. Eickbush, *EMBO J.* 9:3353–3362 (1990)). Numbers within certain sequences indicate the number of amino acid residues omitted from the sequence as the result of insertion.

Numbers within certain sequences indicate the number of amino acid residues omitted from the sequence as the result of insertion (e.g., for CLN1, . . . TWG25RLS . . . indicates that 25 amino acids have been omitted between G and R). Sources for each sequence used in this alignment and in the construction of an evolutionary tree (FIG. 5B) are as follows: CYCA-Hs, human A type cyclin (Wang, J. et al., *Nature* 343:555–557 (1990)); CYCA-X1, Xenopus A-type cyclin (Minshull, J. et al., EMBO J. 9:2865–2875 (1990)); CYCA-Ss, clam A-type cyclin (Swenson, R. I. et al., *Cell* 47:867–870 (1986); CYCA-Dm, Drosophila A-type cyclin (Lehner, C. F. and P. H. O'Farrell, *Cell* 56:957–968 (1989)); CYCB1-Hs, human B1-type cyclin (Pines, J. and T. Hunter, *Cell* 58:833–846 (1989)); CYCB1-X1 and CYCB2-X1, Xenopus B1- and B2-type cyclin (Minshull, J. et al., *Cell* 56:947–956 (1989)); CYCB-Ss, clam B-type cyclin (Westendorf, J. M. et al., *J. Cell Biol.* 108:1431–1444 (1989)); CYCB-Asp, starfish B-type cyclin (Tachibana, K. et al., *Dev. Biol.* 140:241–252 (1990)); CYCB-Arp, sea urchin B-type cyclin (Pines, J. and T. Hunter, *EMBO J.* 6:2987–2995 (1987)); CYCB-Dm, Drosophila B-type cyclin (Lehner, C. F. and P. H. O'Farrell, *Cell* 61:535–547 (1990)); CDC13-Sp, *S. pombe* CDC13 (Booher, R. and D. Beach, *EMBO J.* 7:2321–2327 (1988)); CLN1-Sc and CLN2-Sc, *S. cerevisiae* cyclin 1 and 2 (Hadwiger, J. A. et al., *Proc. Natl. Acad. Sci. USA* 86:625–5–6259 (1989)); CLN3-Sc, *S. cerevisiae* cyclin 3 (Nash, R. et al., *EMBO J.* 7:43354346 (1988)).

A total of 17 cyclin sequences were aligned and two representative sequences from each class are presented in FIG. 5A.

Percent divergence of all pairwise comparison of 17 sequences were calculated from 154 amino acid residues common to all 17 sequences, which does not include the 50 residue segments located at N-terminal part of A, B and D-type cyclins because of its absence from CLN type cyclins. A gap/insertion was counted as one mismatch regardless of its size. Before tree construction, all values were changed to distance with Poisson correction ($d = -\log_e S$, where the S=sequence similarity (Nei, M., *Molecular Evolutionary Genetics* pp. 287–326 Columbia University Press, NY (1987)). Calculation of pairwise comparison and Poisson correction were conducted using computer programs developed at University of Rochester. Evolutionary trees of cyclin gene family was generated by the Neighbor-Joining program (Saitou, N. and M. Nei, *Mol. Biol. Evol.* 4:406–567 (1987)). All calculations were conducted on VAX computer MicroVMS V4.4 of Cold Spring Harbor Laboratory. The reliability of the tree was evaluated by using a subset sequence (e.g., A, B and D-type cyclins), including more residues (e.g., the 50-residue segment located at C-terminal of A, B and D-type cyclins, FIG. 5A) or adding several other unpublished cyclin sequences. They all gave rise to the tree with the same topology as the one presented in FIG. 5B.

Immunoprecipitation and Western Blots

Cells from 60 to 80% confluent 100 mm dish were lysed in 1 ml of lysis buffer (50 mM Tris-HCl, pH 7.4, 150 mM NaCl, 20 mM EDTA, 0.5% NP-40, 0.5% Nadeoxycholate, 1 mM PMSF) for 30 minutes on ice. Immunoprecipitation was carried out using 1 mg protein from each cell lysate at 4° C. for overnight. After equilibrated with the lysis buffer, 60 μl of Protein A-agarose (PIERCE) was added to each immunoprecipitation and incubated at 4° C. for 1 hour with constant rotating. The immunoprecipitate was washed three times with the lysis buffer and final resuspended in 50 μl 2×SDS protein sample buffer, boiled for 5 minutes and loaded onto a 10% polyacrymide gel. Proteins were transferred to a nitrocellulose filter using a SDE Electroblotting System (Millipore) for 45 minutes at a constant current of 400 mA. The filter was blocked for 2 to 6 hours with 1×PBS, 3% BSA and 0.1% sodium azide, washed 10 minutes each time and 6 times with NET gel buffer (50 mM Tris-HCl, pH 7.5, 150 mM NaCl, 0.1% NP-40, 1 mM EDTA, 0.25% gelatin and 0.02 sodium azide), radiolabelled with 125I-Protein A for 1 hour in blocking solution with shaking. The blot was then washed 10 minutes each time and 6 times with the NET gel buffer before autoradiography.

The tree was constructed using the Neighbor-Joining method (Saitou, N. and M. Nei, *Mol. Biol. Evol.*, 4:406425 (1987). The length of horizontal line reflects the divergence. The branch length between the node connecting the CLN cyclins and other cyclins was arbitrary divided.

MATERIALS AND METHODS

The following materials and methods were used in the work described in Examples 4–6.

Molecular Cloning

The human HeLa cell cDNA library, the human glioblastoma cell U118 MG cDNA library, the normal human liver genomic library, and the hybridization buffer were the same as those described above. A human hippocampus cDNA library was purchased from Stratagene, Inc. High- and low-stringency hybridizations were carried out at 68° and 50° C., respectively. To prepare template DNA for PCR reactions, approximately 2 million lambda phages from each cDNA library were plated at a density of $10^5$ PFU/150-mm plate, and DNA was prepared from the plate lysate according to Sambrook, J. et al., *Molecular Cloning: A Laboratory Manual*, 2nd ed., Cold Spring Harbor Laboratory, Cold Spring Harbor, N.Y., 1989.

Example 4

Isolation of Human Cyclin D2 and D3 cDNAs

To isolate human cyclin D2 and D3 cDNAs, two 5' oligonucleotides and one 3' degenerate oligonucleotide were derived from three highly conserved regions of human CCND1, mouse cyl1, cyl2, and cyl3 D-type cyclins (Matsushime, H. et al., *Cell* 65:701–713 (1991); Xiong, Y. et al., *Cell* 65:691–699; FIG. 8). The first 5' oligonucleotide primer, HCND11, is a 8192-fold degenerate 38-mer (TGGATG[T/C]TNGA[A/G]GTNTG[T/C]GA[A/C]GA[A/G]CA[A/G]AA[A/G]TG[T/C]GA[A/G]GA) (SEQ ID No. 37), encoding 13 amino acids (WMLEVCEEQKCEE)(SEQ ID No. 38). The second 5' oligonucleotide primer, HCND12, is a 8192-fold degenerate 29-mer (GTNTT[T/C]CCN[T/C]TNGCNATGAA[T/C]TA[T/C]TNGA) (SEQ ID No. 39), encoding 10 amino acids (VFPLAMNYLD) (SEQ ID No. 40). The 3' primer, HCND13, is a 3072-fold degenerate 24-mer ([A/G]TCNGT[A/G]TA[A/G/T]AT[A/G]CANA[A/G][T/C]TT-[T/C]TC) (SEQ ID No. 41), encoding 8 amino acids (EKLCIYTD) (SEQ ID No. 42). The PCR reactions were carried out for 30 cycles at 94° C. for 1 min, 48° C. for 1 min, and 72° C. for 1 min. The reactions contained 50 mM KCl, 10 mM Tris-HCl (pH 8.3), 1.5 mM MgCl2, 0.01% gelatin, 0.2 mM each of DATP, dGTP, dCTP, and dTTP, 2.5 units of Taq polymerase, 5 μM of oligonucleotide, and 2–10 μg of template DNA. PCR products generated by HCND11 and HCND13 were verified in a second-round PCT reaction using HCND12 and HCND13 as the primers. After resolution on a 1.2% agarose gel, DNA fragments with the expected size (200 bp between primer HCND11 and HCND13) were purified and subcloned into the SmaI site of phagmid vector pUC118 for sequencing.

To isolate full-length cyclin D3 cDNA, the 201-bp fragment of the D3 PCR product was labeled with oligonucleotide primers HCND11 and HCND13 using a random-primed labeling technique (Feinberg, A. P. et al., *Anal. Biochem.* 132:6–13 (1983)) and used to screen a human HeLa cell cDNA library. The probe used to screen the human genomic library for the CCND3 gene was a 2-kb EcoRI fragment derived from cDNA clone λD3-H34. All hybridizations for the screen of human cyclin D3 were carried out at high stringency.

The PCR clones corresponding to CCND1 and CCND3 have been repeatedly isolated from both cDNA libraries; CCND2 has not. To isolate cyclin D2, a 1-kb EcoRI fragment derived from mouse cyl2 cDNA was used as a probe to screen a human genomic library. Under low-stringency conditions, this probe hybridized to both human cyclins D1 and D2. The cyclin D1 clones were eliminated through another hybridization with a human cyclin D1 probe at high stringency. Human CCND2 genomic clones were subsequently identified by partial sequencing and by comparing the predicted protein sequence with that of human cyclins D1 and D3 as well as mouse cyl2.

As described above, human CCND1 (cyclin D1) was isolated by rescuing a triple Cln deficiency mutant of *Saccharomyces cerevisiae* using a genetic complementation screen. Evolutionary proximity between human and mouse, and the high sequence similarity among cyl1, cyl2, and cyl3, suggested the existence of two additional D-type cyclin genes in the human genome. The PCR technique was first used to isolate the putative human cyclin D2 and D3 genes. Three degenerate oligonucleotide primers were derived from highly conserved regions of human CCND1, mouse cyl1, cyl2, and cyl3. Using these primers, cyclin D1 and a 200-bp DNA fragment that appeared to be the human homolog of mouse cyl3 from both human HeLa cell and glioblastoma cell cDNA libraries was isolated. A human HeLa cell cDNA library was screened with this PCR product as probe to obtain a full-length D3 clone. Some 1.2 million cDNA clones were screened, and six positives were obtained. The longest cDNA clone from this screen, λD3-H34 (1962 bp), was completely sequenced (FIG. 4).

Because a putative human cyclin D2 cDNA was not detected by PCR, mouse cyl2 cDNA was used as a heterologous probe to screen a human cDNA library at low stringency. This resulted, initially, in isolation of 10 clones from the HeLa cell cDNA library, but all corresponded to the human cyclin D1 gene on the basis of restriction mapping. Presumably, this was because cyclin D2 in HeLa cells is expressed at very low levels. Thus, the same probe was used to screen a human genomic library, based on the assumption that the representation of D1 and D2 should be approximately equal. Of the 18 positives obtained, 10 corresponded to human cyclin D1 and 8 appeared to contain human cyclin D2 sequences (see below). A 0.4-kb BamHI restriction fragment derived from λD2-G1 1 of the 8 putative cyclin D2 clones, was then used as probe to screen a human hippocampus cDNA library at high stringency to search for 8 full-length cDNA clone of the cyclin D2 gene. Nine positives were obtained after screening of approximately 1 million cDNA clones. The longest cDNA clone, λD2-P3 (1911 bp), was completely sequenced (FIG. 3). Neither λD2-P3 nor λD3-H34 contains a poly(A) sequence, suggesting that part of the 3' untranslated region might be missing.

The DNA sequence of λD2-P3 revealed an open reading frame that could encode a 289-amino-acid protein with a 33,045-Da calculated molecular weight. A similar analysis of λD3-H34 revealed a 292-amino-acid open reading frame encoding a protein with a 32,482-Da calculated molecular weight. As in the case of human cyclin D1, there is neither methionine nor stop codons 5' to the presumptive initiating methionine codon for both λD2-P3 (nucleotide position 22, FIG. 3) and λD3-H34 (nucleotide position 101, FIG. 4). On the basis of the protein sequence comparison with human cyclin D1 and mouse cyl1 (FIG. 7) and preliminary results of the RNase protection experiment, both λD2-P3 and λD3-H34 are believed to contain full-length coding regions.

Figure 7:
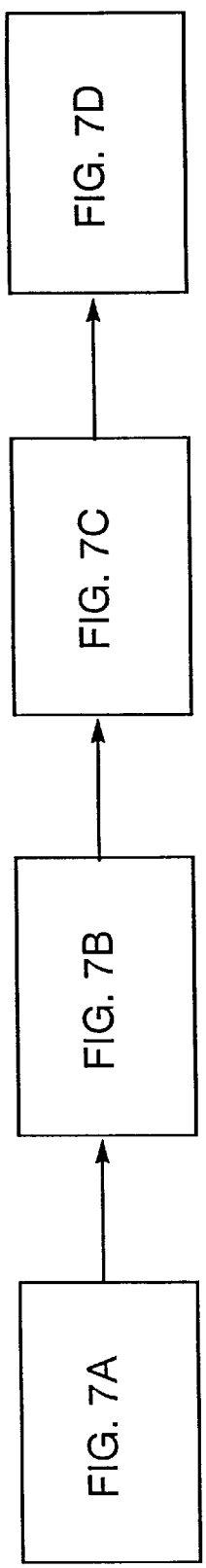
FIG. 7 shows the protein sequence comparison of eleven mammalian cyclins (CYCD1-Hs, SEQ ID No. 19; CYL1-Mm, SEQ ID No. 20; CYCD2-Hs, SEQ ID No. 21; CYCL2-Mm, SEQ ID No. 22; CYCD3-Hs, SEQ ID No. 23; CYL3-Mm, SEQ ID No. 24; CYCA-Hs, SEQ ID No. 25; CYCB1-Hs, SEQ ID No. 26; CYCB2-Hs, SEQ ID No. 27; CYCC-Hs, SEQ ID No. 28; CYCE-Hs, SEQ ID No. 29).
Figure 15A:
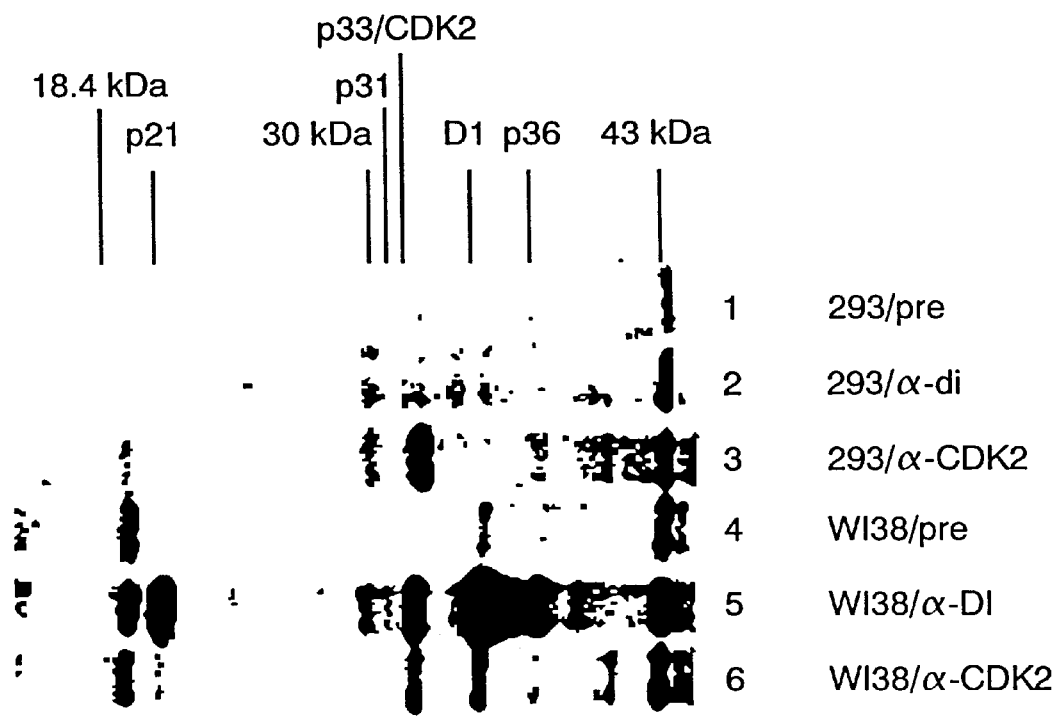
FIGS. 15A, 15B and 15C show results of analysis of [$^{35}$S] methionine-labelled immunoprecipitates.
Figure 15B:
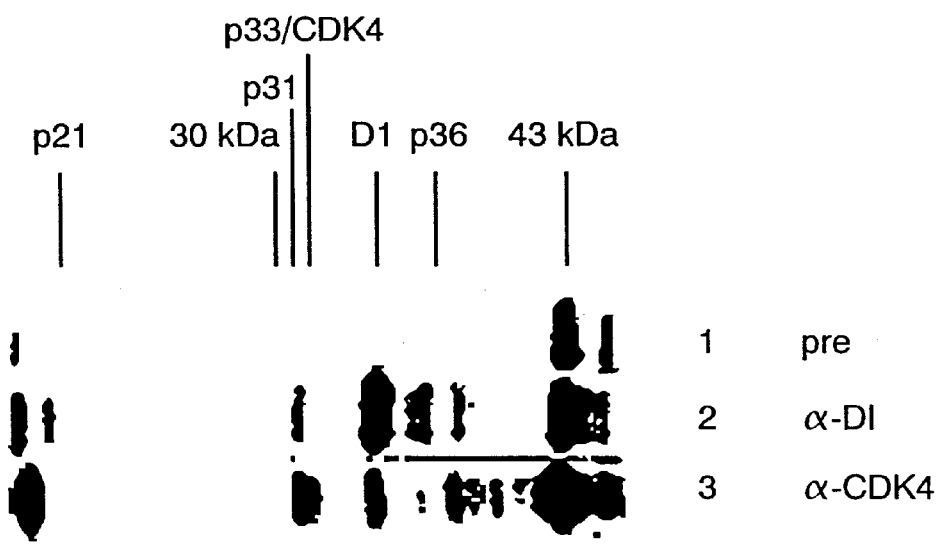
Figure 15C:
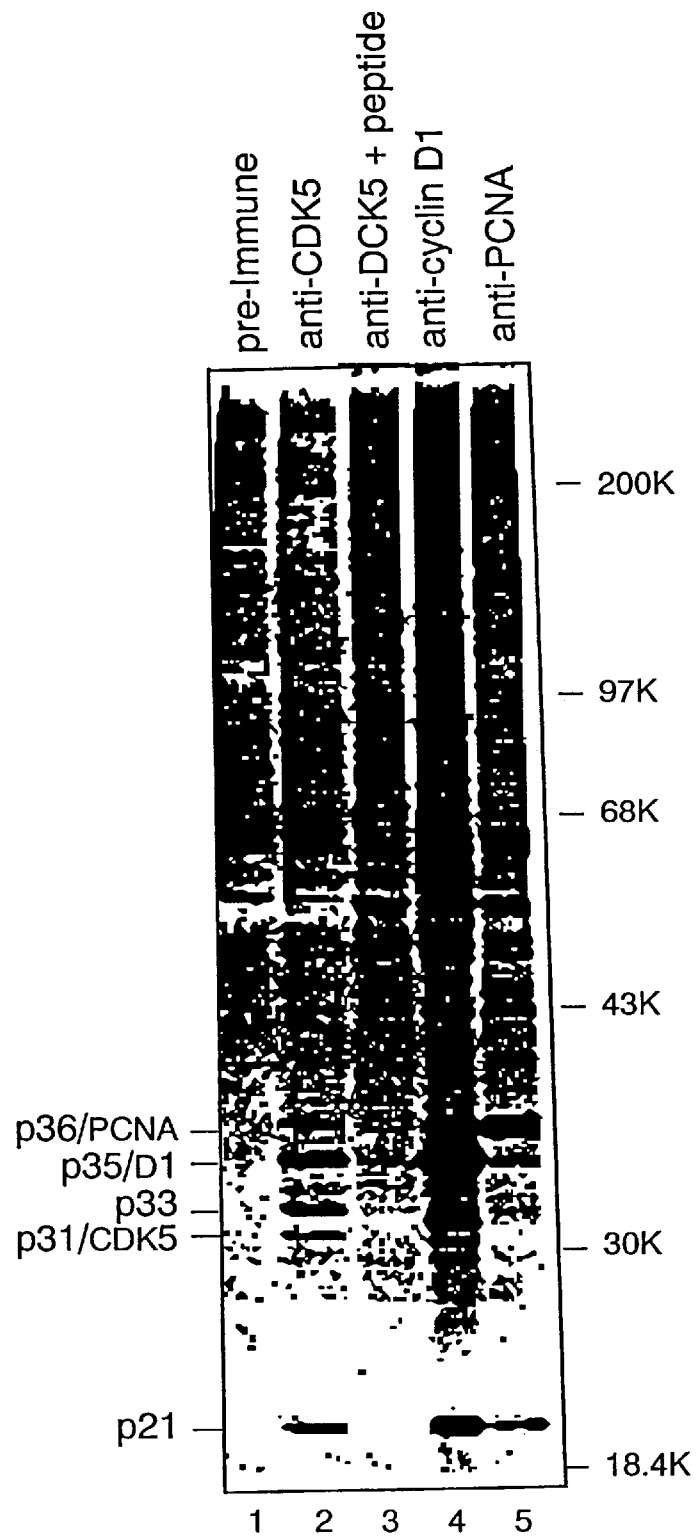

The protein sequence of all 11 mammalian cyclins identified to date were compared to assess their structural and evolutionary relationships. This includes cyclin A, cyclins B1 and B2, six D-type cyclins (three from human and three from mouse), and the recently identified cyclins E and C (FIG. 7). Several features concerning D-type cyclins can be seen from this comparison. First, as noted previously for cyclin D1, all three cyclin D genes encode a similar small size protein ranging from 289 to 295 amino acid residues, the shortest cyclins found so far. Second, they all lack the so-called "destruction box" identified in the N-terminus of both A- and B-type cyclins, which targets it for ubiquitin-dependent degradation (Glotzer, M. et al., *Nature* 349:132–138 (1991)). This suggests either that the D-type cyclins have evolved a different mechanism to govern their periodic degradation during each cell cycle or that they do not undergo such destruction. Third, the three human cyclin D genes share very high similarity over their entire coding region: 60% between D1 and D2, 60% between D2 and D3, and 52% between D1 and D3. Fourth, members of the D-type cyclins are more closely related to each other than are members of the B-type cyclins, averaging 78% for three cyclin D genes in the cyclin box versus 57% for two cyclin B genes. This suggests that the separation (emergence) of D-type cyclins occurred after that of cyclin B1 from B2. Finally, using the well-characterized mitotic B-type cyclin as an index, the most closely related genes are cyclin A (average 51%), followed by the E-type (40%), D-type (29%), and C-type cyclins (20%).

Example 5
Chromosome Localization of CCND2 and CCND3

The chromosome localization of CCND2 and CCND3 was determined by fluorescence in situ hybridization. Chromosome in situ suppression hybridization and in situ hybridization banding were performed as described previously (Lichter, T. et al., *Science* 247:64–69 (1990); Baldini, A. et al., *Genomics* 9:770–774 (1991)). Briefly λD2-G4 and λD3-G9 lambda genomic DNAs containing inserts of 15 and 16 kb, respectively, were labeled with biotin-11-dUTP (Sigma) by nick-translation (Brigatti, D. J. et al., *Urology* 126:32 (1983); Boyle, A. L., In *Current Protocols in Molecular Biology*, Wiley, New York, 1991). Probe size ranged between 200 and 400 nucleotides, and unincorporated nucleotides were separated from probes using Sephadex G-50 spin columns (Sambrook, J. et al., *Molecular Cloning: A Laboratory Manual* 2nd ed. Cold Spring Harbor Laboratory, Cold Spring Harbor, N.Y., 1989). Metaphase chromosome spreads prepared by the standard technique (Lichter, T. et al., *Science* 247:64–69 (1990)) were hybridized in situ with biotin-labeled D2-G4 or D3-G9. Denaturation and preannealing of 5 μg of DNase-treated human placental DNA, 7 μg of DNased salmon sperm DNA, and 100 ng of labeled probe were performed before the cocktail was applied to Alu prehybridized slides. The in situ hybridization banding pattern used for chromosome identification and visual localization of the probe was generated by cohybridizing the spreads with 40 ng of an Alu 48-mer oligonucleotide. This Alu oligo was chemically labeled with digoxigenin-11-dUTP (Boehringer-Mannheim) and denatured before being applied to denatured chromosomes. Following 16–18 h of incubation at 37° C. and posthybridization wash, slides were incubated with blocking solution and detection reagent (Lichter, T. et al., *Science* 247:64–69 (1990)). Biotin-labeled DNA was detected using fluorescence isothiocyanate (FITC)-conjugated avidin DCS (5 μg/ml) (Vector Laboratories); digoxigenin-labeled DNA was detected using a rhodamine-conjugated anti-digoxigenin antibody (Boehringer-Mannheim). Fluorescence signals were imaged separately using a Zeiss Axioskop-20 epifluorescence microscope equipped with a cooled CCD camera (Photometrics CH220). Camera control and image acquisition were performed using an Apple Macintosh IIX computer. The gray scale images were pseudocolored and merged electronically as described previously (Baldini, A. et al., *Genomics* 9:770–774 (1991)). Image processing was done on a Macintosh IIci computer using Gene Join Maxpix (software by Tim Rand in the laboratory of D. Ward, Yale) to merge FITC and rhodamine images. Photographs were taken directly from the computer monitor.

Chromosomal fluorescence in situ hybridization was used to localize D2-G4 and D3-G9. The cytogenetic location of D2-G4 on chromosome 12p band 13 and that of D3-G9 on chromosome 6p band 21 were determined by direct visualization of the two-color fluorescence in situ hybridization using the biotin-labeled probe and the digoxigen-labeled Alu 48-mer oligonucleotide (FIG. 5).

The Alu 48-mer R-bands, consistent with the convenional R-banding pattern, were imaged and merged with images generated from the D2-G4 and D3-G9 hybridized probes. The loci of D2-G4 and D3-G9 were visualized against the Alu banding by merging the corresponding FITC and rhodamine images. This merged image allows the direct visualization of D2-G4 and D3-G9 on chromosomes 12 and 6, respectively. The D2-G4 probe lies on the positive R-band 12p13, while D3-G9 lies on the positive R-band 6p21. Cross-hybridization was not detected with either pseudogene cyclin D2 or D3, presumably because the potentially cross-hybridizing sequence represents only a sufficiently small proportion of the 15- and 16-kb genomic fragments (nonsuppressed) used as probe, and the nucleotide sequences of pseudogenes have diverged from their ancestral active genes.

Example 6
Isolation and Characterization of Genomic Clones of Human D-Type Cyclins Genomic clones of human D-type cyclins were isolated and characterized to study the genomic structure and to obtain probes for chromosomal mapping. The entire 1.3-kb cyclin D1 cDNA clone was used as probe to screen a normal human liver genomic library. Five million lambda clones were screened, and three positives were obtained. After initial restriction mapping and hybridizations, lambda clone G6 was chosen for further analysis. A 1.7-kb BamHI restriction fragment of λD1-G6 was subcloned into pUC118 and completely sequenced. Comparison with the cDNA clones previously isolated and RNase protection experiment results (Withers, D. A. et al., *Mol. Cell. Biol.* 11:4846–4853 (1991)) indicated that this fragment corresponds to the 5' part of the cyclin D1 gene. As shown in FIG. 8A, it contains 1150 bp of upstream promoter sequence and a 198-bp exon followed by an intron.

Eighteen lambda genomic clones were isolated from a similar screening using mouse cyl2 cDNA as a probe under low-stringency hybridization conditions, as described above (Example 4). Because it was noted in previous cDNA library screening that the mouse cyl2 cDNA probe can cross-hybridize with the human D1 gene at low stringency, a dot-blot hybridization at high stringency was carried out, using the human D1 cDNA probe. Ten of the 18 clones hybridized with the human D1 probe and 8 did not. On the basis of the restriction digestion analysis, the 8 lambda clones that did not hybridize with the human D1 probe at high stringency fall into three classes represented by λD2-G1, λD2-G2, and λD2-G4, respectively. These three lambda clones were subcloned into a pUC plasmid vector, and small restriction fragments containing coding region were identified by Southern hybridization using a mouse cyl2 cDNA probe. A 0.4-kb BamHI fragment derived from λD2-G1 was subsequently used as a probe to screen a human hippocampus cell cDNA library at high stringency. Detailed restriction mapping and partial sequencing indicated that λD2-G1 and λD2-G2 were two different clones corresponding to the same gene, whereas λD2-G4 appeared to correspond to a different gene. A 2.7-kb SacI-SmaI fragment from λD2-G4 and 1.5-kb BclI-BglII fragment from λD2-G1 have been completely sequenced. Nucleotide sequence comparison revealed that the clone λD2-G4 corresponds to the D2 cDNA clone λD2-P3 (FIG. 3). As shown in FIG. 8A, the 2.7-kb SacI-SmaI fragment contains 1620 bp of sequence 5' to the presumptive initiating methionine codon identified in D2 cDNA (FIG. 3) and a 195-bp exon followed by a 907-bp intervening sequence.

Lambda genomic clones corresponding to the human cyclin D3 were isolated from the same genomic library using human D3 cDNA as a probe. Of four million clones screened, nine were positives. Two classes of clones, represented by λD3-G4 and λD3-G9, were distinguished by restriction digestion analysis. A 2.0-kb HindIII-ScaI restriction fragment from λD3-G5 and a 3.7-kb SacI-HindIII restriction fragment from λD3-G9 were further subcloned into a pUC plasmid vector for more detailed restriction mapping and complete sequencing, as they both hybridized to the 5' cyclin D3 cDNA probe. As presented in FIG. 9C, the 3.7-kb fragment from clone G9 contains 1.8 kb of sequence 5' to the presumptive initiating methionine codon identified in D3 cDNA (FIG. 4), a 198-bp exon 1, a 684-bp exon 2, and a 870-bp intron.

Comparison of the genomic clones of cyclins D1, D2, and D3 revealed that the coding regions of all three human CCND genes are interrupted at the same position by an intron (indicated by an arrow in FIG. 8). This indicated that the intron occurred before the separation of cyclin D genes.

Example 7
Isolation and Characterization of Two Cyclin D Pseudogenes

The 1.5-kb BclI-BglII fragment subcloned from clone λD2-G1 has been completely sequenced and compared with cyclin D2 cDNA clone λD2-P3. As shown in FIG. 10, it contains three internal stop codons (nucleotide positions 495, 956, and 1310, indicated by asterisks), two frameshifts (position 1188 and 1291, slash lines), one insertion, and one deletion. It has also accumulated many missense nucleotide substitutions, some of which occurred at the positions that are conserved in all cyclins. For example, triplet CGT at position 277 to 279 of D2 cDNA (FIG. 3) encodes amino acid Arg, which is an invariant residue in all cyclins (see FIG. 8). A nucleotide change from C to T at the corresponding position (nucleotide 731) in clone D2-G1 (FIG. 10) gave rise to a triplet TGT encoding Cys instead of Arg. Sequencing of the 2.0-kb HindIII-ScaI fragment from clone λD3-G5 revealed a cyclin D3 pseudogene (FIG. 11). In addition to a nonsense mutation (nucleotide position 1265), two frameshifts (position 1210 and 1679), a 15-bp internal duplication (underlined region from position 1361 to 1376), and many missense mutations, a nucleotide change from A to G at position 1182 resulted in an amino acid change from the presumptive initiating methionine codon ATG to GTG encoding Val. On the basis of these analyses, we conclude that clones λD2-G1 and λD3-G5 contain pseudogenes of cyclins D2 and D3, respectively.

Example 8
Identification of a Cyclin Dependent Kinase and Demonstration that D-Type Cyclins Associated with Multiple Protein Kinases and the DNA Replication and Repair Factor PCNA
Experimental Procedures
Cells Human diploid lung fibroblast WI38 cells were obtained from American Type Culture Collection at passage 13 and were grown in Dulbecco-Modified Eagle media supplemented with 10% fetal bovine serum and used between passages 16–22. 293 cells were cultured similarly.
Antibodies To raise anti-cyclin D1 antibody, a 609 bp DNA restriction fragment encoding 202 amino acid residues (~25 kDa) of human cyclin D1 amino-terminal region (the NCoI fragment from nucleotides 143 to 751 in FIG. 2 of Xiong, et al., 1991) was subcloned into a phage T7 expression vector, pET-3d (Studier, et al., 1990) and introduced into *E. coli* strain BL21 (DE3). Bacterial extracts were prepared in lysis buffer (150 mM NaCl, 50 mM Tris-HCl, pH7.5 and 10% glycerol) by disrupting cells with sonication and clarifying the supernatant by centrifugation at 20,000 g for 10 minutes. Pellets containing insoluble cyclin D protein was resuspended in lysis buffer supplemented with 8 M urea, after 30 minutes shaking at room temperature, the suspension was centrifuged again at 20,000 g for 10 minutes. Pellets containing insoluble cyclin D protein was resuspended in SDS sample buffer and separated on 10% SDS-polyacrylamide gel. The 25 kDa cyclin D protein was visualized and excised after staining the gel with 0.25M KCl in the cold room. Gel slices were further crushed by repeated passage through an 18 gauge needle and cyclin D protein was extracted by incubating the crushed gel particles with PBS containing 0.1% SDS at 42° C. for several hours and used for injection of rabbits. To affinity purify the anti-cyclin D1 immunoglobulins, bacterially produced p25 proteins were cross-linked to the Reacti-Gel (6x) according to the manufacturer's instruction. The affinity column was washed with excess volume of PBS containing 0.05% Tween-20 before and after crude serum was applied to the column. Bound immunoglobulins were eluted with Glycine-NaCl (pH2.5) into 1.5 M Tris-HCl, pH8.5 to instantly neutralize the antibodies. To reduce the high background caused by immunoglobulin proteins, affinity purified anti-cyclin D1 was crosslinked to protein A agarose beads according to Harlow and Lane (1988). On Western blots, the anti-cyclin D1 antiserum weakly cross-reacts with bacterially produced human cyclin D2, very poorly with bacterially produced human cyclin D3, and detects a single band from total WI38 cell lysates. In the immunoprecipitations with RIPA buffer (0.1% SDS), more than 90% of cyclin D1-associated p36, p33, p31 and p21 disappeared while the amount of cyclin D1 remained the same as that in the immunoprecipitations with NP40 (0.5%) buffers.

For anti-CDK5 antibody production a peptide C YFSDFCPP (SEQ ID No. 39) with the underlined amino acid residues corresponding to the carboxy-terminal region of CDK5 was synthesized. The peptide was coupled to keyhole limpet hemocyanin (Pierce) which was then used to immunize rabbits as described (Green, et al., 1982).

Anti-cyclin D3 peptide antibody was similarly raised against a synthetic peptide C<u>DELDOASTPTDVRDIDL</u> (SEQ ID No. 40) with the underlined region corresponding to the carboxy-terminal region of human cyclin D3. The rabbit was later stimulated with bacterial produced full length human cyclin D3. Cyclin D3 specific immunoglobulins were purified on an affinity column in which the 17-mer cyclin D3 peptides were crosslinked to the Reacti-Gel (6×). The affinity purified anti-cyclin D3 peptide antibody does not cross-react with bacterially produced cyclin D1 or D2 on Western blots and does not immunoprecipitate cyclin D1 from W138 cell lysates.

The antiserum against S. pombe $p34^{cdc2}$ (G8) was described before (Draetta, et al., 1987). Human autoimmune anti-PCNA antiserum was from Dr. Michael Mathews (Cold Spring Harbor Laboratory, New York). Affinity purified anti-PCNA monoclonal antibody used in Western-blots was purchased from Boehringer Mannheim. Affinity purified anti-PCNA monoclonal antibody used in immunoprecipitation of FIG. 6B was purchased from oncogene Science. Anti-CDK2 peptide antiserum was a gift of Dr. Giulio Draetta (EMBL, Heidelberg, Pagno, et al., 1992b) and does not cross-react with CDC2, CDK4 and CDK5 polypeptides. Anti-CDK4 antiserum was a gift of Dr. Steven Hanks (Vanderbilt University, Tennessee) and was raised against a fasion protein of glutathione S transferase (GST) and a C-terminal portion of CDK4. It does not cross-react with CDK2 and CDK5.

Screening Human cDNA Expression Library

A human HeLa cell cDNA expression library constructed in lambda ZAP II (#936201) was from Stratagene. Human $p34^{cdc2}$ was highly insoluble when produced from bacteria. The conventional antibody screening method (Young and Davis, 1983) is suitable only when there is sufficient amount of soluble recombinant proteins in phage plaques. The screening method, therefore, was modified to include a step which involved the use of 6M guanidine to solubilize recombinant proteins after they have been transferred to nitrocellulose paper, a procedure which was initially developed to produce refolded recombinant proteins with certain activities (Vinson, et al., 1988). Two million phage plaques from the λZAP II HeLa cDNA library were screened with antiserum against S. pombe $p34^{cdc2}$ (G8). After overlaying phage plaques with IPTG-impregnated nitrocellulose filters for 4 hours at 42° C., the filters were removed from culture dishes and were then treated with 6 M guanidine-HCl in a buffer containing 25 mM Hepes, pH7.0, 50 mM NaCl, 2 mM DTT for 10 min at 25° C. The filters were washed free of guanidine with Tris-buffered saline before antibody incubation. This procedure enhanced our antibody detection signal greatly which probably was due to the solubilization of bacterial-produced polypeptide precipitates by guanidine. The G8-positive cDNA clones subcloned into pBluescript SK vector (Stratagene) and sequenced from both directions using ABI automated DNA sequencer (Model 373A). For sequence homology search, the FASTA program was used (Pearson and Lipman, 1988).

Immunoprecipitation and Western-Blotting

For metabolic labelling with [$^{35}$S] methionine, subconfluent (40–60%) cells were washed twice with prewarmed labelling media (methionine-, cystine-free DMEM [ICN] supplemented with 10% dialyzed fetal bovine serum, [GIBCO]). After 30 minutes incubation with the labelling media, [$^{35}$S] methionine (Trans$^{35}$S-label, ICN) was added to media (approximately 200 µCi/ml) and continued to incubate for four to six hours before lysis. All steps of immunoprecipitations were carried out in the cold room. Cells from 40 to 60% confluent 150 mM dish were washed twice with cold PBS and scraped into NP-40 lysis buffer (50 mM Tris-HCl, pH7.4, 150 mM NaCl, 20 mM EDTA, 0.5% NP-40, 1 mM PMSF, 25 µg/ml leupeptin, 25 µ/ml aprotitin, 1 mM benzamidine and 10 µg/ml trypsin inhibitor) and lysed by rotating for 15 to 30 minutes. Nuclei were removed by centrifugation at 15,000 g for 5 minutes and lysates were pre-cleared by incubating with either pre-immune serum or normal rabbit serum and IgG sorb (The Enzyme Center, Inc.) for 20 to 30 minutes followed by a 10 minute centrifugation at 15,000 g. Antibody pre-coupled to the protein A agarose beads (Pierce) was added to the clarified lysates and incubated for six to eight hours. Immunoprecipitates were washed three to four times with lysis buffer at room temperature, resuspended in SDS sample buffer and separated on SDS-polyacrylamide gels.

For the $^{35}$S methionine-labelled precipitates, polyacrylamide gels (except those for V8 proteolytic mapping experiments) were fixed with 10% glacial acetic acid and 30% methanol for 30 minutes to one hour, enhanced by impregnating with autoradiography enhances (Du Pont) for 30 minutes and precipitated in water for 15 to 30 minutes. Enhanced gels were dried and exposed to X-ray films at −70° C. For Western-blotting, polypeptides were transferred to a nitrocellulose filer using a SDE Electroblotting System (Millipore) for 45 minutes at constant current of 400 mA. The filter was blocked for 1 to 3 hours with TBST (20 mM Tris-HCl, pH 7.5, 137 mM NaCl, 0.1% Tween-20) containing 5% dry milk, incubated with primary antibody for 4 hours to overnight in TBST containing 5% dry milk and washed 4 times, 10 minutes each time, with TBST. Appropriate secondary antibody (1:10,000 dilution of either horseradish peroxidase linked sheet anti-mouse Ig or donkey anti-rabbit Ig, Amersham) were incubated with filters for one hour and specific proteins were detected using an enhanced chemiluminescence system (ECL, Amersham).

Partial Proteolytic Peptide Mapping

Human cyclin D1, cyclin D2, cyclin D3, CDC2, CDK2, CDK3, CDK4, CDK5 and PCNA were subcloned into pBluescript vector (Stratagene) for in vitro translation with T7 RNA polymerase using a TNT coupled reticulocyte lysate system (Promega). Immunoprecipitation of [$^{35}$S] methionine-labelled lysates and SDS-polyacrylamide gel electrophoresis were the same as described above. Polyacrylamide gels were dried without prior fixation and enhanced treatment, exposed to Fuji image plates and visualized on Fuji bio-imaging analyzer BAS2000. Appropriate protein bands were excised from the gels using image printout as template, in-gel partially digested with various amount of S. aureus V8 protease according to (Cleveland, et al., 1977) and (Harlow and Lane, 1988), separated on a 17.5% SDS-PAGE. Gels were dried and exposed to a X-ray film for 2 weeks, or analyzed on a Fuji image analyzer BAS2000.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. An isolated or recombinant D-type cyclin encoded by a nucleic acid which hybrizes under conditions of 2×SSC at 68° C. to the nucleic acid of SEQ ID NO: 3, which D-type cyclin replaces a CLN-type protein essential for cell start in budding yeast.

2. D-type cyclin of claim 1 which is of mammalian origin.

3. D-type cyclin of claim 2 which is of human origin.

4. An isolated or recombinant D-type cyclin of approximate molecular weight of 34 kD and comprising an amino acid sequence represented by SEQ ID NO. 4.

5. An isolated or recombinant D-type cyclin comprising an amino acid sequence represented by SEQ ID NO. 4, which D-type cyclin binds to a cyclin dependent kinase (CDK) and regulates a kinase activity of said CDK.

6. An isolated or recombinant D-type cyclin polypeptide encoded by a nucleic acid that hybridizes under conditions of 2×SSC at 68° C. to the nucleic acid of SEQ ID NO: 3, which D-type cyclin binds a mammalian cyclin dependent kinase (CDK).

7. D-type cyclin of claim 5 or 6, wherein the CDK is CDK4.

8. D-type cyclin of claim 1, 5 or 6, which polypeptide is a fusion protein.

9. D-type cyclin of claim 8, wherein the fusion protein further includes a glutathione-S-transferase amino acid sequence.

10. D-type cyclin of claim 6, which is of mammalian origin.

11. D-type cyclin of claim 10, which is of human origin.

12. D-type cyclin of claim 1, 4, 5 or 6, which polypeptide is a product of recombinant expression in a eukaryotic cell.

13. D-type cyclin of claim 12, which polypeptide is a product of recombinant expression in a mammalian cell.

14. D-type cyclin of claim 12, which polypeptide is a product of recombinant expression in a yeast cell.

15. An isolated or recombinant D-type cyclin encoded by a nucleic acid which hybrizes under conditions of 2×SSC at 68° C. to the nucleic acid of SEQ ID NO: 5, which D-type cyclin replaces a CLN-type protein essential for cell start in budding yeast.

16. D-type cyclin of claim 15 which is of mammalian orgin.

17. D-type cyclin of claim 15 which is of human origin.

18. An isolated or recombinant D-type cyclin of approximate weight of 34 kD and comprising an amino acid sequence represented by SEQ ID NO. 6.

19. An isolated or recombinant D-type cyclin comprising an amino acid sequence represented by SEQ ID NO. 6, which D-type cyclin binds to a cyclin dependent kinase (CDK) and regulates a kinase activity of said CDK.

20. An isolated or recombinant D-type cyclin polypeptide encoded by a nucleic acid that hybridizes under conditions of 2×SSC at 68° C. to the nucleic acid of SEQ ID NO: 5, which D-type cyclin binds to a mammalian cyclin dependent kinase (CDK).

21. D-type cyclin of claim 19 or 20, wherein the CDK is CDK4.

22. D-type cyclin of claim 15, 19 or 20, which polypeptide is a fusion protein.

23. D-type cyclin of claim 22, wherein the fusion protein further includes a glutathione-S-transferase amino acid sequence.

24. D-type cyclin of claim 20, which is of mammalian origin.

25. D-type cyclin of claim 24, which is of human origin.

26. D-type cyclin of claim 15, 18, 19 or 20, which polypeptide is a product of recombinant expression in a eukaryotic cell.

27. D-type cyclin of claim 26, which polypeptide is a product of recombinant expression in a mammalian cell.

28. D-type cyclin of claim 26, which is a product of recombinant expression in a yeast cell.

29. An isolated or recombinant D-type cyclin comprising an amino acid sequence that diverges no more than 40% from the amino acid sequence represented by SEQ ID No. 4, which D-type cyclin replaces a CLN-type protein essential for cell start in budding yeast.

30. An isolated or recombinant D-type cyclin comprising an amino acid sequence that diverges no more than 40% from the amino acid sequence represented by SEQ ID No.

6, which D-type cyclin replaces a CLN-type protein essential for cell start in budding yeast.

31. A D-type cyclin of claim 29, which protein comprises a cyclin box that diverges no more than 22% from the cyclin box represented in the amino acid sequence of SEQ ID No. 4.

32. A D-type cyclin of claim 30, which protein comprises a cyclin box that diverges no more than 22% from the cyclin box represented in the amino acid sequence of SEQ ID No 6.

33. D-type cyclin of claim 1, 4, 5, 6, 8, 15, 18, 19, 20, 29 or 30, which protein is purified.

34. A purified protein complex comprising a cyclin dependent kinase (CDK) and the D-type cyclin of any of claims 1, 4, 5, 6, 8, 15, 18, 19 or 20.

35. The purified protein complex of claim 34, wherein the CDK is CDK4.

36. A purified protein complex comprising a cyclin dependent kinase (CDK) and the D-type cyclin of any of claims 4, 5, 18, or 19.

* * * * *

UNITED STATES PATENT AND TRADEMARK OFFICE
CERTIFICATE OF CORRECTION

PATENT NO. : 5,998,582
DATED : December 7, 1999
INVENTOR(S) : David H. Beach

It is certified that error appears in the above-identified patent and that said Letters Patent is hereby corrected as shown below:

Column 103,
Line 11, delete "8," from the list of claims in claim 33.

Column 104,
Line 3, delete "8," from the list of claims in claim 34.

Signed and Sealed this

Fourth Day of September, 2001

Attest:

NICHOLAS P. GODICI
*Acting Director of the United States Patent and Trademark Office*

*Attesting Officer*

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
        (A) LENGTH: 1325 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 145..1029

(xi) SEQUENCE DESCRIPTION: SEQ ID NO:1:

```
GCAGTAGCAG CGAGCAGCAG AGTCCGCACG CTCCGGCGAG CGCCAGAACA GCGCGAGGGA      60

GCGCGGGGCA GCAGAAGCGA GAGCCGAGCG CGGACCCAGC CAGGACCCAC AGCCCTCCCC     120

AGCTGCCCAG GAAGAGCCCC AGCC ATG GAA CAC CAG CTC CTG TGC TGC GAA       171
                           Met Glu His Gln Leu Leu Cys Cys Glu
                             1               5

GTG GAA ACC ATC CGC CGC GCG TAC CCC GAT GCC AAC CTC CTC AAC GAC      219
Val Glu Thr Ile Arg Arg Ala Tyr Pro Asp Ala Asn Leu Leu Asn Asp
 10              15                  20                  25

CGG GTG CTG CGG GCC ATG CTG AAG GCG GAG GAG ACC TGC GCG CCC TCG      267
Arg Val Leu Arg Ala Met Leu Lys Ala Glu Glu Thr Cys Ala Pro Ser
             30                  35                  40

GTG TCC TAC TTC AAA TGT GTG CAG AAC GAC GTC CTC CCG TCC ATG CCG      315
Val Ser Tyr Phe Lys Cys Val Gln Asn Asp Val Leu Pro Ser Met Pro
         45                  50                  55

AAG ATC GTC GCC ACC TGG ATG CTG GAG GTC TGC GAG GAA CAG AAG TGC      363
Lys Ile Val Ala Thr Trp Met Leu Glu Val Cys Glu Glu Gln Lys Cys
     60                  65                  70

GAG GAG GAG CTC TTC CCG CTG GCC ATG AAC TAC CTG GAC CGG TTC CTG      411
Glu Glu Glu Leu Phe Pro Leu Ala Met Asn Tyr Leu Asp Arg Phe Leu
 75                  80                  85

TCG CTG GAG CCC GTG AAA AAG AGC CGC CTG CAG CTG CTG GGG GCC ACT      459
Ser Leu Glu Pro Val Lys Lys Ser Arg Leu Gln Leu Leu Gly Ala Thr
 90                  95                 100                 105

TGC ATG TTC GTG GCC TCT AAG ATG AAG GAG ACC ATC CCC CTG ACG GCC      507
Cys Met Phe Val Ala Ser Lys Met Lys Glu Thr Ile Pro Leu Thr Ala
             110                 115                 120

GAG AAG CTG TGC ATC TAC ACC GAC GCC TCC ATC CCC CCC GAG GAC CTG      555
Glu Lys Leu Cys Ile Tyr Thr Asp Ala Ser Ile Pro Pro Glu Asp Leu
         125                 130                 135

CTG CAA ATG GAG CTG CTC CTG GTG AAC AAG CTC AAG TGG AAC CTG GCC      603
Leu Gln Met Glu Leu Leu Leu Val Asn Lys Leu Lys Trp Asn Leu Ala
     140                 145                 150

GCA ATG ACC CCG CAC GAT TTC ATT GAA CAC TTC CTC TCC AAA ATG ACA      651
Ala Met Thr Pro His Asp Phe Ile Glu His Phe Leu Ser Lys Met Thr
 155                 160                 165

GAG GCG GAG GAG AAC AAA CAG ATC ATC CGC AAA CAC GCG CAG ACC TTC      699
Glu Ala Glu Glu Asn Lys Gln Ile Ile Arg Lys His Ala Gln Thr Phe
 170                 175                 180                 185

GTT GCC TCT TGT GCC ACA GAT CTG AAG TTC ATT TCC AAT CCG CCC TCC      747
Val Ala Ser Cys Ala Thr Asp Leu Lys Phe Ile Ser Asn Pro Pro Ser
             190                 195                 200
```

```
ATG GTG GCA GCG GGG ACC GTG GTC GCC GCA GTG CAA GGC CTG AAC CTG        795
Met Val Ala Ala Gly Thr Val Val Ala Ala Val Gln Gly Leu Asn Leu
        205                 210                 215

AGG AGC CCC AAC AAC TTC CTG TCG TAC TAC CGC CTC ACA CGC TTC CTC        843
Arg Ser Pro Asn Asn Phe Leu Ser Tyr Tyr Arg Leu Thr Arg Phe Leu
        220                 225                 230

TCC AGA GTG ATC AAG TGT GAC CCA GAC TGC CTC CGG GCC TCC CAG GAG        891
Ser Arg Val Ile Lys Cys Asp Pro Asp Cys Leu Arg Ala Ser Gln Glu
        235                 240                 245

CAG ATC GAA GCC CTG CTG GAG TCA AGC CTG CGC CAG GCC CAC CAG AAC        939
Gln Ile Glu Ala Leu Leu Glu Ser Ser Leu Arg Gln Ala His Gln Asn
250                 255                 260                 265

ATG GAC CCC AAG GCC GCC GAG GAG GAG GAA GAG GAG GAG GAG GAG GTG        987
Met Asp Pro Lys Ala Ala Glu Glu Glu Glu Glu Glu Glu Glu Glu Val
            270                 275                 280

GAC CTG GCT TGC ACA CCC ACC GAC GTC CCG GAC CTG GAC ATC               1029
Asp Leu Ala Cys Thr Pro Thr Asp Val Pro Asp Leu Asp Ile
                285                 290                 295

TGAGGGGCCC AGCGAGGCGG GCGCCACCGC CACCCGCAGC GAGGGCGGAG CCGGCCCCAG     1089

GTGCTCCACA TGACAGTCCC TCCTCTCCGG AGCATTTTGA TACCAGAAGG GAAACCTTCA     1149

TTCTCCTTGT TGTTGGTTGT TTTTTCCTTT GCTCTTTCCC CCTTCCATCT CTCACTTAAC    1209

CAAAACAAAA AGATTACCCA AAAACTGTCT TTAAAAGAGA GAGAGAGAAA AAAAAAAAAA     1269

AAAAAAAAAA AAAAAAAAAA AAAAAAAAAA AAAAAAAAAA AAAAAAAAAA AAAAA         1325

(2) INFORMATION FOR SEQ ID NO:2:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:2:

Met Glu His Gln Leu Leu Cys Cys Glu Val Glu Thr Ile Arg Arg Ala
 1               5                  10                  15

Tyr Pro Asp Ala Asn Leu Leu Asn Asp Arg Val Leu Arg Ala Met Leu
                20                  25                  30

Lys Ala Glu Glu Thr Cys Ala Pro Ser Val Ser Tyr Phe Lys Cys Val
            35                  40                  45

Gln Asn Asp Val Leu Pro Ser Met Pro Lys Ile Val Ala Thr Trp Met
        50                  55                  60

Leu Glu Val Cys Glu Glu Gln Lys Cys Glu Glu Glu Leu Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Ala Ser Ile Pro Pro Glu Asp Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Thr Glu Ala Glu Glu Asn Lys Gln
                165                 170                 175

Ile Ile Arg Lys His Ala Gln Thr Phe Val Ala Ser Cys Ala Thr Asp
```

```
                  180                 185                 190
Leu Lys Phe Ile Ser Asn Pro Pro Ser Met Val Ala Ala Gly Thr Val
        195                 200                 205

Val Ala Ala Val Gln Gly Leu Asn Leu Arg Ser Pro Asn Asn Phe Leu
        210                 215                 220

Ser Tyr Tyr Arg Leu Thr Arg Phe Leu Ser Arg Val Ile Lys Cys Asp
225                 230                 235                 240

Pro Asp Cys Leu Arg Ala Ser Gln Glu Gln Ile Glu Ala Leu Leu Glu
                245                 250                 255

Ser Ser Leu Arg Gln Ala His Gln Asn Met Asp Pro Lys Ala Ala Glu
                260                 265                 270

Glu Glu Glu Glu Glu Glu Glu Glu Val Asp Leu Ala Cys Thr Pro Thr
        275                 280                 285

Asp Val Pro Asp Leu Asp Ile
290                 295
```

(2) INFORMATION FOR SEQ ID NO:3:

(i) SEQUENCE CHARACTERISTICS:
        (A) LENGTH: 1911 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 22..888

(xi) SEQUENCE DESCRIPTION: SEQ ID NO:3:

```
GAATTCCCGC CGGGCTTGGC C ATG GAG CTG CTG TGC CAC GAG GTG GAC CCG         51
                         Met Glu Leu Leu Cys His Glu Val Asp Pro
                          1               5                  10

GTC CGC AGG GCC GTG CGG GAC CGC AAC CTG CTC CGA GAC GAC CGC GTC         99
Val Arg Arg Ala Val Arg Asp Arg Asn Leu Leu Arg Asp Asp Arg Val
            15                  20                  25

CTG CAG AAC CTG CTC ACC ATC GAG GAG CGC TAC CTT CCG CAG TGC TCC        147
Leu Gln Asn Leu Leu Thr Ile Glu Glu Arg Tyr Leu Pro Gln Cys Ser
        30                  35                  40

TAC TTC AAG TGC GTG CAG AAG GAC ATC CAA CCC TAC ATG CGC AGA ATG        195
Tyr Phe Lys Cys Val Gln Lys Asp Ile Gln Pro Tyr Met Arg Arg Met
    45                  50                  55

GTG GCC ACC TGG ATG CTG GAG GTC TGT GAG GAA CAG AAG TGC GAA GAA        243
Val Ala Thr Trp Met Leu Glu Val Cys Glu Glu Gln Lys Cys Glu Glu
60                  65                  70

GAG GTC TTC CCT CTG GCC ATG AAT TAC CTG GAC CGT TTC TTG GCT GGG        291
Glu Val Phe Pro Leu Ala Met Asn Tyr Leu Asp Arg Phe Leu Ala Gly
75                  80                  85                  90

GTC CCG ACT CCG AAG TCC CAT CTG CAA CTC CTG GGT GCT GTC TGC ATG        339
Val Pro Thr Pro Lys Ser His Leu Gln Leu Leu Gly Ala Val Cys Met
            95                 100                 105

TTC CTG GCC TCC AAA CTC AAA GAG ACC AGC CCG CTG ACC GCG GAG AAG        387
Phe Leu Ala Ser Lys Leu Lys Glu Thr Ser Pro Leu Thr Ala Glu Lys
        110                 115                 120

CTG TGC ATT TAC ACC GAC AAC TCC ATC AAG CCT CAG GAG CTG CTG GAG        435
Leu Cys Ile Tyr Thr Asp Asn Ser Ile Lys Pro Gln Glu Leu Leu Glu
    125                 130                 135

TGG GAA CTG GTG GTG CTG GGG AAG TTG AAG TGG AAC CTG GCA GCT GTC        483
Trp Glu Leu Val Val Leu Gly Lys Leu Lys Trp Asn Leu Ala Ala Val
140                 145                 150
```

```
ACT CCT CAT GAC TTC ATT GAG CAC ATC TTG CGC AAG CTG CCC CAG CAG       531
Thr Pro His Asp Phe Ile Glu His Ile Leu Arg Lys Leu Pro Gln Gln
155             160             165             170

CGG GAG AAG CTG TCT CTG ATC CGC AAG CAT GCT CAG ACC TTC ATT GCT       579
Arg Glu Lys Leu Ser Leu Ile Arg Lys His Ala Gln Thr Phe Ile Ala
            175             180             185

CTG TGT GCC ACC GAC TTT AAG TTT GCC ATG TAC CCA CCG TCG ATG ATC       627
Leu Cys Ala Thr Asp Phe Lys Phe Ala Met Tyr Pro Pro Ser Met Ile
            190             195             200

GCA ACT GGA AGT GTG GGA GCA GCC ATC TGT GGG CTC CAG CAG GAT GAG       675
Ala Thr Gly Ser Val Gly Ala Ala Ile Cys Gly Leu Gln Gln Asp Glu
            205             210             215

GAA GTG AGC TCG CTC ACT TGT GAT GCC CTG ACT GAG CTG CTG GCT AAG       723
Glu Val Ser Ser Leu Thr Cys Asp Ala Leu Thr Glu Leu Leu Ala Lys
220             225             230

ATC ACC AAC ACA GAC GTG GAT TGT CTC AAA GCT TGC CAG GAG CAG ATT       771
Ile Thr Asn Thr Asp Val Asp Cys Leu Lys Ala Cys Gln Glu Gln Ile
235             240             245             250

GAG GCG GTG CTC CTC AAT AGC CTG CAG CAG TAC CGT CAG GAC CAA CGT       819
Glu Ala Val Leu Leu Asn Ser Leu Gln Gln Tyr Arg Gln Asp Gln Arg
            255             260             265

GAC GGA TCC AAG TCG GAG GAT GAA CTG GAC CAA GCC AGC ACC CCT ACA       867
Asp Gly Ser Lys Ser Glu Asp Glu Leu Asp Gln Ala Ser Thr Pro Thr
            270             275             280

GAC GTG CGG GAT ATC GAC CTG TGAGGATGCC AGTTGGGCCG AAAGAGAGAG          918
Asp Val Arg Asp Ile Asp Leu
            285

ACGCGTCCAT AATCTGGTCT CTTCTTCTTT CTGGTTGTTT TTGTTCTTTG TGTTTTAGGG     978

TGAAACTTAA AAAAAAAATT CTGCCCCCAC CTAGATCATA TTTAAAGATC TTTTAGAAGT    1038

GAGAGAAAAA GGTCCTACGA AAACGGAATA ATAAAAAGCA TTTGGTGCCT ATTTGAAGTA    1098

CAGCATAAGG AATCCCTTG TATATGCGAA CAGTTATTGT TTGATTATGT AAAAGTAATA     1158

GTAAAATGCT TACAGGGAAA CCTGCAGAGT AGTTAGAGAA TATGTATGCC TGCAATATGG    1218

GACCAAATTA GAGGAGACTT TTTTTTTTCA TGTTATGAGC TAGCACATAC ACCCCCTTGT    1278

AGTATAATTT CAAGGAACTG TGTACGCCAT TTATCGATGA TTAGATTGCA AAGCAATGAA    1338

CTCAAGAAGG AATTGAAATA AGGAGGGACA TGATGGGGAA GGAGTACAAA ACAATCTCTC    1398

AACATGATTG AACCATTTGG GATGGAGAAG CACCTTTGCT CTCAGCCACC TGTTACTAAG    1458

TCAGGAGTGT AGTTGGATCT CTACATTAAT GTCCTCTTGC TGTCTACAGT AGCTGCTACC    1518

TAAAAAAGA TGTTTTATTT TGCCAGTTGG ACACAGGTGA TTGGCTCCTG GGTTTCATGT     1578

TCTGTGACAT CCTGCTTCTT CTTCCAAATG CAGTTCATTG CAGACACCAC CATATTGCTA    1638

TCTAATGGGG AAATGTAGCT ATGGGCCATA ACCAAAACTC ACATGAAACG GAGGCAGATG    1698

GAGACCAAGG GTGGGATCCA GAATGGAGTC TTTTCTGTTA TTGTATTTAA AAGGGTAATG    1758

TGGCCTTGGC ATTTCTTCTT AGAAAAAAAC TAATTTTTGG TGCTGATTGG CATGTCTGGT    1818

TCACAGTTTA GCATTGTTAT AAACCATTCC ATTCGAAAAG CACTTTGAAA AATTGTTCCC    1878

GAGCGATAGA TGGGATGGTT TATGCAGGAA TTC                                 1911
```

(2) INFORMATION FOR SEQ ID NO:4:

(i) SEQUENCE CHARACTERISTICS:
        (A) LENGTH: 289 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Leu Leu Cys His Glu Val Asp Pro Val Arg Arg Ala Val Arg
 1               5                  10                  15

Asp Arg Asn Leu Leu Arg Asp Asp Arg Val Leu Gln Asn Leu Leu Thr
             20                  25                  30

Ile Glu Glu Arg Tyr Leu Pro Gln Cys Ser Tyr Phe Lys Cys Val Gln
         35                  40                  45

Lys Asp Ile Gln Pro Tyr Met Arg Arg Met Val Ala Thr Trp Met Leu
 50                  55                  60

Glu Val Cys Glu Glu Gln Lys Cys Glu Glu Val Phe Pro Leu Ala
 65                  70                  75                  80

Met Asn Tyr Leu Asp Arg Phe Leu Ala Gly Val Pro Thr Pro Lys Ser
             85                  90                  95

His Leu Gln Leu Leu Gly Ala Val Cys Met Phe Leu Ala Ser Lys Leu
        100                 105                 110

Lys Glu Thr Ser Pro Leu Thr Ala Glu Lys Leu Cys Ile Tyr Thr Asp
115                 120                 125

Asn Ser Ile Lys Pro Gln Glu Leu Leu Glu Trp Glu Leu Val Val Leu
        130                 135                 140

Gly Lys Leu Lys Trp Asn Leu Ala Ala Val Thr Pro His Asp Phe Ile
145                 150                 155                 160

Glu His Ile Leu Arg Lys Leu Pro Gln Gln Arg Glu Lys Leu Ser Leu
            165                 170                 175

Ile Arg Lys His Ala Gln Thr Phe Ile Ala Leu Cys Ala Thr Asp Phe
            180                 185                 190

Lys Phe Ala Met Tyr Pro Pro Ser Met Ile Ala Thr Gly Ser Val Gly
        195                 200                 205

Ala Ala Ile Cys Gly Leu Gln Gln Asp Glu Glu Val Ser Ser Leu Thr
210                 215                 220

Cys Asp Ala Leu Thr Glu Leu Leu Ala Lys Ile Thr Asn Thr Asp Val
225                 230                 235                 240

Asp Cys Leu Lys Ala Cys Gln Glu Gln Ile Glu Ala Val Leu Leu Asn
            245                 250                 255

Ser Leu Gln Gln Tyr Arg Gln Asp Gln Arg Asp Gly Ser Lys Ser Glu
        260                 265                 270

Asp Glu Leu Asp Gln Ala Ser Thr Pro Thr Asp Val Arg Asp Ile Asp
    275                 280                 285

Leu
```

(2) INFORMATION FOR SEQ ID NO:5:

(i) SEQUENCE CHARACTERISTICS:
        (A) LENGTH: 1962 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 101..976

(xi) SEQUENCE DESCRIPTION: SEQ ID NO:5:

```
GAATTCCGAT CCCCAGCCCG CCCGCCCGCG CTCTCCGGCC CGTCGCCTGC CTTGGGACTC      60

GCGAGCCCGC ACTCCCGCCC TGCCTGTTCG CTGCCCGAGT ATG GAG CTG CTG TGT     115
                                            Met Glu Leu Leu Cys
                                             1               5
```

```
TGC GAA GGC ACC CGG CAC GCG CCC CGG GCC GGG CCG GAC CCG CGG CTG          163
Cys Glu Gly Thr Arg His Ala Pro Arg Ala Gly Pro Asp Pro Arg Leu
             10                  15                  20

CTG GGG GAC CAG CGT GTC CTG CAG AGC CTG CTC CGC CTG GAG GAG CGC          211
Leu Gly Asp Gln Arg Val Leu Gln Ser Leu Leu Arg Leu Glu Glu Arg
             25                  30                  35

TAC GTA CCC CGC GCC TCC TAC TTC CAG TGC GTG CAG CGG GAG ATC AAG          259
Tyr Val Pro Arg Ala Ser Tyr Phe Gln Cys Val Gln Arg Glu Ile Lys
             40                  45                  50

CCG CAC ATG CGG AAG ATG CTG GCT TAC TGG ATG CTG GAG GTA TGT GAG          307
Pro His Met Arg Lys Met Leu Ala Tyr Trp Met Leu Glu Val Cys Glu
             55                  60                  65

GAG CAG CGC TGT GAG GAG GAA GTC TTC CCC CTG GCC ATG AAC TAC CTG          355
Glu Gln Arg Cys Glu Glu Glu Val Phe Pro Leu Ala Met Asn Tyr Leu
 70              75                  80                  85

GAT CGC TAC CTG TCT TGC GTC CCC ACC CGA AAG GCG CAG TTG CAG CTC          403
Asp Arg Tyr Leu Ser Cys Val Pro Thr Arg Lys Ala Gln Leu Gln Leu
             90                  95                 100

CTG GGT GCG GTC TGC ATG CTG CTG GCC TCC AAG CTG CGC GAG ACC ACG          451
Leu Gly Ala Val Cys Met Leu Leu Ala Ser Lys Leu Arg Glu Thr Thr
            105                 110                 115

CCC CTG ACC ATC GAA AAA CTG TGC ATC TAC ACC GAC CAC GCT GTC TCT          499
Pro Leu Thr Ile Glu Lys Leu Cys Ile Tyr Thr Asp His Ala Val Ser
            120                 125                 130

CCC CGC CAG TTG CGG GAC TGG GAG GTG CTG GTC CTA GGG AAG CTC AAG          547
Pro Arg Gln Leu Arg Asp Trp Glu Val Leu Val Leu Gly Lys Leu Lys
135                 140                 145

TGG GAC CTG GCT GCT GTG ATT GCA CAT GAT TTC CTG GCC TTC ATT CTG          595
Trp Asp Leu Ala Ala Val Ile Ala His Asp Phe Leu Ala Phe Ile Leu
150                 155                 160                 165

CAC CGG CTC TCT CTG CCC CGT GAC CGA CAG GCC TTG GTC AAA AAG CAT          643
His Arg Leu Ser Leu Pro Arg Asp Arg Gln Ala Leu Val Lys Lys His
            170                 175                 180

GCC CAG ACC TTT TTG GCC CTC TGT GCT ACA GAT TAT ACC TTT GCC ATG          691
Ala Gln Thr Phe Leu Ala Leu Cys Ala Thr Asp Tyr Thr Phe Ala Met
            185                 190                 195

TAC CCG CCA TCC ATG ATC GCC ACG GGC AGC ATT GGG GCT GCA GTG CAA          739
Tyr Pro Pro Ser Met Ile Ala Thr Gly Ser Ile Gly Ala Ala Val Gln
            200                 205                 210

GGC CTG GGT GCC TGC TCC ATG TCC GGG GAT GAG CTC ACA GAG CTG CTG          787
Gly Leu Gly Ala Cys Ser Met Ser Gly Asp Glu Leu Thr Glu Leu Leu
215                 220                 225

GCA GGG ATC ACT GGC ACT GAA GTG GAC TGC CTG CGG GCC TGT CAG GAG          835
Ala Gly Ile Thr Gly Thr Glu Val Asp Cys Leu Arg Ala Cys Gln Glu
230                 235                 240                 245

CAG ATC GAA GCT GCA CTC AGG GAG AGC CTC AGG GAA GCC GCT CAG ACC          883
Gln Ile Glu Ala Ala Leu Arg Glu Ser Leu Arg Glu Ala Ala Gln Thr
            250                 255                 260

AGC TCC AGC CCA GCG CCC AAA GCC CCC CGG GGC TCC AGC AGC CAA GGG          931
Ser Ser Ser Pro Ala Pro Lys Ala Pro Arg Gly Ser Ser Ser Gln Gly
            265                 270                 275

CCC AGC CAG ACC AGC ACT CCT ACA GAT GTC ACA GCC ATA CAC CTG               976
Pro Ser Gln Thr Ser Thr Pro Thr Asp Val Thr Ala Ile His Leu
            280                 285                 290

TAGCCCTGGA GAGGCCCTCT GGAGTGGCCA CTAAGCAGAG GAGGGGCCGC TGCACCCACC        1036

TCCCTGCCTC CAGGAACCAC ACCACATCTA AGCCTGAAGG GGCGTCTGTT CCCCCTTCAC        1096

AAAGCCCAAG GGATCTGGTC CTACCCATCC CCGCAGTGTG CACTAAGGGG CCCGGCCAGC        1156

CATGTCTGCA TTTCGGTGGC TAGTCAAGCT CCTCCTCCCT GCATCTGACC AGCAGCGCCT        1216
```

-continued

```
TTCCCAACTC TAGCTGGGGG TGGGCCAGGC TGATGGGACA GAATTGGATA CATACACCAG    1276

CATTCCTTTT GAACGCCCCC CCCCACCCCT GGGGGCTCTC ATGTTTTCAA CTGCCAAAAT    1336

GCTCTAGTGC CTTCTAAAGG TGTTGTCCCT TCTAGGGTTA TTGCATTTGG ATTGGGGTCC    1396

CTCTAAAATT TAATGCATGA TAGACACATA TGAGGGGGAA TAGTCTAGAT GGCTCCTCTC    1456

AGTACTTTGG AGGCCCCTAT GTAGTCCGTG CTGACAGCTG CTCCTAGAGG GAGGGGCCTA    1516

GGCTCAGCCA GAGAAGCTAT AAATTCCTCT TTGCTTTGCT TTCTGCTCAG CTTCTCCTGT    1576

GTGATTGACA GCTTTGCTGC TGAAGGCTCA TTTTAATTTA TTAATTGCTT TGAGCACAAC    1636

TTTAAGAGGA CGTAATGGGG TCCTGGCCAT CCCACAAGTG GTGGTAACCC TGGTGGTTGC    1696

TGTTTTCCTC CCTTCTGCTA CTGGCAAAAG GATCTTTGTG GCCAAGGAGC TGCTATAGCC    1756

TGGGGTGGGG TCATGCCCTC CTCTCCCATT GTCCCTCTGC CCCATCCTCC AGCAGGGAAA    1816

ATGCAGCAGG GATGCCCTGG AGGTGCTGAG CCCCTGTCTA GAGAGGGAGG CAAGCCTGTT    1876

GACACAGGTC TTTCCTAAGG CTGCAAGGTT TAGGCTGGTG GCCCAGGACC ATCATCCTAC    1936

TGTAATAAAG ATGATTGTGG GAATTC                                         1962
```

(2) INFORMATION FOR SEQ ID NO:6:

(i) SEQUENCE CHARACTERISTICS:
        (A) LENGTH: 292 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Leu Leu Cys Cys Glu Gly Thr Arg His Ala Pro Arg Ala Gly
 1               5                  10                  15

Pro Asp Pro Arg Leu Leu Gly Asp Gln Arg Val Leu Gln Ser Leu Leu
            20                  25                  30

Arg Leu Glu Glu Arg Tyr Val Pro Arg Ala Ser Tyr Phe Gln Cys Val
        35                  40                  45

Gln Arg Glu Ile Lys Pro His Met Arg Lys Met Leu Ala Tyr Trp Met
    50                  55                  60

Leu Glu Val Cys Glu Glu Gln Arg Cys Glu Glu Glu Val Phe Pro Leu
65                  70                  75                  80

Ala Met Asn Tyr Leu Asp Arg Tyr Leu Ser Cys Val Pro Thr Arg Lys
                85                  90                  95

Ala Gln Leu Gln Leu Leu Gly Ala Val Cys Met Leu Leu Ala Ser Lys
           100                 105                 110

Leu Arg Glu Thr Thr Pro Leu Thr Ile Glu Lys Leu Cys Ile Tyr Thr
       115                 120                 125

Asp His Ala Val Ser Pro Arg Gln Leu Arg Asp Trp Glu Val Leu Val
   130                 135                 140

Leu Gly Lys Leu Lys Trp Asp Leu Ala Ala Val Ile Ala His Asp Phe
145                 150                 155                 160

Leu Ala Phe Ile Leu His Arg Leu Ser Leu Pro Arg Asp Arg Gln Ala
                165                 170                 175

Leu Val Lys Lys His Ala Gln Thr Phe Leu Ala Leu Cys Ala Thr Asp
           180                 185                 190

Tyr Thr Phe Ala Met Tyr Pro Pro Ser Met Ile Ala Thr Gly Ser Ile
       195                 200                 205

Gly Ala Ala Val Gln Gly Leu Gly Ala Cys Ser Met Ser Gly Asp Glu
   210                 215                 220
```

```
Leu Thr Glu Leu Leu Ala Gly Ile Thr Gly Thr Glu Val Asp Cys Leu
225                 230                 235                 240

Arg Ala Cys Gln Glu Gln Ile Glu Ala Ala Leu Arg Glu Ser Leu Arg
            245                 250                 255

Glu Ala Ala Gln Thr Ser Ser Ser Pro Ala Pro Lys Ala Pro Arg Gly
            260                 265                 270

Ser Ser Ser Gln Gly Pro Ser Gln Thr Ser Thr Pro Thr Asp Val Thr
            275                 280                 285

Ala Ile His Leu
            290
```

(2) INFORMATION FOR SEQ ID NO:7:

(i) SEQUENCE CHARACTERISTICS:
        (A) LENGTH: 819 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Gln Leu Cys Cys Glu Val Glu Thr Ile Arg Arg Ala Tyr Pro Asp Ala
1               5                   10                  15

Asn Leu Leu Asn Asp Arg Val Leu Arg Ala Met Leu Lys Ala Glu Glu
            20                  25                  30

Thr Cys Ala Pro Ser Val Ser Tyr Phe Lys Cys Val Gln Lys Glu Val
            35                  40                  45

Leu Pro Ser Met Arg Lys Ile Val Ala Thr Trp Met Leu Glu Val Cys
50                  55                  60

Glu Glu Gln Lys Cys Glu Glu Val Phe Pro Leu Ala Met Asn Tyr
65                  70                  75                  80

Leu Asp Arg Phe Leu Ser Leu Glu Pro Val Lys Lys Ser Arg Leu Gln
            85                  90                  95

Leu Leu Gly Ala Thr Cys Met Phe Ser Ile Val Leu Glu Asp Glu Lys
            100                 105                 110

Pro Val Ser Val Asn Glu Val Pro Asp Tyr His Glu Asp Ile His Thr
            115                 120                 125

Tyr Leu Arg Glu Met Glu Val Lys Cys Lys Pro Lys Val Gly Tyr Met
            130                 135                 140

Lys Lys Gln Pro Asp Ile Thr Asn Ser Met Arg Ala Ile Leu Val Asp
145                 150                 155                 160

Trp Leu Val Glu Val Gly Glu Glu Tyr Lys Leu Gln Asn Glu Thr Leu
                165                 170                 175

His Leu Ala Val Asn Tyr Ile Asp Arg Phe Leu Ser Ser Met Ser Val
            180                 185                 190

Leu Arg Gly Lys Leu Gln Leu Val Gly Thr Ala Ala Met Leu Lys Glu
            195                 200                 205

Leu Pro Pro Arg Asn Asp Arg Gln Arg Phe Leu Glu Val Val Gln Tyr
            210                 215                 220

Gln Met Asp Ile Leu Glu Tyr Phe Arg Glu Ser Glu Lys Lys His Arg
225                 230                 235                 240

Pro Lys Pro Arg Tyr Met Arg Arg Gln Lys Asp Ile Ser His Asn Met
            245                 250                 255

Arg Ser Ile Leu Ile Asp Trp Leu Val Glu Val Ser Glu Glu Tyr Lys
            260                 265                 270
```

```
Leu Asp Thr Glu Thr Leu Tyr Leu Ser Val Phe Tyr Leu Asp Arg Phe
    275                 280                 285

Leu Ser Gln Met Ala Val Val Arg Ser Lys Leu Gln Leu Val Gly Thr
    290                 295                 300

Ala Ala Met Tyr Val Asn Asp Val Asp Ala Glu Asp Gly Ala Asp Pro
305                 310                 315                 320

Asn Leu Cys Ser Glu Tyr Val Lys Asp Ile Tyr Ala Tyr Leu Arg Gln
                325                 330                 335

Leu Glu Glu Glu Gln Ala Val Arg Pro Lys Tyr Leu Leu Gly Arg Glu
                340                 345                 350

Val Thr Gly Asn Met Arg Ala Ile Leu Ile Asp Trp Leu Val Gln Val
            355                 360                 365

Gln Met Lys Phe Arg Leu Leu Gln Glu Thr Met Tyr Met Thr Val Ser
    370                 375                 380

Ile Ile Asp Arg Phe Met Gln Asn Asn Cys Val Pro Lys Lys Met Leu
385                 390                 395                 400

Gln Leu Val Gly Val Thr Ala Met Phe Trp Asp Asp Leu Asp Ala Glu
                405                 410                 415

Asp Trp Ala Asp Pro Leu Met Val Ser Glu Tyr Val Val Asp Ile Phe
                420                 425                 430

Glu Tyr Leu Asn Glu Leu Glu Ile Glu Thr Met Pro Ser Pro Thr Tyr
            435                 440                 445

Met Asp Arg Gln Lys Glu Leu Ala Trp Lys Met Arg Gly Ile Leu Thr
450                 455                 460

Asp Trp Leu Ile Glu Val His Ser Arg Phe Arg Leu Leu Pro Glu Thr
465                 470                 475                 480

Leu Phe Leu Ala Val Asn Ile Ile Asp Arg Phe Leu Ser Leu Arg Val
                485                 490                 495

Cys Ser Leu Asn Lys Leu Gln Leu Val Gly Ile Ala Ala Leu Phe Ile
                500                 505                 510

Glu Leu Ser Asn Ala Glu Leu Leu Thr His Tyr Glu Thr Ile Gln Glu
            515                 520                 525

Tyr His Glu Glu Ile Ser Gln Asn Val Leu Val Gln Ser Ser Lys Thr
    530                 535                 540

Lys Pro Asp Ile Lys Leu Ile Asp Gln Gln Pro Glu Met Asn Pro His
545                 550                 555                 560

Gln Thr Arg Glu Ala Ile Val Thr Phe Leu Tyr Gln Leu Ser Val Met
                565                 570                 575

Thr Arg Val Ser Asn Gly Ile Phe Phe His Ser Val Arg Phe Tyr Asp
                580                 585                 590

Arg Tyr Cys Ser Lys Arg Val Val Leu Lys Asp Gln Ala Lys Leu Val
            595                 600                 605

Val Gly Thr Cys Leu Trp Pro Asn Leu Val Lys Arg Glu Leu Gln Ala
    610                 615                 620

His His Ser Ala Ile Ser Glu Tyr Asn Asn Asp Gln Leu Asp His Tyr
625                 630                 635                 640

Phe Arg Leu Ser His Thr Glu Arg Pro Leu Tyr Asn Leu Asn Ser Gln
                645                 650                 655

Pro Gln Val Asn Pro Lys Met Arg Phe Leu Ile Phe Asp Phe Ile Met
                660                 665                 670

Tyr Cys His Thr Arg Leu Asn Leu Ser Thr Ser Thr Leu Phe Leu Thr
            675                 680                 685

Phe Thr Ile Leu Asp Lys Tyr Ser Ser Arg Phe Ile Ile Lys Ser Tyr
    690                 695                 700
```

```
Asn Tyr Gln Leu Leu Ser Leu Thr Ala Leu Trp Val Ala Ser Lys Met
705                 710                 715                 720

Lys Glu Thr Ile Pro Leu Thr Ala Glu Lys Leu Cys Ile Tyr Thr Asp
                725                 730                 735

Gly Ser Ile Arg Pro Glu Leu Leu Gln Met Glu Leu Leu Leu Val
                740                 745                 750

Asn Lys Leu Lys Trp Asn Leu Ala Ala Met Thr Pro His Glu Phe Ile
                755                 760                 765

Glu His Phe Leu Ser Lys Met Pro Glu Ala Glu Asn Lys Gln Ile
            770                 775                 780

Ile Arg Lys His Ala Gln Thr Phe Val Ala Leu Cys Ala Thr Asp Val
785                 790                 795                 800

Lys Phe Ile Ser Asn Pro Pro Ser Met Val Ala Ala Gly Ser Val Val
                805                 810                 815

Ala Ala Val
```

(2) INFORMATION FOR SEQ ID NO:8:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Leu Ala Ser Lys Phe Glu Glu Ile Tyr Pro Pro Glu Val Ala Glu Phe
1               5                   10                  15

Val Tyr Ile Thr Val Asp Thr Tyr Thr Lys Lys Gln Val Leu Arg Met
                20                  25                  30

Glu His Leu Val Leu Lys Val Leu Thr Phe Asp Leu Ala Ala Pro Thr
            35                  40                  45

Val Asn Gln Phe Leu Thr Gln Tyr Phe Leu His Gln Gln Asn Cys Lys
50                  55                  60

Val Glu Ser Leu Ala Met Phe Leu Gly Glu Leu Ser Leu Ile Asp Ala
65                  70                  75                  80

Asp Pro Tyr Leu Lys Tyr Leu Pro Ser Val Ile Ala Gly Ala Ala Phe
                85                  90                  95

His Leu Ala Leu
            100
```

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ile Ala Ala Lys Tyr Glu Glu Ile Tyr Pro Pro Glu Val Gly Glu Phe
1               5                   10                  15

Val Phe Leu Thr Asp Asp Ser Tyr Thr Lys Ala Gln Val Leu Arg Met
                20                  25                  30

Glu Gln Val Ile Leu Lys Ile Leu Ser Phe Asp Leu Cys Thr Pro Thr
            35                  40                  45
```

```
Ala Tyr Val Phe Ile Asn Thr Tyr Ala Val Leu Cys Asp Met Pro Glu
    50                  55                  60

Lys Leu Lys Tyr Met Thr Leu Tyr Ile Ser Glu Leu Ser Leu Met Glu
65                  70                  75                  80

Gly Glu Thr Tyr Leu Gln Tyr Leu Pro Ser Leu Met Ser Ser Ala Ser
                85                  90                  95

Val Ala Leu Ala Arg
            100
```

(2) INFORMATION FOR SEQ ID NO:10:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Ile Ala Ser Lys Tyr Glu Glu Met Tyr Pro Pro Glu Ile Gly Asp Phe
1               5                   10                  15

Ala Phe Val Thr Asp Asn Thr Tyr Thr Lys His Gln Ile Arg Gln Met
                20                  25                  30

Glu Met Lys Ile Leu Arg Ala Leu Asn Phe Gly Leu Gly Arg Pro Leu
                35                  40                  45

Pro Leu His Phe Leu Arg Arg Ala Ser Lys Ile Gly Glu Val Asp Val
    50                  55                  60

Glu Gln His Thr Leu Ala Lys Tyr Leu Met Glu Leu Thr Met Leu Asp
65                  70                  75                  80

Tyr Asp Met Val His Phe Pro Pro Ser Gln Ile Ala Ala Gly Ala Phe
                85                  90                  95

Cys Leu Ala Leu
            100
```

(2) INFORMATION FOR SEQ ID NO:11:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Ile Ala Ser Lys Tyr Glu Glu Val Met Cys Pro Ser Val Gln Asn Phe
1               5                   10                  15

Val Tyr Met Ala Asp Gly Gly Tyr Asp Glu Glu Ile Leu Gln Ala
                20                  25                  30

Glu Arg Tyr Ile Leu Arg Val Leu Glu Phe Asn Leu Ala Tyr Pro Asn
                35                  40                  45

Pro Met Asn Phe Leu Arg Arg Ile Ser Lys Ala Asp Phe Tyr Asp Ile
    50                  55                  60

Gln Thr Arg Thr Val Ala Lys Tyr Leu Val Glu Ile Gly Leu Leu Asp
65                  70                  75                  80

His Lys Leu Leu Pro Tyr Pro Ser Gln Gln Cys Ala Ala Ala Met
                85                  90                  95

Tyr Leu Ala Arg
            100
```

(2) INFORMATION FOR SEQ ID NO:12:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Leu Ala Ala Lys Thr Trp Gly Arg Leu Ser Glu Leu Val His Tyr Cys
1               5                   10                  15

Gly Gly Ser Asp Leu Phe Asp Glu Ser Met Phe Ile Gln Met Glu Arg
            20                  25                  30

His Ile Leu Asp Thr Leu Asn Trp Asp Val Tyr Glu Pro Met Ile Asn
        35                  40                  45

Asp Tyr Ile
    50

(2) INFORMATION FOR SEQ ID NO:13:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Ile Ser Ser Lys Phe Trp Asp Arg Met Ala Thr Leu Lys Val Leu Gln
1               5                   10                  15

Asn Leu Cys Cys Asn Gln Tyr Ser Ile Lys Gln Phe Thr Thr Met Glu
            20                  25                  30

Met His Leu Phe Lys Ser Leu Asp Trp Ser Ile Ser Ala Thr Phe Asp
        35                  40                  45

Ser Tyr Ile
    50

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CCCAAAAACT GTCTTT                                                              16

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CCCAAAAACT GTCTTTAAAA GAGAGAGAGA G                                             31

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

TGCATAACCC TGAGCGGTGG GGGAGGAGGG TT        32

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TGCATAACCC TGAGCGGTGG GGGAGGAGGG TT        32

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

TGCATAACCC TGAGCGGTGG GGGAGGAGGG TT        32

(2) INFORMATION FOR SEQ ID NO:19:

(i) SEQUENCE CHARACTERISTICS:
        (A) LENGTH: 295 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Met Glu His Gln Leu Leu Cys Cys Glu Val Glu Thr Ile Arg Arg Ala
  1               5                  10                  15

Tyr Pro Asp Ala Asn Leu Leu Asn Asp Arg Val Leu Arg Ala Met Leu
                 20                  25                  30

Lys Ala Glu Glu Thr Cys Ala Pro Ser Val Ser Tyr Phe Lys Cys Val
             35                  40                  45

Gln Lys Glu Val Leu Pro Ser Met Arg Lys Ile Val Ala Thr Trp Met
 50                  55                  60

Leu Glu Val Cys Glu Glu Gln Lys Cys Glu Glu Val Phe Pro Leu
 65                  70                  75                  80

Ala Met Asn Tyr Leu Asp Arg Phe Leu Ser Leu Glu Pro Val Lys Lys
                 85                  90                  95

Ser Arg Leu Gln Leu Leu Gly Ala Thr Cys Met Phe Val Ala Ser Lys
                100                 105                 110

Met Lys Glu Thr Ile Pro Leu Thr Ala Glu Lys Leu Cys Ile Tyr Thr
```

```
            115                 120                 125
Asp Gly Ser Ile Arg Pro Glu Glu Leu Leu Gln Met Glu Leu Leu Leu
130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
                180                 185                 190

Val Lys Phe Ile Ser Asn Pro Pro Ser Met Val Ala Ala Gly Ser Val
                195                 200                 205

Val Ala Ala Val Lys Gly Leu Asn Leu Arg Ser Pro Asn Asn Phe Leu
210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
                260                 265                 270

Glu Glu Glu Glu Glu Glu Glu Val Asp Leu Ala Cys Thr Pro Thr
                275                 280                 285

Asp Val Arg Asp Val Asp Ile
290                 295

(2) INFORMATION FOR SEQ ID NO:20:

(i) SEQUENCE CHARACTERISTICS:
        (A) LENGTH: 295 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Met Glu Asn Gln Leu Cys Cys Glu Val Glu Thr Ile Arg Arg Ala
1               5                   10                  15

Tyr Pro Asp Thr Asn Leu Leu Asn Asp Arg Val Leu Arg Ala Met Leu
                20                  25                  30

Lys Thr Glu Glu Thr Cys Ala Pro Ser Val Ser Tyr Phe Lys Cys Val
                35                  40                  45

Gln Lys Glu Ile Val Pro Ser Met Arg Lys Ile Val Ala Thr Trp Met
50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Leu Lys Lys
                85                  90                  95

Ser Arg Leu Gln Leu Leu Gly Ala Thr Cys Met Phe Val Ala Ser Lys
                100                 105                 110

Met Lys Glu Thr Ile Pro Leu Thr Ala Glu Lys Leu Cys Ile Tyr Thr
                115                 120                 125

Asp Asn Ser Ile Arg Pro Glu Glu Leu Leu Gln Met Glu Leu Leu Leu
                130                 135                 140

Val Asn Lys Leu Lys Trp Asn Leu Ala Ala Met Thr Pro His Asp Phe
145                 150                 155                 160

Ile Glu His Phe Leu Ser Lys Met Pro Asp Ala Glu Glu Asn Lys Gln
                165                 170                 175
```

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Met
            195                 200                 205

Val Ala Ala Met Gln Gly Leu Asn Leu Gly Ser Pro Asn Asn Phe Leu
            210                 215                 220

Ser Arg Tyr Arg Thr Thr His Phe Leu Ser Arg Val Ile Lys Cys Asp
225                 230                 235                 240

Pro Asp Cys Leu Arg Ala Cys Gln Glu Gln Ile Glu Ala Leu Leu Glu
            245                 250                 255

Ser Ser Leu Arg Gln Ala Gln Gln Asn Met Asp Pro Lys Ala Thr Glu
            260                 265                 270

Glu Glu Gly Glu Val Glu Glu Ala Gly Leu Ala Cys Thr Pro Thr
            275                 280                 285

Asp Val Arg Asp Val Asp Ile
            290                 295

(2) INFORMATION FOR SEQ ID NO:21:

(i) SEQUENCE CHARACTERISTICS:
        (A) LENGTH: 189 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Met Glu Leu Leu Cys His Glu Val Asp Pro Val Arg Arg Ala Val Arg
1               5                   10                  15

Asp Arg Asn Leu Leu Arg Asp Asp Arg Val Leu Gln Asn Leu Leu Thr
            20                  25                  30

Ile Glu Glu Arg Tyr Leu Pro Gln Cys Ser Tyr Phe Lys Cys Val Gln
            35                  40                  45

Lys Asp Ile Gln Pro Tyr Met Arg Arg Met Val Ala Thr Trp Met Leu
50                  55                  60

Glu Val Cys Glu Glu Gln Lys Cys Glu Glu Val Phe Pro Leu Ala
65                  70                  75                  80

Met Asn Tyr Leu Asp Arg Phe Leu Ala Gly Val Pro Thr Pro Lys Ser
            85                  90                  95

His Pro Pro Ser Met Ile Ala Thr Gly Ser Val Gly Ala Ala Ile Cys
            100                 105                 110

Gly Leu Lys Gln Asp Glu Glu Val Ser Ser Leu Thr Cys Asp Ala Leu
            115                 120                 125

Thr Glu Leu Leu Ala Lys Ile Thr Asn Thr Asp Val Asp Cys Leu Lys
            130                 135                 140

Ala Cys Gln Glu Gln Ile Glu Ala Val Leu Leu Asn Ser Leu Gln Gln
145                 150                 155                 160

Tyr Arg Gln Asp Gln Arg Asp Gly Ser Lys Ser Glu Asp Glu Leu Asp
            165                 170                 175

Gln Ala Ser Thr Pro Thr Asp Val Arg Asp Ile Asp Leu
            180                 185

(2) INFORMATION FOR SEQ ID NO:22:

(i) SEQUENCE CHARACTERISTICS:
        (A) LENGTH: 236 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:22:

Met Arg Arg Met Val Ala Thr Trp Met Leu Glu Val Cys Glu Gln
1               5                   10                  15

Lys Cys Glu Glu Glu Val Phe Pro Leu Ala Met Asn Tyr Leu Asp Arg
            20                  25                  30

Phe Leu Ala Gly Val Pro Thr Pro Lys Thr His Leu Gln Leu Leu Gly
        35                  40                  45

Ala Val Cys Met Phe Leu Ala Ser Lys Leu Lys Glu Thr Ile Pro Leu
50                  55                  60

Thr Ala Glu Lys Leu Cys Ile Tyr Thr Asp Asn Ser Val Lys Pro Gln
65                  70                  75                  80

Glu Leu Leu Glu Trp Glu Leu Val Val Leu Gly Lys Leu Lys Trp Asn
                85                  90                  95

Leu Ala Ala Val Thr Pro His Asp Phe Ile Glu His Ile Leu Arg Lys
            100                 105                 110

Leu Pro Gln Gln Lys Glu Lys Leu Ser Leu Ile Arg Lys His Ala Gln
        115                 120                 125

Thr Phe Ile Ala Leu Cys Ala Thr Asp Phe Lys Phe Ala Met Tyr Pro
130                 135                 140

Pro Ser Met Ile Ala Thr Gly Ser Val Gly Ala Ala Ile Cys Gly Leu
145                 150                 155                 160

Gln Gln Asp Asp Glu Val Asn Thr Leu Thr Cys Asp Ala Leu Thr Glu
            165                 170                 175

Leu Leu Ala Lys Ile Thr His Thr Asp Val Asp Cys Leu Lys Ala Cys
        180                 185                 190

Gln Glu Gln Ile Glu Ala Leu Leu Leu Asn Ser Leu Gln Gln Phe Arg
195                 200                 205

Gln Glu Gln His Asn Ala Gly Ser Lys Ser Val Glu Asp Pro Asp Gln
210                 215                 220

Ala Thr Thr Pro Thr Asp Val Arg Asp Val Asp Leu
225                 230                 235

(2) INFORMATION FOR SEQ ID NO:23:

(i) SEQUENCE CHARACTERISTICS:
        (A) LENGTH: 292 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Met Glu Leu Leu Cys Cys Glu Gly Thr Arg His Ala Pro Arg Ala Gly
1               5                   10                  15

Pro Asp Pro Arg Leu Leu Gly Asp Gln Arg Val Leu Gln Ser Leu Leu
            20                  25                  30

Arg Leu Glu Glu Arg Tyr Val Pro Arg Ala Ser Tyr Phe Gln Cys Val
        35                  40                  45

Gln Arg Glu Ile Lys Pro His Met Arg Lys Met Leu Ala Tyr Trp Met
50                  55                  60

Leu Glu Val Cys Glu Glu Gln Arg Cys Glu Glu Glu Val Phe Pro Leu
65                  70                  75                  80
```

```
Ala Met Asn Tyr Leu Asp Arg Tyr Leu Ser Cys Val Pro Thr Arg Lys
                85                  90                  95

Ala Gln Leu Gln Leu Leu Gly Ala Val Cys Met Leu Leu Ala Ser Lys
            100                 105                 110

Leu Arg Glu Thr Thr Pro Leu Thr Ile Glu Lys Leu Cys Ile Tyr Thr
        115                 120                 125

Asp His Ala Val Ser Pro Arg Gln Leu Arg Asp Trp Glu Val Leu Val
    130                 135                 140

Leu Gly Lys Leu Lys Trp Asp Leu Ala Ala Val Ile Ala His Asp Phe
145                 150                 155                 160

Leu Ala Phe Ile Leu His Arg Leu Ser Leu Pro Arg Asp Arg Gln Ala
                165                 170                 175

Leu Val Lys Lys His Ala Gln Thr Phe Leu Ala Leu Cys Ala Thr Asp
            180                 185                 190

Tyr Thr Phe Ala Met Tyr Pro Pro Ser Met Ile Ala Thr Gly Ser Ile
        195                 200                 205

Gly Ala Ala Val Gln Gly Leu Gly Ala Cys Ser Met Ser Gly Asp Glu
    210                 215                 220

Leu Thr Glu Leu Leu Ala Gly Ile Thr Gly Thr Glu Val Asp Cys Leu
225                 230                 235                 240

Arg Ala Cys Gln Glu Gln Ile Glu Ala Ala Leu Arg Glu Ser Leu Arg
                245                 250                 255

Glu Ala Ala Gln Thr Ser Ser Ser Pro Ala Pro Lys Ala Pro Arg Gly
            260                 265                 270

Ser Ser Ser Gln Gly Pro Ser Gln Thr Ser Thr Pro Thr Asp Val Thr
        275                 280                 285

Ala Ile His Leu
    290

(2) INFORMATION FOR SEQ ID NO:24:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Met Arg Lys Met Leu Ala Tyr Trp Met Leu Glu Val Cys Glu Glu Gln
1               5                   10                  15

Arg Cys Glu Glu Asp Val Phe Pro Leu Ala Met Asn Tyr Leu Asp Arg
            20                  25                  30

Tyr Leu Ser Cys Val Pro Thr Arg Lys Ala Gln Leu Gln Leu Leu Gly
        35                  40                  45

Thr Val Cys Ile Leu Leu Ala Ser Lys Leu Arg Glu Thr Thr Pro Leu
    50                  55                  60

Thr Ile Glu Lys Leu Cys Ile Tyr Thr Asp Gln Ala Val Ala Pro Trp
65                  70                  75                  80

Gln Leu Arg Glu Trp Glu Val Leu Val Leu Gly Lys Leu Lys Trp Asp
                85                  90                  95

Leu Ala Ala Val Ile Ala His Asp Phe Leu Ala Leu Ile Leu His Arg
            100                 105                 110

Leu Ser Leu Pro Ser Asp Arg Gln Ala Leu Val Lys Lys His Ala Gln
        115                 120                 125

Thr Phe Leu Ala Leu Cys Ala Thr Asp Tyr Thr Phe Ala Met Tyr Pro
```

```
            130                 135                 140
Pro Ser Met Ile Ala Thr Gly Ser Ile Gly Ala Ala Val Ile Gly Leu
145                 150                 155                 160

Gly Ala Cys Ser Met Ser Ala Asp Glu Leu Thr Glu Leu Leu Ala Gly
                165                 170                 175

Ile Thr Gly Thr Glu Val Asp Cys Leu Arg Ala Cys Gln Glu Gln Ile
                180                 185                 190

Glu Ala Ala Leu Arg Glu Ser Leu Arg Glu Ala Ala Gln Thr Ala Pro
                195                 200                 205

Ser Pro Val Pro Lys Ala Pro Arg Gly Ser Ser Gln Gly Pro Ser
        210                 215                 220

Gln Thr Ser Thr Pro Thr Asp Val Thr Ala Ile His Leu
225                 230                 235
```

(2) INFORMATION FOR SEQ ID NO:25:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Met Arg Ala Ile Leu Val Asp Trp Leu Val Glu Val Gly Glu Glu Tyr
1               5                   10                  15

Lys Leu Gln Asn Glu Thr Leu His Leu Ala Val Asn Tyr Ile Asp Arg
                20                  25                  30

Phe Leu Ser Ser Met Ser Val Leu Arg Gly Lys Leu Gln Leu Val Gly
                35                  40                  45

Thr Ala Ala Met Leu Leu Ala Ser Lys Phe Glu Glu Ile Tyr Pro Pro
50                  55                  60

Glu Val Ala Glu Phe Val Tyr Ile Thr Asp Asp Thr Tyr Thr Lys Lys
65                  70                  75                  80

Gln Val Leu Arg Met Glu His Leu Val Leu Lys Val Leu Thr Phe Asp
                85                  90                  95

Leu Ala Ala Pro Thr Val Asn Gln Phe Leu
                100                 105
```

(2) INFORMATION FOR SEQ ID NO:26:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Met Arg Ala Ile Leu Ile Asp Trp Leu Val Gln Val Gln Met Lys Phe
1               5                   10                  15

Arg Leu Leu Gln Glu Thr Met Tyr Met Thr Val Ser Ile Ile Asp Arg
                20                  25                  30

Phe Met Gln Asn Asn Cys Val Pro Lys Lys Met Leu Gln Leu Val Gly
                35                  40                  45

Val Thr Ala Met Phe Ile Ala Ser Lys Tyr Glu Glu Met Tyr Pro Pro
                50                  55                  60

Glu Ile Gly Asp Phe Ala Phe Val Thr Asp Asn Thr Tyr Thr Lys His
```

```
              65                  70                  75                  80
Gln Ile Arg Gln Met Glu Met Lys Ile Leu Arg Ala Leu Asn Phe Gly
                     85                  90                  95

Leu Gly Arg Pro Leu Pro Leu His Phe Leu
                100                 105
```

(2) INFORMATION FOR SEQ ID NO:27:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Met Arg Ala Ile Leu Val Asp Trp Leu Val Gln Val His Ser Lys Phe
1                    5                  10                  15

Arg Leu Leu Gln Glu Thr Leu Tyr Met Cys Val Gly Ile Met Asp Arg
                    20                  25                  30

Phe Leu Gln Val Gln Pro Val Ser Arg Lys Lys Leu Gln Leu Val Gly
                35                  40                  45

Ile Thr Ala Leu Leu Leu Ala Ser Lys Tyr Glu Glu Met Phe Ser Pro
            50                  55                  60

Asn Ile Glu Asp Phe Val Tyr Ile Thr Asp Asn Ala Tyr Thr Ser Ser
65                  70                  75                  80

Gln Ile Arg Glu Met Glu Thr Leu Ile Leu Lys Glu Leu Lys Phe Glu
                    85                  90                  95

Leu Gly Arg Pro Leu Pro Leu His Phe Leu
                100                 105
```

(2) INFORMATION FOR SEQ ID NO:28:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Leu Gln Ile Phe Phe Thr Asn Val Ile Gln Ala Leu Gly Glu His Leu
1                    5                  10                  15

Lys Leu Arg Gln Gln Val Ile Ala Thr Ala Thr Val Tyr Phe Lys Arg
                    20                  25                  30

Phe Tyr Ala Arg Tyr Ser Leu Lys Ser Ile Asp Pro Val Leu Met Ala
                35                  40                  45

Pro Thr Cys Val Phe Leu Ala Ser Lys Val Glu Glu Ile Leu Lys Thr
            50                  55                  60

Arg Phe Ser Tyr Ala Phe Pro Lys Glu Phe Pro Tyr Arg Met Asn His
65                  70                  75                  80

Ile Leu Glu Cys Glu Phe Tyr Leu Leu Glu Leu Met Asp Cys Cys Leu
                    85                  90                  95

Ile Val Tyr His Pro Tyr Arg Pro Leu
                100                 105
```

(2) INFORMATION FOR SEQ ID NO:29:

(i) SEQUENCE CHARACTERISTICS:

```
            (A) LENGTH: 105 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:29:

Met Arg Ala Ile Leu Leu Asp Trp Leu Met Glu Val Cys Glu Val Tyr
1               5                   10                  15

Lys Leu His Arg Glu Thr Phe Tyr Leu Ala Gln Asp Phe Phe Asp Arg
            20                  25                  30

Tyr Met Ala Glu Asn Val Val Lys Thr Leu Leu Gln Leu Ile Gly Ile
        35                  40                  45

Ser Ser Leu Phe Ile Ala Ala Lys Leu Glu Glu Ile Tyr Pro Pro Lys
    50                  55                  60

Leu His Gln Phe Ala Tyr Val Thr Asp Gly Ala Cys Ser Gly Asp Glu
65                  70                  75                  80

Ile Leu Thr Met Glu Leu Met Ile Met Lys Ala Leu Lys Trp Arg Leu
                85                  90                  95

Ser Pro Leu Thr Ile Val Ser Trp Leu
                100                 105

(2) INFORMATION FOR SEQ ID NO:30:

(i) SEQUENCE CHARACTERISTICS:
            (A) LENGTH: 1462 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: join(378..569, 662..1000, 1040..1189,
                1191..1292, 1292..1324)

(xi) SEQUENCE DESCRIPTION: SEQ ID NO:30:

TGATCAAGTT GACACTCAAT ATTAACCCTC ATAGACTGTG ATCCCTATGT TGCTGCCTTC        60

CCTCGTTTCT ATTGCTCTTT GGCCCCAACC CAAATAAGGT TCCTTGGGAC ACACTAAAGA       120

AGGAGGTGGA GTTCGAAGGG GAGGAGAGAT GTGAGCGAGG CAGGCAGGGA AGCTCTGCTC       180

GCCCACTGCC CAATCCTCAC CTCTCTTCTC CTCCACCTTC TGTCTCTGCC CTCACCTCTC       240

CTCTGAAAAC CCCCTATTGA GCCAAAGGAA GGAGATGAGG GGAATGCTTT TGCCTTCCCC       300

CTCCAAAACA AAAACAAAAA CAAACACACT TTTCCAGTCC AGAGAAAGCA GGGGAGTGAG       360

GGGTCACAGA GCTGGCC ATG CAG CTG CTG GGC TGT GAG GTA GAC CCG GTC         410
                   Met Gln Leu Leu Gly Cys Glu Val Asp Pro Val
                     1               5                  10

CTC AGA GCC ACG AGG GAC TGC AAC CTA CTC CAA GTT GAC CGT GTC CTG         458
Leu Arg Ala Thr Arg Asp Cys Asn Leu Leu Gln Val Asp Arg Val Leu
            15                  20                  25

AAG AAC CTG CTT GCT ATC AAG AAG CGC TAC CTT CAG TAA TGC TCC TAC         506
Lys Asn Leu Leu Ala Ile Lys Lys Arg Tyr Leu Gln     Cys Ser Tyr
        30                  35                  40

TTC AAG TGT GTG CAG AAG GCC ATC CAG CCG TAC ATG CAC AGG ATG GTG         554
Phe Lys Cys Val Gln Lys Ala Ile Gln Pro Tyr Met His Arg Met Val
    45                  50                  55

CCA CTT CTG ATG GTG GCCATTTGAT TGGTGCCACT TCTGATGGTG GCCAACATGA         609
Pro Leu Leu Met Val
60
```

```
TTGAACCATT TGGGATGGAA AAGCACCTTT ACTCTCAGCC ACCTGTTAAC TA ATG         664
                                                            Met
                                                            65

CTG GAG GTC TGT GAG GAA CAG AAG TGT GAA GAA AAG GTT TTC CCT CTG      712
Leu Glu Val Cys Glu Glu Gln Lys Cys Glu Glu Lys Val Phe Pro Leu
            70                  75                  80

GCC ACG ATT TAC CTG GAC TGT TTC TTC GCC AGG ATC CCA ACT TCA AAG      760
Ala Thr Ile Tyr Leu Asp Cys Phe Phe Ala Arg Ile Pro Thr Ser Lys
                85                  90                  95

TCC CAT CTG CAA CTC CTG GGT GCT GTC TGC ATG TTC CTG GCC TCC AGG      808
Ser His Leu Gln Leu Leu Gly Ala Val Cys Met Phe Leu Ala Ser Arg
        100                 105                 110

CTC AAA GAG TCC AGC CCA CTG ACT GCC AAA AAG CTG TGC ATT TAT ACC      856
Leu Lys Glu Ser Ser Pro Leu Thr Ala Lys Lys Leu Cys Ile Tyr Thr
    115                 120                 125

GAC AAC TCC ATC AAG CCT CAG GAG CTG CTG GAG TGG GAA CTG GTG GTG      904
Asp Asn Ser Ile Lys Pro Gln Glu Leu Leu Glu Trp Glu Leu Val Val
130                 135                 140                 145

TTG GGA AAG TTG AAG TGG AAC CTG GCA GCT GTC ACG CCT CAT GAC TTC      952
Leu Gly Lys Leu Lys Trp Asn Leu Ala Ala Val Thr Pro His Asp Phe
                150                 155                 160

ATT TAG TAC ATC TTG CAC AAG CTG CCC CAG CAG CGG GAG AAG CTG TCT     1000
Ile     Tyr Ile Leu His Lys Leu Pro Gln Gln Arg Glu Lys Leu Ser
            165                 170                 175

CCAATCTGCA AGCAAGTCCA GAACTTCAAT GCTCTGTAT GCA ATG TAC CCG CCA      1054
                                           Ala Met Tyr Pro Pro
                                                       180

TCA ATG GTT GCA ACT GGA AGT GTA GGA GCA GCT ATC TGT GGA CTT CAG     1102
Ser Met Val Ala Thr Gly Ser Val Gly Ala Ala Ile Cys Gly Leu Gln
            185                 190                 195

CAA CAT GAG GAA GTG AGC TCA CTC CCT TGC AAT GCC CTG ACT GAG CTG     1150
Gln His Glu Glu Val Ser Ser Leu Pro Cys Asn Ala Leu Thr Glu Leu
        200                 205                 210

CTG GCA AAG ATC ACC AAC ACA GAT GTG GAT TGT CTC AAA A GCC AAC       1196
Leu Ala Lys Ile Thr Asn Thr Asp Val Asp Cys Leu Lys   Ala Asn
215                 220                 225

CGG GAG CAT ATT GAG GTG GTC TTC CTC AAC AGC CTG CAG CAG TGC CAT     1244
Arg Glu His Ile Glu Val Val Phe Leu Asn Ser Leu Gln Gln Cys His
230                 235                 240                 245

CAG GAC CAG CAG GAC AGA TCC AAG TCA GAG GAT GAA CTG GGC CAA GCA     1292
Gln Asp Gln Gln Asp Arg Ser Lys Ser Glu Asp Glu Leu Gly Gln Ala
            250                 255                 260

AGC ACC CCT ATA GAC CTG TGA GAT ATC GAC CTG GAGGATGGCA GTCCAGCTGA   1345
Ser Thr Pro Ile Asp Leu     Asp Ile Asp Leu
                265                 270

GAGGCGCATT CATAATCTGC TGTCTCCTTC TTTCTGGTTA TGTTTTGTTC TTTGTATCTT   1405

AGGGCGAAAC TTAAAAAAAA AAACCTCTGC CCCCACATAG TTCGTGTTTA AAGATCT     1462
```

(2) INFORMATION FOR SEQ ID NO:31:

(i) SEQUENCE CHARACTERISTICS:
        (A) LENGTH: 39 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:31:

```
Met Gln Leu Leu Gly Cys Glu Val Asp Pro Val Leu Arg Ala Thr Arg
 1              5                  10                  15
```

```
         Asp Cys Asn Leu Leu Gln Val Asp Arg Val Leu Lys Asn Leu Leu Ala
                     20                  25                  30

Ile Lys Lys Arg Tyr Leu Gln
                 35

(2) INFORMATION FOR SEQ ID NO:32:

(i) SEQUENCE CHARACTERISTICS:
          (A) LENGTH: 2022 base pairs
          (B) TYPE: nucleic acid
          (C) STRANDEDNESS: double
          (D) TOPOLOGY: linear (ii) MOLECULE TYPE: DNA (genomic)

(ix) FEATURE:
          (A) NAME/KEY: CDS
          (B) LOCATION: join(1137..1211, 1211..1678, 1680..1790)

(xi) SEQUENCE DESCRIPTION: SEQ ID NO:32:
```

| | |
|---|---:|
| AAGCTTCCAG ATTAGAAAAG AAAAAATAAA ACTATCTTTA TTTGCAGATG ACATGATCGG | 60 |
| TCCATTCTCA TGCTGCTTAT AAAGACATAC CCAAGACTGG ATAATTTATA AAGGAAAGAG | 120 |
| GTTTGGCTCA CAGTTCCCCA TGGGTGGAGA GGCCTCACAA TCATGGCGAA AGAGCAAGGA | 180 |
| GCATCTCACA TGGCAGCAGG CAAGAAAAGA ATGAGAGCCA CGCCAGAGGG AAACCCCTTA | 240 |
| TAAAATCATC AGATCTCGAG AGACTTATTC ACTGTCAGGA GAACAGTATG GAGGAAACGC | 300 |
| CCTTATGATT CAATTATCTC GCACTGTGTT CCTCCCACAA CACATGGGAA TTATGGGAGC | 360 |
| TACAATTCAA GATGAGATTT GGGTGGAGAC ACAGCCAAAC CATATCAATC TTTTTTTTCT | 420 |
| TATTCTTTTT TTTTTTTTTT TTTTTTTTGA GATGGAGTCC CACTCTGTTA TCTAGGCTGG | 480 |
| AGTGCAGTGG TGTGTGATCT TGGCTCACTG CAACCTCAGC CTCCCAGGTT CAAGCGATTC | 540 |
| TCCTGCCTCA GACTCCTGAA TAGCTGAAAT TACAGGCACC TGCCACTACG CCTGGCAAAT | 600 |
| ATTTTTTGTT TGTTTGTTTG TTTGTTTGTT TGTTTTGAGA CAGAGTCTCT CTCTGTCGCC | 660 |
| CAGGCTGGAG TGCAGTGGGC GCGATCTCAG CTCACTGCAA ACTCTGCTCC CGGGTTCAAG | 720 |
| CCATTCTCCT GCCTCAGCTC CCAAGTAGCT GGGACTACAG GCGCCCACCA CCACCATGCC | 780 |
| AGGCTAATTT TTTGTATTTT TAGTAGAGAC AGGGTTTCAC CGTGTTAGCC AGGATGGTCT | 840 |
| CAATCTCCTG ACCTCGTGAT CCGCCCACCT CGGCCTCCCA AAGTGCTGGG ATTACAGGCG | 900 |
| TGAGCCACTA TGCCCAACCG TATCAATCTT GTATATAGAA AAACCTAAGG AATCTACAAA | 960 |
| AAAACCCTAT TATAACTAAT ATAATAATAA TCTGCAAAGT TGTAGACTAT GAGATCAATA | 1020 |
| TACAAAAATT AACTCAATTT CTTTACATGT ACAATGAATA ACCCCAAAAC AAAACTGGGA | 1080 |
| ATATAATTCT ATTTTTAATA GTATCACAAA GAATGACAAT ACTTAGAAAC AAATGA | 1136 |

```
TGG GCG CTA GCT TGC ACT CCC GCC CTG CCT GTG CGC TGC CCG AGT GTG         1184
Trp Ala Leu Ala Cys Thr Pro Ala Leu Pro Val Arg Cys Pro Ser Val
 1               5                  10                  15

GAG CTG CTA TGC TGC GAA GGC TCG AGG GAC CCG CAG ACG CCA GGG GAT         1232
Glu Leu Leu Cys Cys Glu Gly Ser Arg Asp Pro Gln Thr Pro Gly Asp
                 20                  25                  30

CAG CGC GTC CTG CAG AGC TTG CTC CCC TTG GAG TAG CGC TGC GTG CAC         1280
Gln Arg Val Leu Gln Ser Leu Leu Pro Leu Glu     Arg Cys Val His
         35                  40                      45

TGC GCC TAC TTC CAG TGC GTG CAA AGG GAG AGC AAG CCG CAC ATG CGG         1328
Cys Ala Tyr Phe Gln Cys Val Gln Arg Glu Ser Lys Pro His Met Arg
     50                  55                  60

AAG ATG CTG GTT TAC TGG ATG CTG GAG GTG TGT GAG GAG CAG TGC TGT         1376
Lys Met Leu Val Tyr Trp Met Leu Glu Val Cys Glu Glu Gln Cys Cys
```

```
                   65                  70                  75                  80
GAG GAG GAG CAG TGC TGT AAG GAG GAA GTC TTT CCC CTG GCC ATG AAC          1424
Glu Glu Glu Gln Cys Cys Lys Glu Glu Val Phe Pro Leu Ala Met Asn
                    85                  90                  95

CAC CTG CAT GCT ACC TGT CCT ACG TCC CCA CCC ACC CGA AAG GCA CAG          1472
His Leu His Ala Thr Cys Pro Thr Ser Pro Pro Thr Arg Lys Ala Gln
                100                 105                 110

TTG CAG CTC TTG GTT GCG GTC TCC ATG CGG CTG GCC TCC AAG CTG CGT          1520
Leu Gln Leu Leu Val Ala Val Ser Met Arg Leu Ala Ser Lys Leu Arg
            115                 120                 125

AAG ACT GGG CCC ATG ACC ATT GAG AAA ATG TGC ATC TAC ACC GAC CAC          1568
Lys Thr Gly Pro Met Thr Ile Glu Lys Met Cys Ile Tyr Thr Asp His
        130                 135                 140

GCT GTC TCT CCC TGC CAG TTG CGG GAC TGG GAG GTG ATG GTC CTG GGG          1616
Ala Val Ser Pro Cys Gln Leu Arg Asp Trp Glu Val Met Val Leu Gly
145                 150                 155                 160

AAG CTC AAA TGG GAC CTG GCC GCT GTG ATT GCT CAT GAC TTC TTG GCC          1664
Lys Leu Lys Trp Asp Leu Ala Ala Val Ile Ala His Asp Phe Leu Ala
                165                 170                 175

CTC ATT CTG CAC CGA C CGA CAG GCC TTG GTC AAA AAG CAT GCC CAG            1710
Leu Ile Leu His Arg   Arg Gln Ala Leu Val Lys Lys His Ala Gln
                180                 185                 190

ATC TTT TTG GCT GTC TGT GCT ACA GAT TAC ACC TTT GCC ATG TAC CCA          1758
Ile Phe Leu Ala Val Cys Ala Thr Asp Tyr Thr Phe Ala Met Tyr Pro
            195                 200                 205

CCA TCC AGT TGT GAA AAC AAC CCA AAT GCC TGT AACTGATGAA CAGATAACCA        1811
Pro Ser Ser Cys Glu Asn Asn Pro Asn Ala Cys
        210                 215

TATGTGATAT ATATCAATAC AATGGAATAT GGCCTGGCAT GCTGGCTTAC GCTGTAATCC        1871

TGCACTTTGG GAGGCCAAAG TGGAGGATCA CTTGAGCCGA GGAGTTCAAG GCCAGCCTGG        1931

GCACAAAGTG AGACTCCTTC TAAAAAAATA AATAAAATA AAAAATAAAA ACAATGTAAT         1991

ATTATTCAGC CATAGAAAGG AATAAAGTAC T                                      2022

(2) INFORMATION FOR SEQ ID NO:33:

(i) SEQUENCE CHARACTERISTICS:
        (A) LENGTH: 43 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:33:

Trp Ala Leu Ala Cys Thr Pro Ala Leu Pro Val Arg Cys Pro Ser Val
  1               5                  10                  15

Glu Leu Leu Cys Cys Glu Gly Ser Arg Asp Pro Gln Thr Pro Gly Asp
                 20                  25                  30

Gln Arg Val Leu Gln Ser Leu Leu Pro Leu Glu
             35                  40

(2) INFORMATION FOR SEQ ID NO:34:

(i) SEQUENCE CHARACTERISTICS:
        (A) LENGTH: 1317 base pairs
        (B) TYPE: nucleic acid
        (C) STRANDEDNESS: double
        (D) TOPOLOGY: linear (ii) MOLECULE TYPE: DNA (genomic)
```

(xi) SEQUENCE DESCRIPTION: SEQ ID NO:34:

```
GAGCTCGATC AGTACACTCG TTTGTTTAAT TGATAATTGT CCTGAATTAT GCCGGCTCCT        60
GCAGCCCCCT CACGCTCACG AATTCAGTCC CAGGGCAAAT TCTAAAGGTG AAGGGACGTC       120
TACACCCCCA ACAAAACCAA TTAGGAACCT TCGGTGGGTC TTGTCCCAGG CAGAGGGGAC       180
TAATATTTCC AGCAATTTAA TTTCTTTTTT AATTAAAAAA AATGAGTCAG AATGGAGATC       240
ACTGTTTCTC AGCTTTCCAT TCAGAGGTGT GTTTCTCCCG GTTAAATTGC CGGCACGGGA       300
AGGGAGGGGG TGCAGTTGGG GACCCCCGCA AGGACCGACT GGTCAAGGTA GGAAGGCAGC       360
CCGAAGAGTC TCCAGGCTAG AAGGACAAGA TGAAGGAAAT GCTGGCCACC ATCTTGGGCT       420
GCTGCTGGAA TTTTCGGGCA TTTATTTTAT TTTATTTTTT GAGCGAGCGC ATGCTAAGCT       480
GAAATCCCTT TAACTTTTAG GTTACCCCTT GGGCATTTGC AACGACGCCC CTGTGCGCCG       540
GAATGAAACT TGCACAGGGG TTGTGTGCCC GGTCCTCCCC GTCCTTGCAT GCTAAATTAG       600
TTCTTGCAAT TTACACGTGT TAATGAAAAT GAAAGAAGAT GCAGTCGCTG AGATTCTTTG       660
GCCGTCTGTC CGCCCGTGGG TGCCCTCGTG GCGTTCTTGG AAATGCGCCC ATTCTGCCGG       720
CTTGGATATG GGGTGTCGCC GCGCCCCAGT CACCCCTTCT CGTGGTCTCC CCAGGCTGCG       780
TGCTGGCCGG CCTTCCTAGT TGTCCCCTAC TGCAGAGCCA CCTCCACCTC ACCCCCTAAA       840
TCCCGGGACC CACTCGAGGC GGACGGGCCC CCTGCACCCC TCTCGGCGGG GAGAAAGGCT       900
GCAGCGGGGC GATTTGCATT TCTATGAAAA CCGGACTACA GGGGCAACTG CCCGCAGGGC       960
AGCGCGGCGC CTCAGGGATG GCTTTTCGTC TGCCCCTCGC TGCTCCCGGC GTTCTGCCCG      1020
CGCCCCCTCC CCCTGCGCCC GCCCCCGCCC CCCTCCCGCT CCCATTCTCT GCCGGGCTTT      1080
GATCTTTGCT TAACAACAGT AACGTCACAC GGACTACAGG GGAGTTTTGT TGAAGTTGCA      1140
AAGTCCTGGA GCCTCCAGAG GGCTGTCGGC GCAGTAGCAG CGAGCAGCAG AGTCCGCACG      1200
CTCCGGCGAG GGGCAGAAGA GCGCGAGGGA GCGCGGGGCA GCAGAAGCGA GAGCCGAGCG      1260
CGGACCCAGC CAGGACCCAC AGCCCTCCCC AGCTGCCCAG GAAGAGCCCC AGCCATG        1317
```

(2) INFORMATION FOR SEQ ID NO:35:

(i) SEQUENCE CHARACTERISTICS:
       (A) LENGTH: 1624 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:35:

```
GAGCTCGAGC CACGCCATGC CCGCTGCACG TGCCAGCTTG GCCAGCACAT CAGGGCGCTG        60
GTCTCTCCCC TTCCTCCTGG AGTGAAATAC ACCAAAGGGC GCGGTGGGGG TGGGGGGTGA       120
CGGGAGGAAG GAGGTGAAGA AACGCCACCA GATCGTATCT CCTGTAAAGA CAGCCTTGAC       180
TCAAGGATGC GTTAGAGCAC GTGTCAGGGC CGACCGTGCT GGCGGCGACT TCACCGCAGT       240
CGGCTCCCAG GGAGAAAGCC TGGCGAGTGA GGCGCGAAAC CGGAGGGGTC GGCGAGGATG       300
CGGGCGAAGG ACCGAGCGTG GAGGCCTCAT GCTCCGGGGA AAGGAAGGGG TGGTGGTGTT       360
TGCGCAGGGG GAGCGAGGGG GAGCCGGACC TAATCCCTTC ACTCGCCCCC TTCCCTCCCG       420
GGCCATTTCC TAGAAAGCTG CATCGGTGTG GCCACGCTCA GCGCAGACAC CTCGGGCGGC       480
TTGTCAGCAG ATGCAGGGGC GAGGAAGCGG GTTTTTCCTG CGTGGCCGCT GGCGCGGGGG       540
AACCGCTGGG AGCCCTGCCC CCGGCCTGCG GCGGCCCTAG ACGCTGCACC GCGTCGCCCC       600
ACGGCGCCCG AAGAGCCCCC AGAAACACGA TGGTTTCTGC TCGAGGATCA CATTCTATCC       660
```

```
CTCCAGAGAA GCACCCCCCT TCCTTCCTAA TACCCACCTC TCCCTCCCTC TTCTTCCTCT      720

GCACACACTC TGCAGGGGGG GGCAGAAGGG ACGTTGTTCT GGTCCCTTTA ATCGGGCTT       780

TCGAAACAGC TTCGAAGTTA TCAGGAACAC AGACTTCAGG GACATGACCT TTATCTCTGG      840

GTATGCGAGG TTGCTATTTT CTAAAATCAC CCCCTCCCTT ATTTTTCACT TAAGGGACCT      900

ATTTCTAAAT TGTCTGAGGT CACCCCATCT TCAGATAATC TACCCTACAT TCCTGGATCT      960

TAAATACAAG GGCAGGAGGA TTAGGATCCG TTTTTGAAGA AGCCAAAGTT GGAGGGTCGT     1020

ATTTTGGCGT GCTACACCTA CAGAATGAGT GAAATTAGAG GGCAGAAATA GGAGTCGGTA     1080

GTTTTTTGTG GGTTGCCCTG TCCGGGCCCC TGGCATGCAG GCTTGGATGG AGGGAGAGGG     1140

GTTGGGGGTT GCGGGGGACC GCGTTTGAAG TTGGGTCGGG CCAGCTGCTG TTCTCCTTAA     1200

TAACGAGAGG GGAAAAGGAG GGAGGGAGGG AGAGATTGAA AGGAGGAGGG GAGGACCGGG     1260

AGGGGAGGAA AGGGGAGGAG GAACCAGAGC GGGGAGCGCG GGGAGAGGGA GGAGAGCTAA     1320

CTGCCCAGCC AGCTTCGGTC ACGCTTCAGA GCGGAGAAGA GCGAGCAGGG GAGAGCGAGA     1380

CCAGTTTTAA GGGGAGGACC GGTGCGAGTG AGGCAGCCCC TAGGCTCTGC TCGCCCACCA     1440

CCCAATCCTC GCCTCCCTTC TGCTCCACCT TCTCTCTCTG CCCTCACCTC TCCCCCGAAA     1500

ACCCCCTATT TAGCCAAAGG AAGGAGGTCA GGGAACGCTC TCCCCTCCCC TTCCAAAAAA     1560

CAAAAACAGA AAAACCCTTT TCCAGGCCGG GGAAAGCAGG AGGGAGAGGG CGCGGGCTGC     1620

CATG                                                                 1624

(2) INFORMATION FOR SEQ ID NO:36:

(i) SEQUENCE CHARACTERISTICS:
        (A) LENGTH: 3158 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:36:

GAGCTCCCGT CCCCATACTA CAGGTTCACA TCCAGCTTTC AGGACTAGTC AGTCTATGTG       60

GCCCTCCCTC AATTAATAAA TCAGCAACTA ATTTGCCAGG TGCGGTGGTT TGTGCCTGTA      120

ATCCCAGCAC TTTAGGAAGC TGAGGCAGGC AGATCACTTG AGGTCAGGAG TTCGAGACCA      180

GCCTGGCCAA CATGGTGAAA TCCCGTATCT ACTGAAAATA CAAAAATTAG CCGGGCATGG      240

TGGTATGCAC CCGTAATCCC AGCTACTCAG GAAGCTGAGG CAGGAGAATC ACTTGAAACC      300

GGGAGGCAGA GGTTGCAGTA AGCTGCACTC CAGCCTGGTG ACAAGAGCAA AACTTTGTGT      360

CAAAAAAACA AAGAAAACCA AAAACAAAG GAAAACACAA AAACCCTTC TATTTGTTAA        420

AAAAAAAAAA ATCCACCGTG AACCAAAAAT TAGTAAAAAC AATGAACTAA AATTTTGTTT      480

TTGCAAAATG TATGATAACA AAATGTTAAG GAAGGTCATG TGCCGTTATG GTTCACTGCA      540

GCCTTGAACT CCTGGGCTCA AGCGATCCTC CTGCTTCGGT CTCCCTAGTA GCTGGGACTA      600

CAGGCTTGTG CCACCGCACC CAGCTTATTT TTTTTTTTA TTTTTTGTAG AGATAGGAGT      660

CTTGCTTTGT TGTCCAGGCT GGTCTTCAAC TCCTAGCTTC CAGTGATCCT CCTGCCTCAG      720

CCTCCCAAGT GCTGGGCCTG ATGGGACATT TTTATACATA GTGCCATGTA CCTATAAATG      780

AGAAGTTTTA AAAATACTGA TTTTAAAAAT TAATTTATGT CAAGAATTTT TATACCAAAG      840

TTAAAAAACC AAACCGAAAA TATGAAAAGG GTTAATATCT TTGAGAGGTG ATGAGAACTT      900

ATAAGTCAAT AAGAGAAAAC AAACATCCCT ATAAATGAAT AAGCTAAGGA CATGAATGGG      960
```

```
TAATGTACAT AAGAAATGTA AATGTCTAGT AATATGCCAA AATAGATTTA TTATTACTAA    1020

TAAGCCACTT TCACTCTCTA GTTGGCAGAG TTGTTTTGAA AAATAGATAT GTAATGATGG    1080

TGGAAAAGAT TGGTTTAACT ATTCAGCAGG AAAATTTGGC AATTAGAAGT GTATCAAAAG    1140

CCTTAGAATG TTTCATAACC TTAGATTGGG AAATTCCACT TCTAGAAATT AATTCACTTC    1200

TAGAAATAAT CATGAGTGTG CACAAAGATA TTACCACAAA AATATTTTAC AGTATTATGT    1260

CTAATAGAGA AGAACTAGAA ATAATTTAAA TTTCCACCAA TACAGGTTTG CCAAAATACA    1320

TTTTGTACAT TCACCTAATG GTATATTATG TCCCTATTAC AAATTACGTC CTAGAATATT    1380

TAATAGCATG GAAAAGTGTT AACAGTATTT TTTTAATGAA AAAAGCTTAC AAAACAGTTT    1440

GTGATGATTC CATTTAAAAT GTGTGTTTAT TCATAGAACA AAGATTAGAA AAATAAACAT    1500

TGATATATTA AAGGGTTATT TCATGGCAAA TTGCAAATGA TTATTTCCTT TTTTTGTGGC    1560

TTATTTGTAT TTTTGAAGTT TTCTACAATG TAAAAGAATA TTTTATGATA TGAAAACTAC    1620

AATACAATTT ATAATATAAG AAAGAATAAT TCGGCCGGGA ACGGTGGCTC ACGCCTGTAA    1680

TCCCAGCACT TTTGGAGGCC GAGACCGGCG GATCACGAGG TCAGGGGTTC AAGACTAGCC    1740

TGGCCAACAT AGTGAAACCC CATCTCTACG AAAAATACAA AAATTAGTCA GGCATGGTGG    1800

TGCGTGCCTG TAGTCCCAGC TACTCGGGAA TTGCTTGAAC CCGGGAGGTG GAGGTTGCAG    1860

TGAGCCCAGA TCGCACCACT GCACTCCAGC TTGAGCAACA GAGTAGACTT CGTCTCAAAA    1920

AAAAAAAAAA AAAAAAAAAG AATAATTAAC AGAAATGGT TAGACACTTC CTTAGTGTCT    1980

CCTAAGTCAG GAGGACCCCA GTAGGGCAGG GATCCTCATG GCCTCCTCCC ATTTGGAGCA    2040

TTATTGGAGG TCTTTTTCGG CCTCTTCGTC AAGTGGAATC TAGCTTCCGG TAAAACTACA    2100

AAGTAACCAA AAGTTTGGGA GGTGGAAGAA ATGCAACCGG TAGATCTCAC AGAGTCTGTG    2160

CAAGAAACTG ATTCAATGAG AATCTAGTTT CTCCGTCCAC AGTTTCTCCA AACAGAAACT    2220

AAGGCCGACT TTAGGGGCTT GTCCAAACCT AGGCAAGCAA CTTAACAAGG TGAGGCCATG    2280

ACTCCATGGC CTTTCCGTTC TGTTATATGC TGACTTAGAC TAAAGCTCTC ATACTTTAAA    2340

GTGCACAGAA ATCTAGTTAA AATGCAGATT CTGATTCAGG TTAGGGGTGG GCCTGAGAGT    2400

CTGCATTTCT AACCAGCTCC CAGGCGATGA CCACGCACGG GACAGGTCTG GGATCACAGT    2460

TTAACTAGCA ATGGTGTAGA ACACAGAATC TGCAGCAAGA AGGCCAGCTT CCCAATCCTA    2520

GCTCTGCCAC GGACCAACTG AATGACAGTT GCCTCGGTTT CCGAGTTTTC GTGAAGATGT    2580

AGTGAGTCAT TACATCGTGA GGCTTTCGAG CAGCGTTCAC TAAGAACTAG CTCTGACATT    2640

ATTTATCGCA TTCCTTAGAG CAAGCAGCCG GTGAAGTAGG GTTTGACGAA TGAATAAGTG    2700

AATGAATGAC CTTTGGAGAA AAATTGTTTC CTGGGTGACT AGAGTCCGAG AAGCAAAATG    2760

GGAGGGCCCG TGGTGGGTAG GAGGCCCACC TCCTAGAAAG TTCTCTGCAC CCGGTGGTCC    2820

AGAGGGCCTG GAGTGCCGGA AGCCGGCCGC GTTGCGCTCA CGGCCCAATG GGGCCGCGGG    2880

AGGGAGGGGA GAGCGCTCAG CCAACCCTTT CCGTTCCGGG CGCCGCAGCC CCGCCCCTCG    2940

GAGCGTTGCG ACGTCCGAGC ATTCCACGGT TGCTACATCG TCGCGAGGGG GGGCGCCTGT    3000

CAGGGAAGCG GCGCGCGCGC GGGCGGCGGG CGGGCTGGGG ATCCGCCGCG CAGTGCCAGC    3060

GCCAGCGCCA GACCCGCGCC CCGCGCTCTC CGGCCCGTCG CCTGTCTTGG GACTCGCGAG    3120

CCCGCACTCC CGCCCTGCCT GTTCGCTGCC CGAGTATG                           3158
```

(2) INFORMATION FOR SEQ ID NO:37:

(i) SEQUENCE CHARACTERISTICS:
        (A) LENGTH: 1089 base pairs
        (B) TYPE: nucleic acid (C) STRANDEDNESS: double
(D) TOPOLOGY: linear (ii) MOLECULE TYPE: DNA (genomic)

(ix) FEATURE:
    (A) NAME/KEY: CDS
    (B) LOCATION: 13..888

(xi) SEQUENCE DESCRIPTION: SEQ ID NO:37:

```
CCGGCCGCCG CG ATG CAG AAA TAC GAG AAA CTG GAA AAG ATT GGG GAA              48
              Met Gln Lys Tyr Glu Lys Leu Glu Lys Ile Gly Glu
                1               5                  10

GGC ACC TAC GGA ACT GTG TTC AAG GCC AAA AAC CGG GAG ACT CAT GAG            96
Gly Thr Tyr Gly Thr Val Phe Lys Ala Lys Asn Arg Glu Thr His Glu
            15                  20                  25

ATC GTG GCT CTA AAA CGG GTG AGG CTG GAT GAC GAT GAT GAG GGT GTG           144
Ile Val Ala Leu Lys Arg Val Arg Leu Asp Asp Asp Asp Glu Gly Val
        30                  35                  40

CCG AGT TCC GCC CTC CGG GAG ATC TGC CTA CTC AAG GAG CTG AAG CAC           192
Pro Ser Ser Ala Leu Arg Glu Ile Cys Leu Leu Lys Glu Leu Lys His
 45                  50                  55                  60

AAG AAC ATC GTC AGG CTT CAT GAC GTC CTG CAC AGC GAC AAG AAG CTG           240
Lys Asn Ile Val Arg Leu His Asp Val Leu His Ser Asp Lys Lys Leu
                65                  70                  75

ACT TTG GTT TTT GAA TTC TGT GAC CAG GAC CTG AAG AAG TAT TTT GAC           288
Thr Leu Val Phe Glu Phe Cys Asp Gln Asp Leu Lys Lys Tyr Phe Asp
            80                  85                  90

AGT TGC AAT GGT GAC CTC GAT CCT GAG ATT GTA AAG TCA TTC CTC TTC           336
Ser Cys Asn Gly Asp Leu Asp Pro Glu Ile Val Lys Ser Phe Leu Phe
        95                  100                 105

CAG CTA CTA AAA GGG CTG GGA TTC TGT CAT AGC CGC AAT GTG CTA CAC           384
Gln Leu Leu Lys Gly Leu Gly Phe Cys His Ser Arg Asn Val Leu His
110                 115                 120

AGG GAC CTG AAG CCC CAG AAC CTG CTA ATA AAC AGG AAT GGG GAG CTG           432
Arg Asp Leu Lys Pro Gln Asn Leu Leu Ile Asn Arg Asn Gly Glu Leu
125                 130                 135                 140

AAA TTG GCT GAT TTT GGC CTG GCT CGA GCC TTT GGG ATT CCC GTC CGC           480
Lys Leu Ala Asp Phe Gly Leu Ala Arg Ala Phe Gly Ile Pro Val Arg
                145                 150                 155

TGT TAC TCA GCT GAG GTG GTC ACA CTG TGG TAC CGC CCA CCG GAT GTC           528
Cys Tyr Ser Ala Glu Val Val Thr Leu Trp Tyr Arg Pro Pro Asp Val
            160                 165                 170

CTC TTT GGG GCC AAG CTG TAC TCC ACG TCC ATC GAC ATG TGG TCA GCC           576
Leu Phe Gly Ala Lys Leu Tyr Ser Thr Ser Ile Asp Met Trp Ser Ala
        175                 180                 185

GGC TGC ATC TTT GCA GAG CTG GCC AAT GCT GGG CGG CCT CTT TTT CCC           624
Gly Cys Ile Phe Ala Glu Leu Ala Asn Ala Gly Arg Pro Leu Phe Pro
    190                 195                 200

GGC AAT GAT GTC GAT GAC CAG TTG AAG AGG ATC TTC CGA CTG CTG GGG           672
Gly Asn Asp Val Asp Asp Gln Leu Lys Arg Ile Phe Arg Leu Leu Gly
205                 210                 215                 220

ACG CCC ACC GAG GAG CAG TGG CCC TCT ATG ACC AAG CTG CCA GAC TAT           720
Thr Pro Thr Glu Glu Gln Trp Pro Ser Met Thr Lys Leu Pro Asp Tyr
                225                 230                 235

AAG CCC TAT CCG ATG TAC CCG GCC ACA ACA TCC CTG GTG AAC GTC GTG           768
Lys Pro Tyr Pro Met Tyr Pro Ala Thr Thr Ser Leu Val Asn Val Val
            240                 245                 250

CCC AAA CTC AAT GCC ACA GGG AGG GAT CTG CTG CAG AAC CTT CTG AAG           816
Pro Lys Leu Asn Ala Thr Gly Arg Asp Leu Leu Gln Asn Leu Leu Lys
        255                 260                 265

TGT AAC CCT GTC CAG CGT ATC TCA GCA GAA GAG GCC CTG CAG CAC CCC           864
```

```
Cys Asn Pro Val Gln Arg Ile Ser Ala Glu Glu Ala Leu Gln His Pro
        270                 275                 280

TAC TTC TCC GAC TTC TGT CCG CCC TAGGCCCGGG ACCCCGGCC TCAGCTGGGC      918
Tyr Phe Ser Asp Phe Cys Pro Pro
285                 290

CTGGCCTATT TAAGCCCCTC TTGAGAGGGG TGAGACAGTG GGGGTGCCTG GTGCGCTGTG    978

CTCAGCAGTG CTGGGCCAGC CGGGGTGGGG TGCCTGAGCC CGAATTTCTC ACTCCCTTTG   1038

TGGACTTTAT TTAATTTCAT AAATTGGCTC CTTTCCCACA AAAAAAAAAG G            1089

(2) INFORMATION FOR SEQ ID NO:38:

(i) SEQUENCE CHARACTERISTICS:
        (A) LENGTH: 292 amino acids
        (B) TYPE: amino acid
        (D) TOPOLOGY: linear (ii) MOLECULE TYPE: protein (xi) SEQUENCE DESCRIPTION: SEQ ID NO:38:

Met Gln Lys Tyr Glu Lys Leu Glu Lys Ile Gly Glu Gly Thr Tyr Gly
 1               5                  10                  15

Thr Val Phe Lys Ala Lys Asn Arg Glu Thr His Glu Ile Val Ala Leu
                20                  25                  30

Lys Arg Val Arg Leu Asp Asp Asp Glu Gly Val Pro Ser Ser Ala
            35                  40                  45

Leu Arg Glu Ile Cys Leu Leu Lys Glu Leu Lys His Lys Asn Ile Val
 50                  55                  60

Arg Leu His Asp Val Leu His Ser Asp Lys Lys Leu Thr Leu Val Phe
 65                  70                  75                  80

Glu Phe Cys Asp Gln Asp Leu Lys Lys Tyr Phe Asp Ser Cys Asn Gly
                85                  90                  95

Asp Leu Asp Pro Glu Ile Val Lys Ser Phe Leu Phe Gln Leu Leu Lys
                100                 105                 110

Gly Leu Gly Phe Cys His Ser Arg Asn Val Leu His Arg Asp Leu Lys
            115                 120                 125

Pro Gln Asn Leu Leu Ile Asn Arg Asn Gly Glu Leu Lys Leu Ala Asp
130                 135                 140

Phe Gly Leu Ala Arg Ala Phe Gly Ile Pro Val Arg Cys Tyr Ser Ala
145                 150                 155                 160

Glu Val Val Thr Leu Trp Tyr Arg Pro Pro Asp Val Leu Phe Gly Ala
                165                 170                 175

Lys Leu Tyr Ser Thr Ser Ile Asp Met Trp Ser Ala Gly Cys Ile Phe
            180                 185                 190

Ala Glu Leu Ala Asn Ala Gly Arg Pro Leu Phe Pro Gly Asn Asp Val
            195                 200                 205

Asp Asp Gln Leu Lys Arg Ile Phe Arg Leu Leu Gly Thr Pro Thr Glu
        210                 215                 220

Glu Gln Trp Pro Ser Met Thr Lys Leu Pro Asp Tyr Lys Pro Tyr Pro
225                 230                 235                 240

Met Tyr Pro Ala Thr Thr Ser Leu Val Asn Val Val Pro Lys Leu Asn
                245                 250                 255

Ala Thr Gly Arg Asp Leu Leu Gln Asn Leu Leu Lys Cys Asn Pro Val
            260                 265                 270

Gln Arg Ile Ser Ala Glu Glu Ala Leu Gln His Pro Tyr Phe Ser Asp
        275                 280                 285

Phe Cys Pro Pro
```

290

(2) INFORMATION FOR SEQ ID NO:39:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

TGGATGYTNG RAGTNTGYGA MGARCARAAR TGYGARGA                            38

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Trp Met Leu Glu Val Cys Glu Glu Gln Lys Cys Glu Glu
1             5                   10

(2) INFORMATION FOR SEQ ID NO:41:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:41:

Gly Thr Asn Thr Thr Tyr Cys Cys Asn Tyr Thr Asn Gly Cys Asn Ala
1             5                   10                15

Thr Gly Ala Ala Tyr Thr Ala Tyr Thr Asn Gly Ala
          20                25

(2) INFORMATION FOR SEQ ID NO:42:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Val Phe Pro Leu Ala Met Asn Tyr Leu Asp
1             5                   10

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

```
RTCNGTRTAD ATRCANARYT TYTC                                              24
```

(2) INFORMATION FOR SEQ ID NO:44:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Glu Lys Leu Cys Ile Tyr Thr Asp
1               5
```

(2) INFORMATION FOR SEQ ID NO:45:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Cys Tyr Phe Ser Asp Phe Cys Pro Pro
1               5
```

(2) INFORMATION FOR SEQ ID NO:46:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Cys Asp Glu Leu Asp Gln Ala Ser Thr Pro Thr Asp Val Arg Asp Ile
1               5                  10                  15
Asp Leu
```

(2) INFORMATION FOR SEQ ID NO:47:

(i) SEQUENCE CHARACTERISTICS:
        (A) LENGTH: 122 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:47:

```
Cys Ser Tyr Phe Lys Cys Val Gln Lys Ala Ile Gln Pro Tyr Met His
1               5                  10                  15

Arg Met Val Pro Leu Leu Met Val Met Leu Glu Val Cys Glu Glu Gln
                20                  25                  30

Lys Cys Glu Glu Lys Val Phe Pro Leu Ala Thr Ile Tyr Leu Asp Cys
            35                  40                  45

Phe Phe Ala Arg Ile Pro Thr Ser Lys Ser His Leu Gln Leu Leu Gly
        50                  55                  60

Ala Val Cys Met Phe Leu Ala Ser Arg Leu Lys Glu Ser Ser Pro Leu
```

```
              65                  70                  75                  80
Thr Ala Lys Lys Leu Cys Ile Tyr Thr Asp Asn Ser Ile Lys Pro Gln
                    85                  90                  95
Glu Leu Leu Glu Trp Glu Leu Val Val Leu Gly Lys Leu Lys Trp Asn
                100                 105                 110
Leu Ala Ala Val Thr Pro His Asp Phe Ile
            115                 120
```

(2) INFORMATION FOR SEQ ID NO:48:

(i) SEQUENCE CHARACTERISTICS:
        (A) LENGTH: 104 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:48:

```
Tyr Ile Leu His Lys Leu Pro Gln Gln Arg Glu Lys Leu Ser Ala Met
1               5                   10                  15
Tyr Pro Pro Ser Met Val Ala Thr Gly Ser Val Gly Ala Ala Ile Cys
                20                  25                  30
Gly Leu Gln Gln His Glu Val Ser Ser Leu Pro Cys Asn Ala Leu
            35                  40                  45
Thr Glu Leu Leu Ala Lys Ile Thr Asn Thr Asp Val Asp Cys Leu Lys
        50                  55                  60
Ala Asn Arg Glu His Ile Glu Val Val Phe Leu Asn Ser Leu Gln Gln
65                  70                  75                  80
Cys His Gln Asp Gln Gln Asp Arg Ser Lys Ser Glu Asp Glu Leu Gly
                85                  90                  95
Gln Ala Ser Thr Pro Ile Asp Leu
            100
```

(2) INFORMATION FOR SEQ ID NO:49:

(i) SEQUENCE CHARACTERISTICS:
        (A) LENGTH: 4 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:49:

```
Asp Ile Asp Leu
1
```

(2) INFORMATION FOR SEQ ID NO:50:

(i) SEQUENCE CHARACTERISTICS:
        (A) LENGTH: 174 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:50:

```
Arg Cys Val His Cys Ala Tyr Phe Gln Cys Val Gln Arg Glu Ser Lys
1               5                   10                  15
```

-continued

```
Pro His Met Arg Lys Met Leu Val Tyr Trp Met Leu Glu Val Cys Glu
            20              25              30

Glu Gln Cys Cys Glu Glu Glu Gln Cys Cys Lys Glu Glu Val Phe Pro
            35              40              45

Leu Ala Met Asn His Leu His Ala Thr Cys Pro Thr Ser Pro Pro Thr
    50              55              60

Arg Lys Ala Gln Leu Gln Leu Leu Val Ala Val Ser Met Arg Leu Ala
65              70              75              80

Ser Lys Leu Arg Lys Thr Gly Pro Met Thr Ile Glu Lys Met Cys Ile
            85              90              95

Tyr Thr Asp His Ala Val Ser Pro Cys Gln Leu Arg Asp Trp Glu Val
            100             105             110

Met Val Leu Gly Lys Leu Lys Trp Asp Leu Ala Ala Val Ile Ala His
            115             120             125

Asp Phe Leu Ala Leu Ile Leu His Arg Arg Gln Ala Leu Val Lys Lys
            130             135             140

His Ala Gln Ile Phe Leu Ala Val Cys Ala Thr Asp Tyr Thr Phe Ala
145             150             155             160

Met Tyr Pro Pro Ser Ser Cys Glu Asn Asn Pro Asn Ala Cys
                165             170
```